(12) United States Patent
Brinker et al.

(10) Patent No.: US 10,327,825 B2
(45) Date of Patent: Jun. 25, 2019

(54) SYSTEM AND METHOD FOR REDUCING AND STABILIZING FRACTURES IN BONE, SUBLUXATIONS, OR DISLOCATIONS

(71) Applicant: Cable Fix LLC, Hernando, MS (US)

(72) Inventors: Mark Brinker, Houston, TX (US); William Ricci, Richmond Heights, MO (US); Carey Bryant, Hernando, MS (US)

(73) Assignee: CABLE FIX LLC, Hernando, MS (US)

( * ) Notice: Subject to any disclaimer, the term of this patent is extended or adjusted under 35 U.S.C. 154(b) by 669 days.

(21) Appl. No.: 14/961,527

(22) Filed: Dec. 7, 2015

(65) Prior Publication Data

US 2017/0156771 A1    Jun. 8, 2017

(51) Int. Cl.
*A61B 17/82* (2006.01)
*A61B 17/68* (2006.01)
*A61B 17/60* (2006.01)

(52) U.S. Cl.
CPC ............ *A61B 17/82* (2013.01); *A61B 17/686* (2013.01); *A61B 2017/603* (2013.01); *A61B 2017/681* (2013.01)

(58) Field of Classification Search
CPC combination set(s) only.
See application file for complete search history.

(56) References Cited

U.S. PATENT DOCUMENTS

| | | |
|---|---|---|
| 479,938 A | 8/1892 | Fredlihp |
| 899,612 A | 9/1908 | Phillips |
| 3,166,072 A | 1/1965 | Sullivan, Jr. |
| 4,060,089 A | 11/1977 | Noiles |
| 4,532,927 A | 8/1985 | Miksza, Jr. |
| 4,534,350 A | 8/1985 | Golden et al. |
| 4,534,352 A | 8/1985 | Korthoff |
| 4,548,202 A | 10/1985 | Duncan |
| 4,573,469 A | 3/1986 | Golden et al. |
| 4,610,250 A | 9/1986 | Green |
| 4,754,758 A | 7/1988 | Lehmann |
| 4,932,960 A | 6/1990 | Green |
| 5,358,510 A | 10/1994 | Luscombe et al. |
| 5,478,353 A | 12/1995 | Yoon |
| 5,620,452 A | 4/1997 | Yoon |
| 5,665,109 A | 9/1997 | Yoon |
| 5,797,932 A | 8/1998 | Min et al. |
| 5,984,001 A | 11/1999 | Larsen et al. |
| 6,276,032 B1 | 8/2001 | Nortman et al. |
| 6,712,830 B2 | 3/2004 | Esplin |
| 6,966,919 B2 | 11/2005 | Sixto et al. |

(Continued)

*Primary Examiner* — Sameh R Boles
(74) *Attorney, Agent, or Firm* — Kunzler Bean & Adamson

(57) ABSTRACT

A first method, for reducing and stabilizing at least one of a fracture in, a dislocation of, and a subluxation of at least one bone, includes forming a hole in the at least one bone. The first method also includes anchoring a first portion of a cable relative to the at least one bone and positioning a second portion of the cable in the hole in the at least one bone. With the second portion of the cable positioned in the hole in the at least one bone, the method includes both tensioning the cable to a measurable and adjustable tension and, with the cable tensioned to the measurable tension, anchoring a third portion of the cable relative to the at least one bone.

17 Claims, 45 Drawing Sheets

(56) References Cited

U.S. PATENT DOCUMENTS

| | | |
|---|---|---|
| 7,033,378 B2 | 4/2006 | Smith et al. |
| 7,094,251 B2 | 8/2006 | Bonutti et al. |
| 7,678,122 B2 | 3/2010 | Kortenbach et al. |
| 7,854,750 B2 | 12/2010 | Bonutti et al. |
| 7,985,241 B2 | 7/2011 | Smith et al. |
| 8,080,020 B2 | 12/2011 | Kortenbach et al. |
| 8,114,100 B2 | 2/2012 | Smith et al. |
| 8,162,977 B2 | 4/2012 | Bonutti et al. |
| 8,454,628 B2 | 6/2013 | Smith et al. |
| 8,613,750 B2 | 12/2013 | Smith et al. |
| 9,039,596 B2 | 5/2015 | Sater |
| 9,220,503 B2 | 12/2015 | Ranchod |
| 9,788,827 B2 | 10/2017 | Miksza et al. |
| 2001/0051815 A1 | 12/2001 | Esplin |
| 2002/0029044 A1 | 3/2002 | Monassevitch et al. |
| 2004/0044366 A1 | 3/2004 | Bonutti et al. |
| 2004/0059349 A1 | 3/2004 | Sixto et al. |
| 2004/0059354 A1 | 3/2004 | Smith et al. |
| 2004/0059358 A1 | 3/2004 | Kortenbach et al. |
| 2007/0032825 A1 | 2/2007 | Bonutti et al. |
| 2008/0046007 A1 | 2/2008 | Schwemberger et al. |
| 2008/0046008 A1 | 2/2008 | Smith et al. |
| 2008/0097430 A1* | 4/2008 | Bernstein ........... A61B 17/1764 606/60 |
| 2008/0108897 A1 | 5/2008 | Bonutti et al. |
| 2008/0140095 A1 | 6/2008 | Smith et al. |
| 2008/0147116 A1 | 6/2008 | Smith et al. |
| 2008/0149685 A1 | 6/2008 | Smith et al. |
| 2010/0179568 A1 | 7/2010 | Kortenbach et al. |
| 2010/0198258 A1 | 8/2010 | Heaven et al. |
| 2011/0040307 A1 | 2/2011 | Ranchod |
| 2011/0092993 A1 | 4/2011 | Jacobs |
| 2011/0201877 A1 | 8/2011 | Sater |
| 2012/0065638 A1* | 3/2012 | Moore .................. A61B 17/72 606/62 |
| 2012/0130374 A1 | 5/2012 | Bouduban et al. |
| 2012/0143247 A1 | 6/2012 | Smith et al. |
| 2016/0081686 A1 | 3/2016 | Miksza et al. |
| 2016/0100835 A1 | 4/2016 | Linder et al. |
| 2016/0346023 A1 | 12/2016 | Bouduban et al. |
| 2017/0156738 A1 | 6/2017 | Ricci et al. |
| 2017/0156772 A1 | 6/2017 | Brinker et al. |
| 2017/0156774 A1 | 6/2017 | Bryant et al. |
| 2017/0156775 A1 | 6/2017 | Bryant et al. |
| 2017/0156779 A1 | 6/2017 | Bryant et al. |
| 2017/0156847 A1 | 6/2017 | Ricci et al. |
| 2018/0055550 A1 | 3/2018 | Bryant et al. |

* cited by examiner

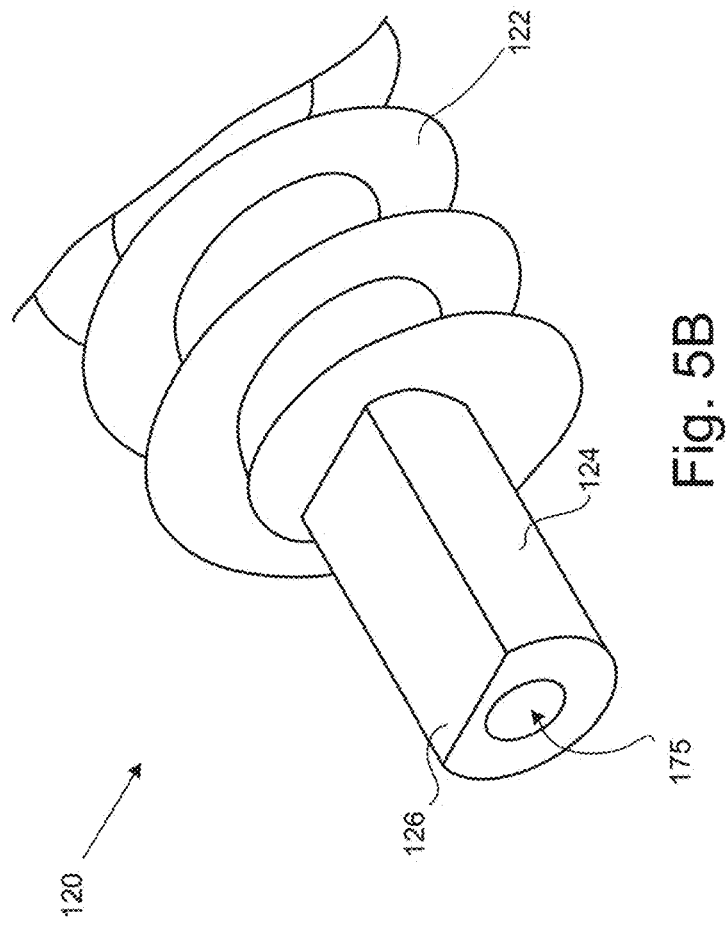
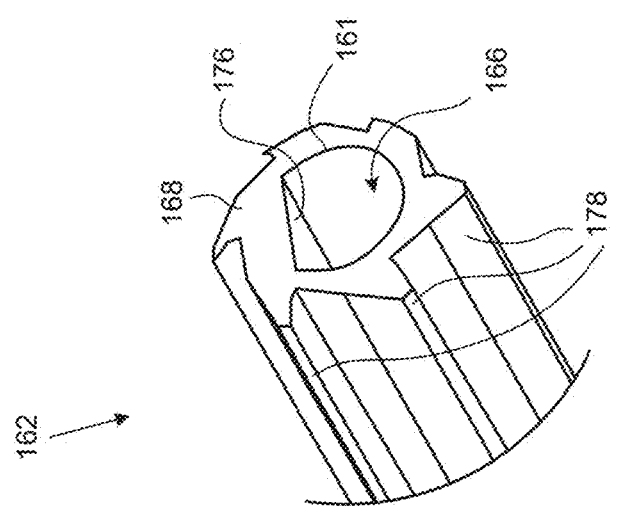
Fig. 5B
Fig. 5A

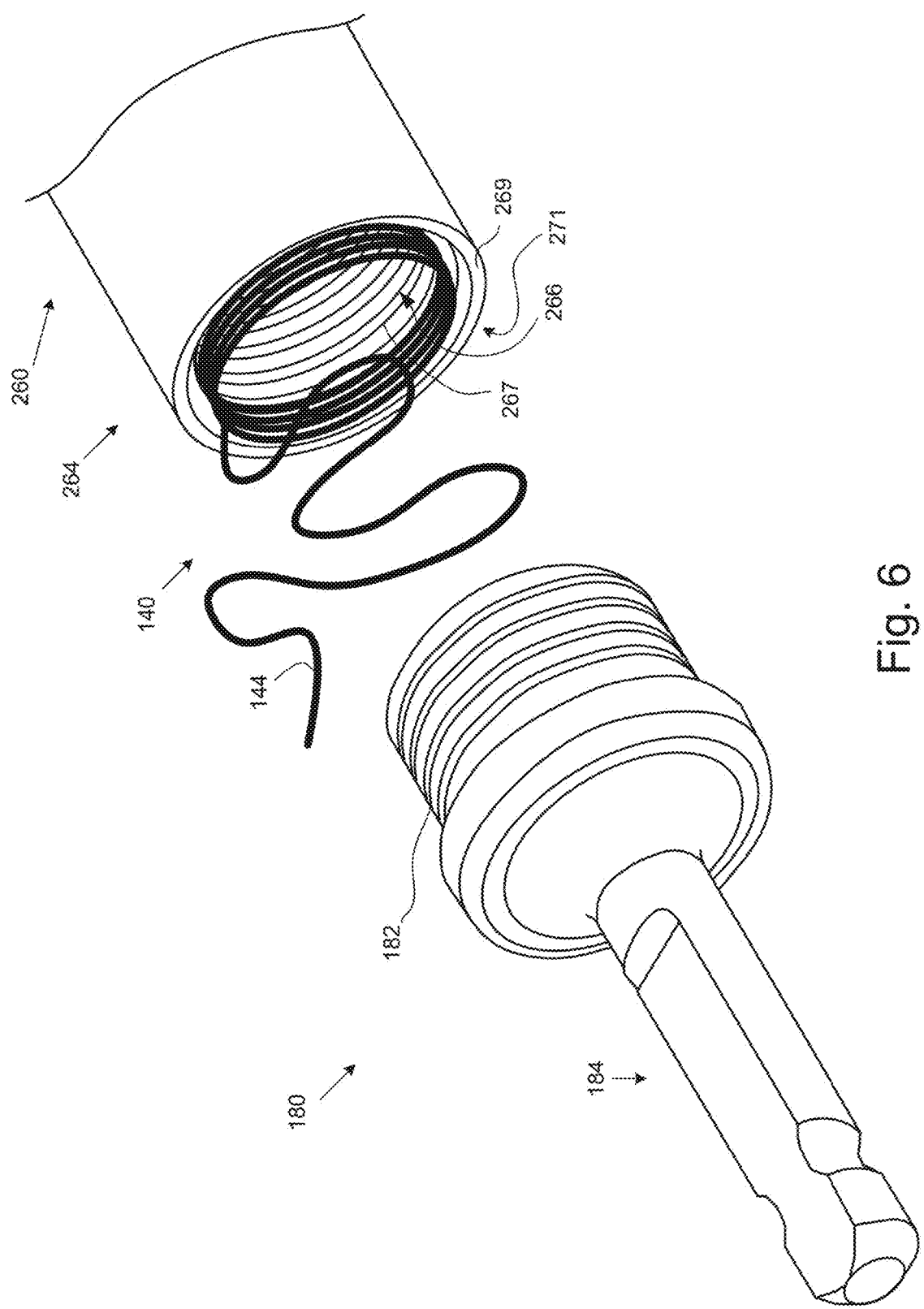

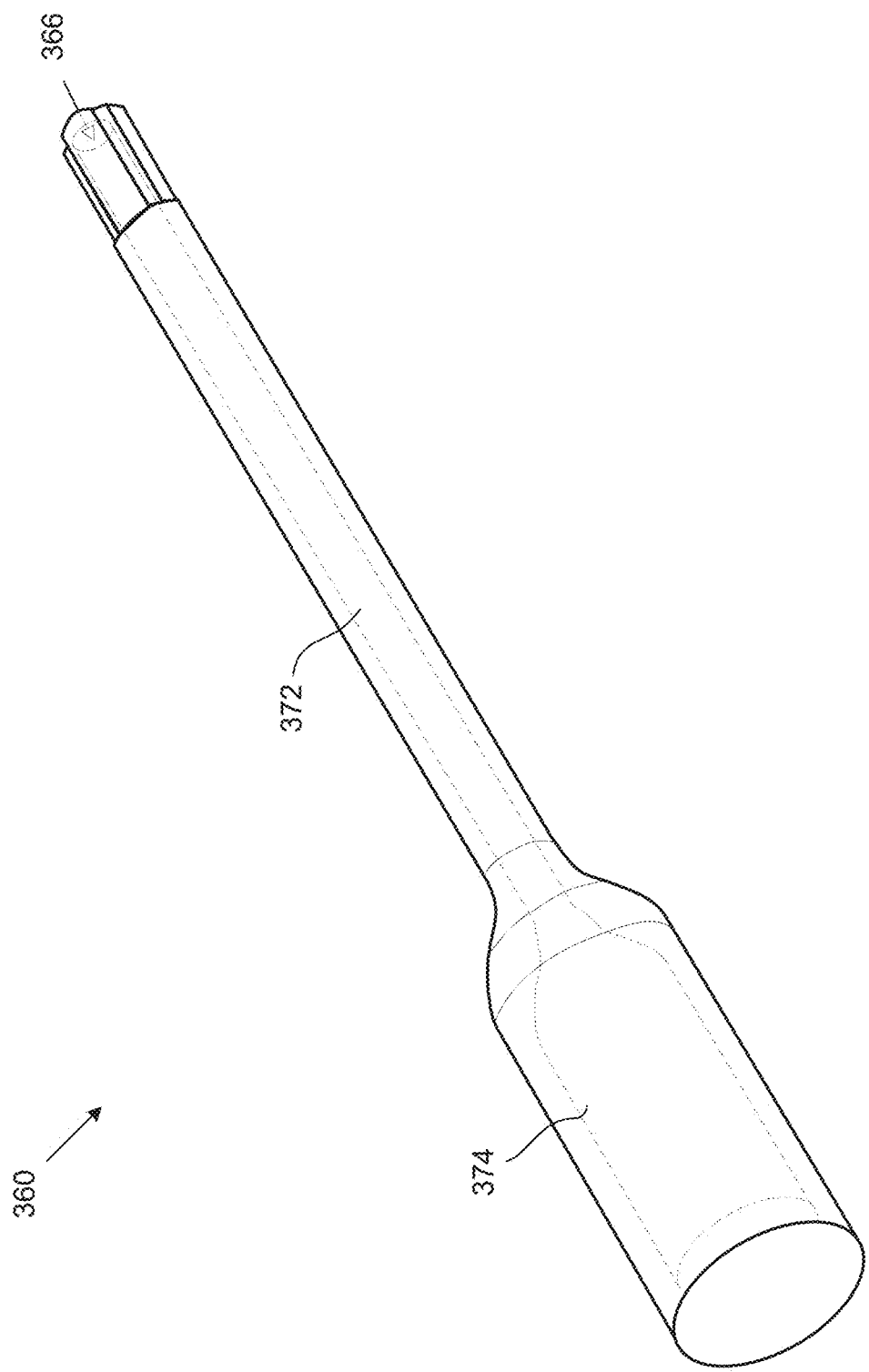

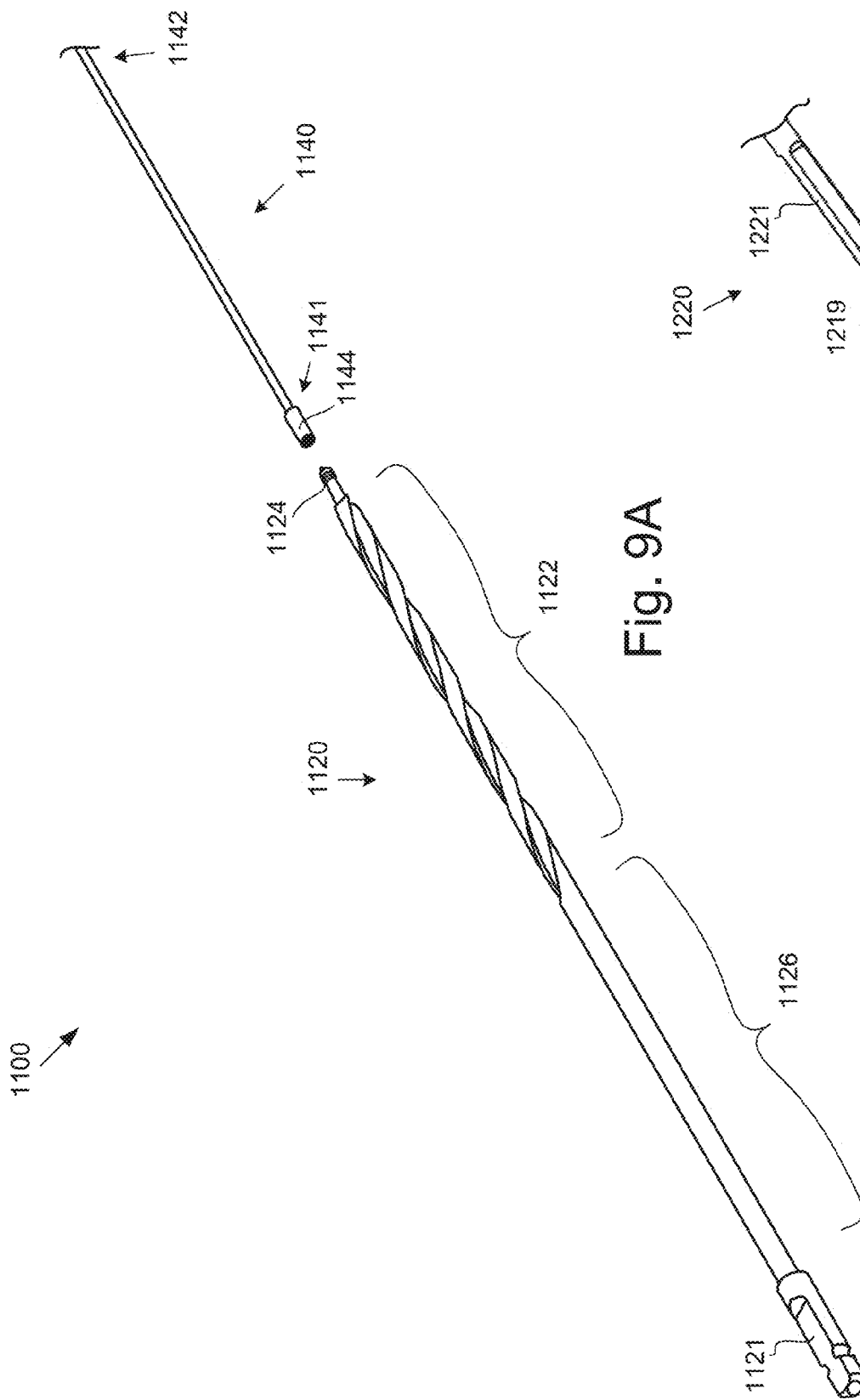
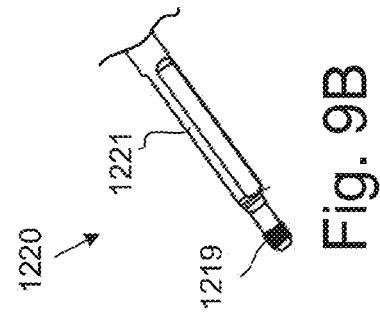
Fig. 9A
Fig. 9B

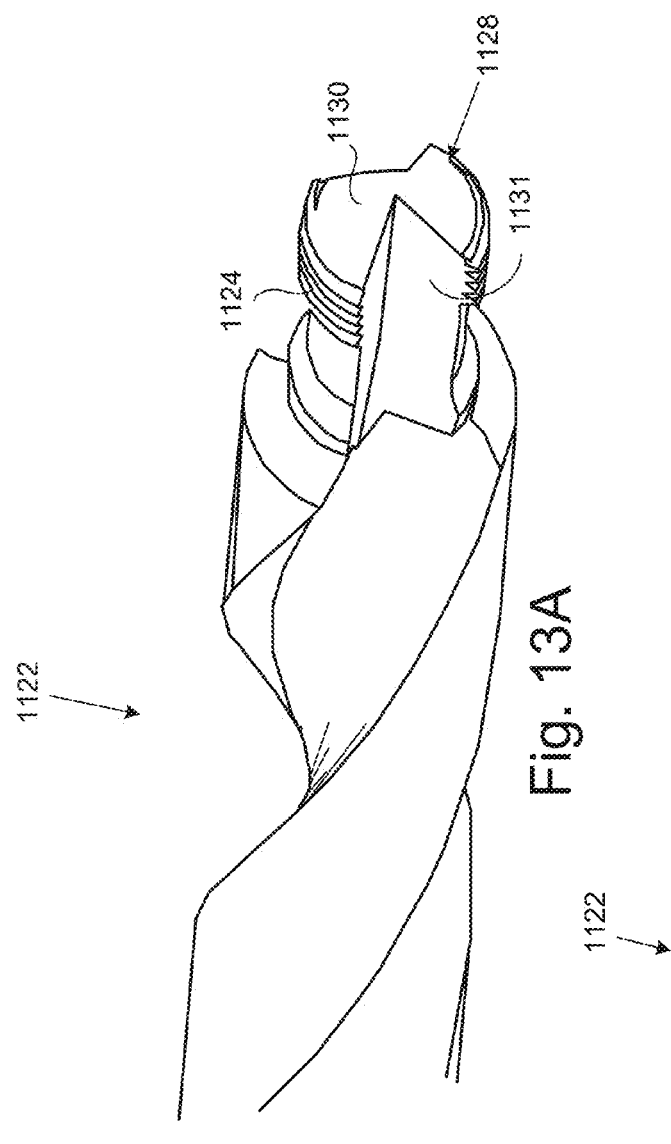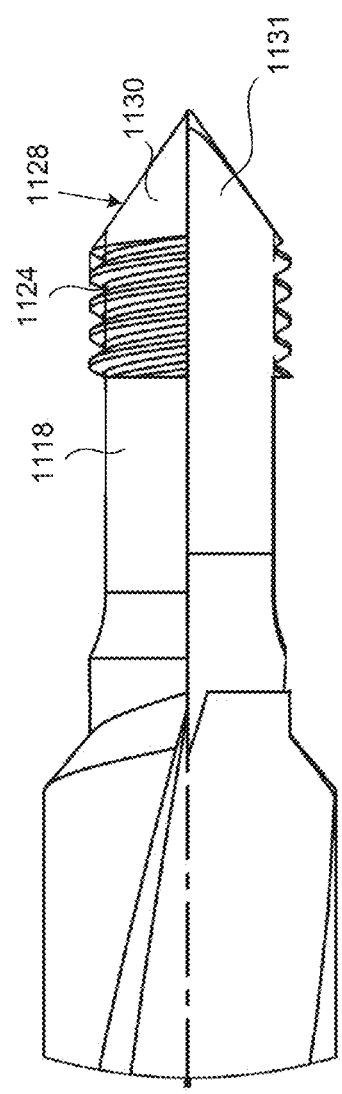
Fig. 13A
Fig. 13B

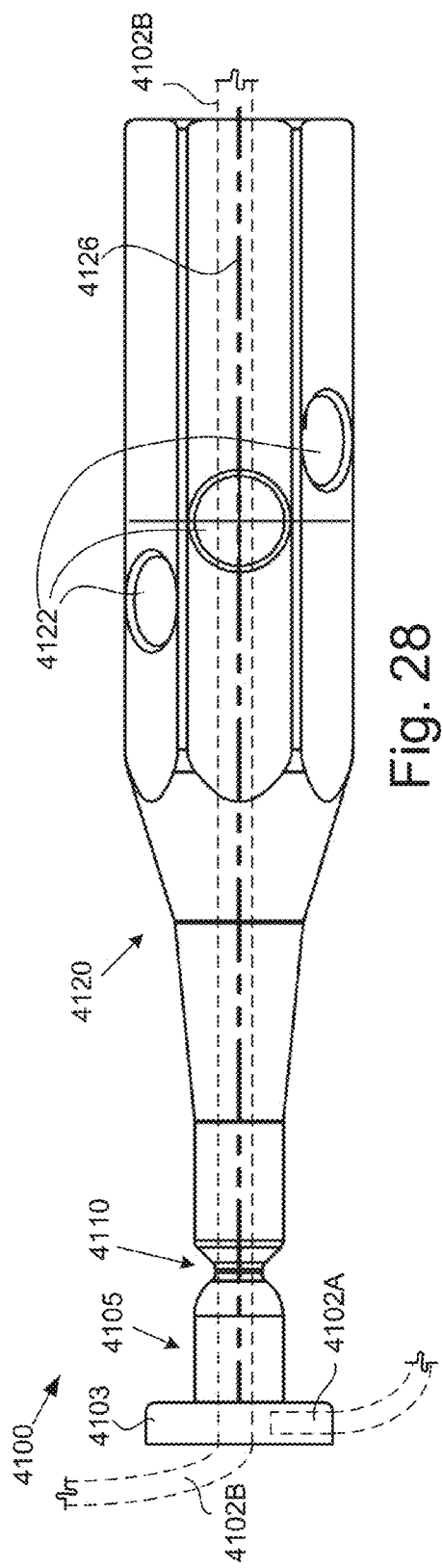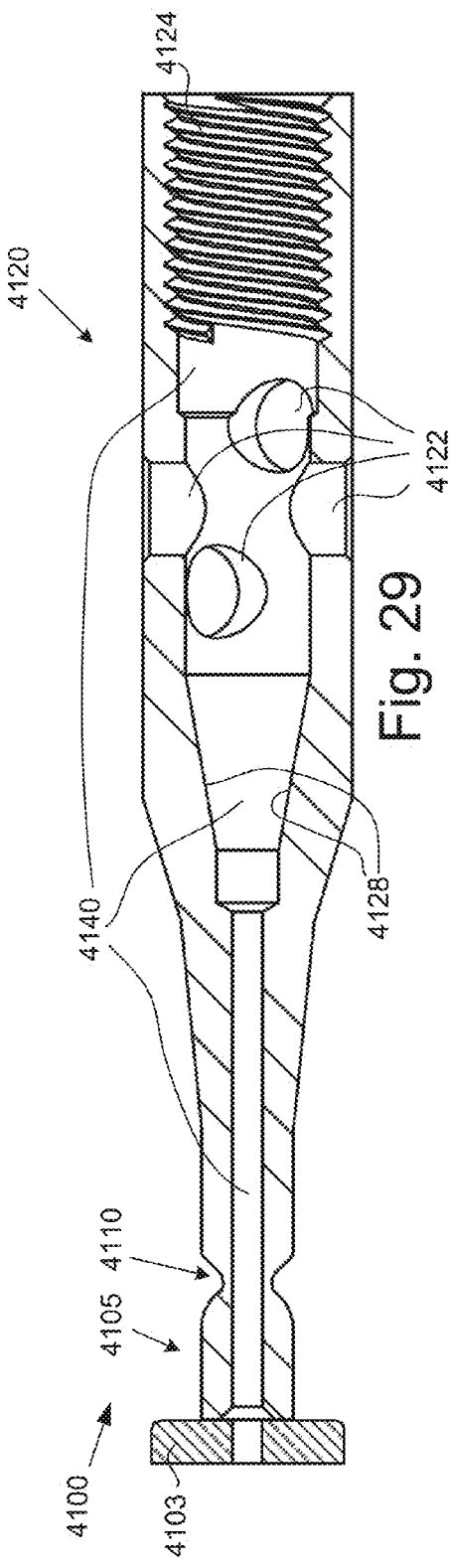

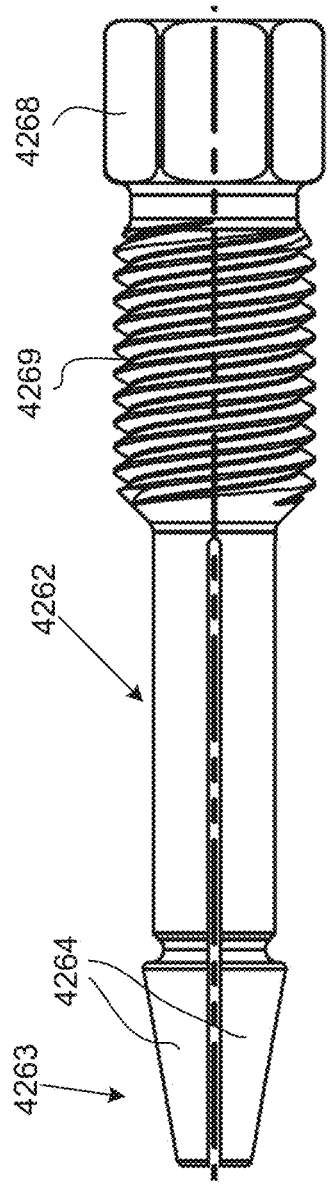
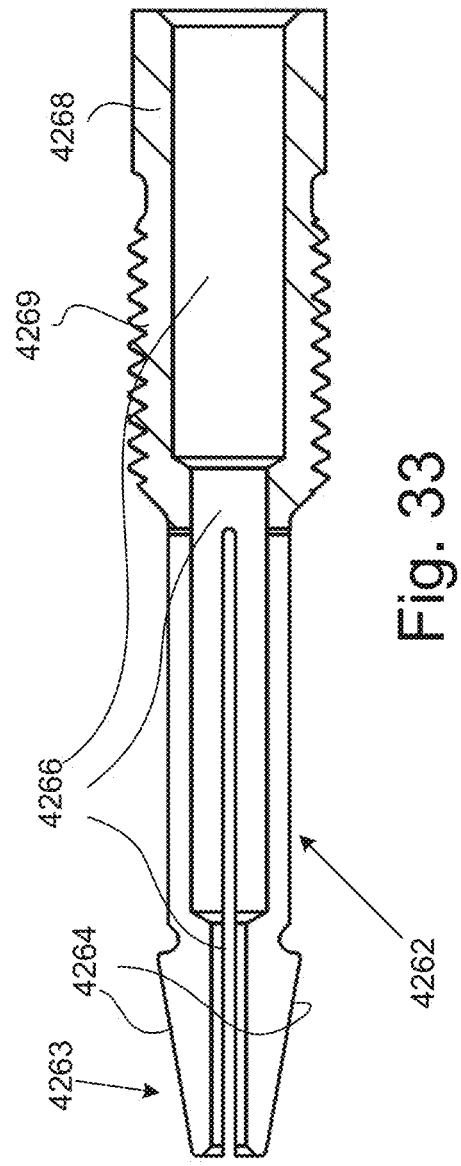

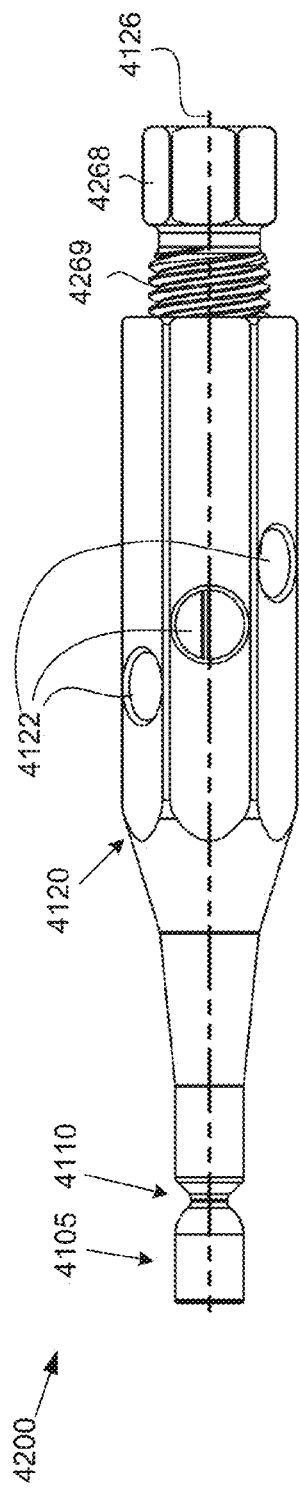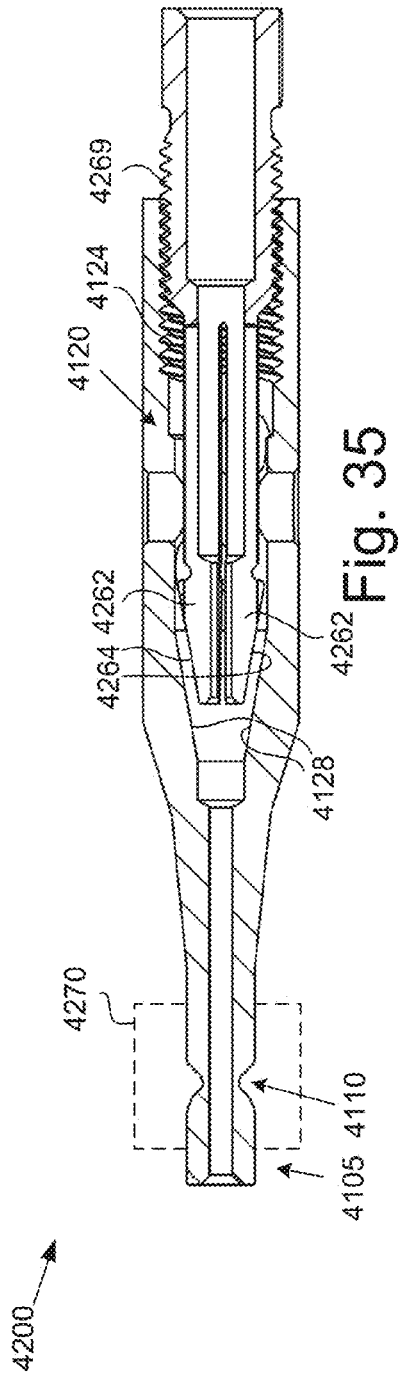

SYSTEM AND METHOD FOR REDUCING AND STABILIZING FRACTURES IN BONE, SUBLUXATIONS, OR DISLOCATIONS

FIELD

The subject matter of the present disclosure relates generally to reducing and stabilizing fractures in bone, subluxations of bones, dislocations of bones, and soft-tissue injuries, and more particularly relates to positioning and tensioning cables around bones and in holes in bone.

BACKGROUND

Various medical procedures utilize screws, pins, half pins, rods, wires, conventional sutures, and cables to secure damaged bone. For example, bones or soft-tissues that have been fragmented, fractured, broken, torn, pulled, stretched, or otherwise damaged need to be set and held in specific orientations in order to properly heal. Cables or conventional sutures may be useful for securing/attaching torn tissue back together or for facilitating holding bone fragments in place. For example, cerclage cables or conventional sutures can be wrapped around or lie adjacent to bone for fracture reduction, fracture fixation, and crack propagation prevention. However, conventional tools and procedures for utilizing cables or conventional sutures in medical surgeries are generally time-consuming, complex, and involve multiple in-situ steps that are difficult to perform.

SUMMARY

From the foregoing discussion, it should be apparent that a need exists for an apparatus, system, and method for bone fracture reduction, bone fracture fixation, bone crack propagation prevention, and soft-tissue stabilization that overcome the limitations of conventional medical tools and procedures. Beneficially, such an apparatus, system, and method would improve the ease, efficiency, and effectiveness of medical procedures for bone fracture reduction, bone fracture fixation, bone crack propagation prevention, and soft-tissue stabilization.

The subject matter of the present application has been developed in response to the present state of the art, and in particular, in response to the problems and needs in the art that have not yet been fully solved by currently available medical tools and procedures. For example, the ease, efficiency, and effectiveness of bone fracture reduction, bone fracture fixation, bone crack propagation prevention, and soft-tissue stabilization could be improved by supporting, redirecting, and/or fixating a tensioned cable relative to a hole in a bone or around the bone. Accordingly, the present disclosure has been developed to provide a system and method for supporting, redirecting, and/or fixating a tensioned cable relative to a hole in a bone or around the bone that overcome many or all of the above-discussed shortcomings in the art.

According to some embodiments, a first method, for reducing and stabilizing at least one of a fracture in, a dislocation of, and a subluxation of at least one bone, includes forming a hole in the at least one bone. The first method also includes anchoring a first portion of a cable relative to the at least one bone and positioning a second portion of the cable in the hole in the at least one bone. With the second portion of the cable positioned in the hole in the at least one bone, the method includes both tensioning the cable to a measurable and adjustable tension, to cause a measurable and adjustable compression of the bone by the cable in some implementations, and, with the cable tensioned to the measurable tension, anchoring a third portion of the cable relative to the at least one bone.

In certain implementations, the first method also includes re-tensioning the cable to a second measurable and adjustable tension. The first method may also include coupling the cable to an internal bone fixation device, an external bone fixation device, or both an internal and external bone fixation device in some implementations.

According to certain implementations of the first method, the hole is a pass-through hole that extends from a first side of the at least one bone to a second side of the at least one bone. Forming the pass-through hole in the at least one bone includes driving a hole-forming tool through the at least one bone. Positioning the second portion of the cable in the pass-through hole in the at least one bone includes passing a third portion through the pass-through hole in the at least one bone. Passing the third portion of the cable through the pass-through hole in the at least one bone can include coupling the third portion of the cable to the hole-forming tool and collectively pulling the hole-forming tool and the third portion of the cable through the pass-through hole. Forming the pass-through hole in the at least one bone may include driving a hole-forming tool through the at least one bone in a first direction from the first side of the at least one bone to form the pass-through hole until at least a first connection feature of the hole-forming tool protrudes from the pass-through hole on the second side of the at least one bone. Passing the third portion of the cable through the pass-through hole in the at least one bone can include, with the first connection feature of the hole-forming tool protruding from the pass-through hole on the second side of the at least one bone, coupling a second connection feature of the third portion of the cable to the first connection feature of the hole-forming tool and, after coupling the first and second connection features, withdrawing the hole-forming tool from the pass-through hole in a second direction opposite the first direction to pull the third portion of the cable through the pass-through hole such that at least the third portion of the cable protrudes from the pass-through hole on the first side of the at least one bone. Forming the pass-through hole in the at least one bone may include driving a hole-forming tool through the at least one bone in a first direction from the first side of the at least one bone to form the pass-through hole, and leaving at least a shank connection feature of the hole-forming tool protruding from the pass-through hole on the first side of the at least one bone. Passing the third portion of the cable through the pass-through hole in the at least one bone can include, with the shank connection feature of the hole-forming tool protruding from the pass-through hole on the first side of the at least one bone, coupling a second connection feature of the third portion of the cable to the shank connection feature of the hole-forming tool and, after coupling the shank and second connection features, withdrawing the hole-forming tool from the pass-through hole in the first direction to pull the cable through the pass-through hole such that the third portion of the cable protrudes from the pass-through hole on the second side of the at least one bone.

In some implementations of the first method, anchoring the first portion of the cable relative to the at least one bone includes driving an anchor into the at least one bone, wherein the first portion of the cable is fixed to the anchor.

According to yet some implementations of the first method, anchoring the first portion of the cable relative to the at least one bone includes releasably attaching a distal portion of a cable housing to an anchor. The first portion of the cable is fixed to the anchor. The cable housing includes a passage, and the second portion of the cable is non-fixedly positioned in the passage. The method further includes, after attaching the distal portion of the cable housing to the anchor, co-rotating the cable housing and the anchor to drive the anchor into a at least one bone. Additionally, the method includes, after driving the anchor into the at least one bone, withdrawing the cable housing away from the at least one bone to collectively detach the anchor from the cable housing and remove the second portion of the cable from the passage of the cable housing.

In some implementations, the first method includes passing the third portion of the cable from the pass-through hole in the at least one bone through a central passage continuously extending through a crimp body and an elongate shaft, wherein the crimp body is coupled to an end of the elongate shaft. The first method may also include using the elongate shaft to position the crimp body in a desired position relative to the pass-through hole in the at least one bone. The third portion of the cable extends from the pass-through hole into the central passage of the crimp body. Additionally, the first method includes, with the crimp body in the desired position and the cabled tensioned to the measurable and adjustable tension, crimping the crimp body about the third portion of the cable. Furthermore, the first method may include, after crimping the crimp body about the third portion of the cable, detaching the crimp body from the elongate shaft.

According to certain implementations, the first method additionally includes supporting a redirection of the third portion of the cable relative to the pass-through hole in the at least one bone after passing through the pass-through hole in the at least one bone with a washer positioned over the pass-through hole in the at least one bone.

According to some implementations, the first method further includes positioning a washer over the pass-through hole in the at least one bone such that a bone-engaging surface of the washer engages a surface of the at least one bone adjacent the pass-through hole. The first method can include passing the third portion of the cable through a pass-through aperture in the washer. The pass-through aperture extends in a first direction from the bone engaging surface to a cable-engaging surface. Also, the method can include positioning the third portion of the cable in a channel of the washer. The channel extends in a second direction that is at least one of non-parallel to and offset from the first direction.

In certain implementations, the first method further includes connecting the cable to a soft-tissue fixation device. The hole can be a uni-cortical hole and anchoring the first portion of the cable may include fixating the first portion of the cable within the uni-cortical hole via a fixation device positioned within the uni-cortical hole.

According to some implementations, the first method also includes coupling the third portion of the cable to an external fixation device. Tensioning the cable to the measurable and adjustable tension fixates the external fixation device relative to the at least one bone. The measurable and adjustable compression can be unidirectional.

In yet another embodiment, a second method, for reducing and stabilizing at least one of a fracture in, a dislocation of, and a subluxation of at least one bone, includes driving a hole-forming tool through the at least one bone to form a pass-through hole in the at least one bone. The pass-through hole extends from a first side of the at least one bone to a second side of the at least one bone. The second method further includes anchoring a first portion of a cable relative to the at least one bone, coupling a second portion of the cable to the hole-forming tool, and collectively pulling the hole-forming tool and the second portion of the cable through the pass-through hole. Additionally, the second method includes supporting a redirection of the second portion of the cable relative to the pass-through hole in the at least one bone after passing through the pass-through hole in the at least one bone with a washer positioned over the pass-through hole in the at least one bone. Also, the second method includes passing the second portion of the cable from the pass-through hole in the at least one bone through a central passage continuously extending through a crimp body and an elongate shaft. The crimp body is coupled to an end of the elongate shaft. The second method further includes using the elongate shaft to position the crimp body in a desired position relative to the pass-through hole in the at least one bone. The second portion of the cable extends from the pass-through hole into the central passage of the crimp body. The second method can additionally include tensioning the cable to a measurable and adjustable tension with a third portion of the cable positioned in the pass-through hole, to cause a measurable and adjustable compression of the at least one bone by the cable and, with the crimp body in the desired position and after tensioning the cable to the measurable and adjustable tension, crimping the crimp body about the second portion of the cable. Additionally, the second method includes, after crimping the crimp body about the second portion of the cable, detaching the crimp body from the elongate shaft.

According to some implementations, the second method further includes coupling the cable to an internal bone fixation device, an external bone fixation device, or both an internal and external bone fixation device. Anchoring the first portion of the cable relative to the at least one bone can include driving an anchor into the at least one bone, where the first portion of the cable is fixed to the anchor. The second method may also include connecting the cable to a soft-tissue fixation device.

In another embodiment, a system, for reducing and stabilizing at least one of a fracture in, a dislocation of, and a subluxation of at least one bone, includes a hole-forming tool configured to form a pass-through hole in the at least one bone. The hole-forming tool includes at least one of a first connection feature and a shank connection feature. The system also includes a cable configured to be positioned within and extend through the pass-through hole and be anchored relative to the at least one bone. The cable includes a second connection feature coupleable with at least one of the first connection feature and the shank connection feature of the hole-forming tool. Furthermore, the system includes a washer configured to support a redirection of the cable relative to the pass-through hole in the at least one bone. The washer includes a pass-through aperture extending in a first direction and a channel extending in a second direction non-perpendicular to the first direction. The cable is configured to extend from the pass-through hole into the pass-through aperture and be positioned in the channel. Additionally, the system includes a tensioner configured to tension the cable to a measurable and adjustable tension, to cause a measurable and adjustable compression of the at least one bone by the cable in some implementations, and a crimp apparatus that includes a central passage continuously extending through a crimp body and an elongate shaft. The crimp body is coupled to an end of the elongate shaft. The crimp apparatus is configured to crimp the crimp body about the cable to maintain the measurable and adjustable tension in the cable.

According to some implementations, the system also includes a cable housing and an anchor configured to be anchored in the at least one bone. The cable housing is detachably and co-rotatably engageable with the anchor and the cable is fixed to the anchor and non-fixedly positionable within the cable housing.

In certain implementations, the system further includes a soft-tissue fixation device having cable holes. The cable is configured to pass through the cable holes of the soft-tissue fixation device to connect a soft-tissue segment to the at least one bone. Also, the soft-tissue fixation device includes a first plate having a plurality of tines and a second plate. The first and second plates are configured to clamp around the soft-tissue segment with the plurality of tines extending through the soft-tissue segment. According to yet some implementations, the system additionally includes an internal bone fixation device, an external bone fixation device, or both an internal and external bone fixation device. The internal bone fixation device and external bone fixation device are configured to be coupled to the cable.

Reference throughout this specification to features, advantages, or similar language does not imply that all of the features and advantages that may be realized with the present disclosure should be or are in any single embodiment of the disclosure. Rather, language referring to the features and advantages is understood to mean that a specific feature, advantage, or characteristic described in connection with an embodiment is included in at least one embodiment of the subject matter disclosed herein. Thus, discussion of the features and advantages, and similar language, throughout this specification may, but do not necessarily, refer to the same embodiment.

Furthermore, the described features, advantages, and characteristics of the disclosure may be combined in any suitable manner in one or more embodiments. One skilled in the relevant art will recognize that the subject matter of the present application may be practiced without one or more of the specific features or advantages of a particular embodiment. In other instances, additional features and advantages may be recognized in certain embodiments that may not be present in all embodiments of the disclosure. Further, in some instances, well-known structures, materials, or operations are not shown or described in detail to avoid obscuring aspects of the subject matter of the present disclosure. These features and advantages of the present disclosure will become more fully apparent from the following description and appended claims, or may be learned by the practice of the disclosure as set forth hereinafter.

BRIEF DESCRIPTION OF THE DRAWINGS

In order that the advantages of the disclosure will be readily understood, a more particular description of the disclosure briefly described above will be rendered by reference to specific embodiments that are illustrated in the appended drawings. Understanding that these drawings depict only typical embodiments of the disclosure and are not therefore to be considered to be limiting of its scope, the subject matter of the present application will be described and explained with additional specificity and detail through the use of the accompanying drawings, in which:

FIG. 5A is a perspective view of a distal portion of the cable housing, according to one embodiment;

FIG. 5B is a perspective view of a shank of an anchor, according to one embodiment;

FIG. 6 is a perspective view of a proximal portion of the cable housing, with a detachable cap detachably engageable to the cable housing, according to one embodiment;

FIG. 7 is a perspective view of the cable housing, according to one embodiment;

FIG. 9A is an exploded perspective view of an apparatus for passing cable through a pass-through hole (e.g., a tunnel) in bone, with a first connection feature of a hole-forming tool being coupleable with a cable, according to one embodiment;

FIG. 9B is a partial perspective view of the apparatus, showing the hole-forming tool having a shank connection feature that is coupleable with the cable, according to one embodiment;

FIG. 13A is a perspective view the first connection feature of the hole-forming tool, according to one embodiment;

FIG. 13B is a side view of the first connection feature of the hole-forming tool, according to one embodiment;

FIG. 28 is a side view of the apparatus of FIG. 27, but with a washer disposed adjacent the crimp body, according to one embodiment;

FIG. 29 is a cross-sectional side view of the apparatus of FIG. 28, according to one embodiment;

FIG. 32 is a side view of the collet member of FIG. 31, according to one embodiment;

FIG. 33 is a cross-sectional side view of the collet member of FIG. 32, according to one embodiment;

FIG. 34 is a side view of the apparatus of FIG. 30, according to one embodiment;

FIG. 35 is a cross-sectional side view of the apparatus of FIG. 30, according to one embodiment;

DETAILED DESCRIPTION

Figure 1:
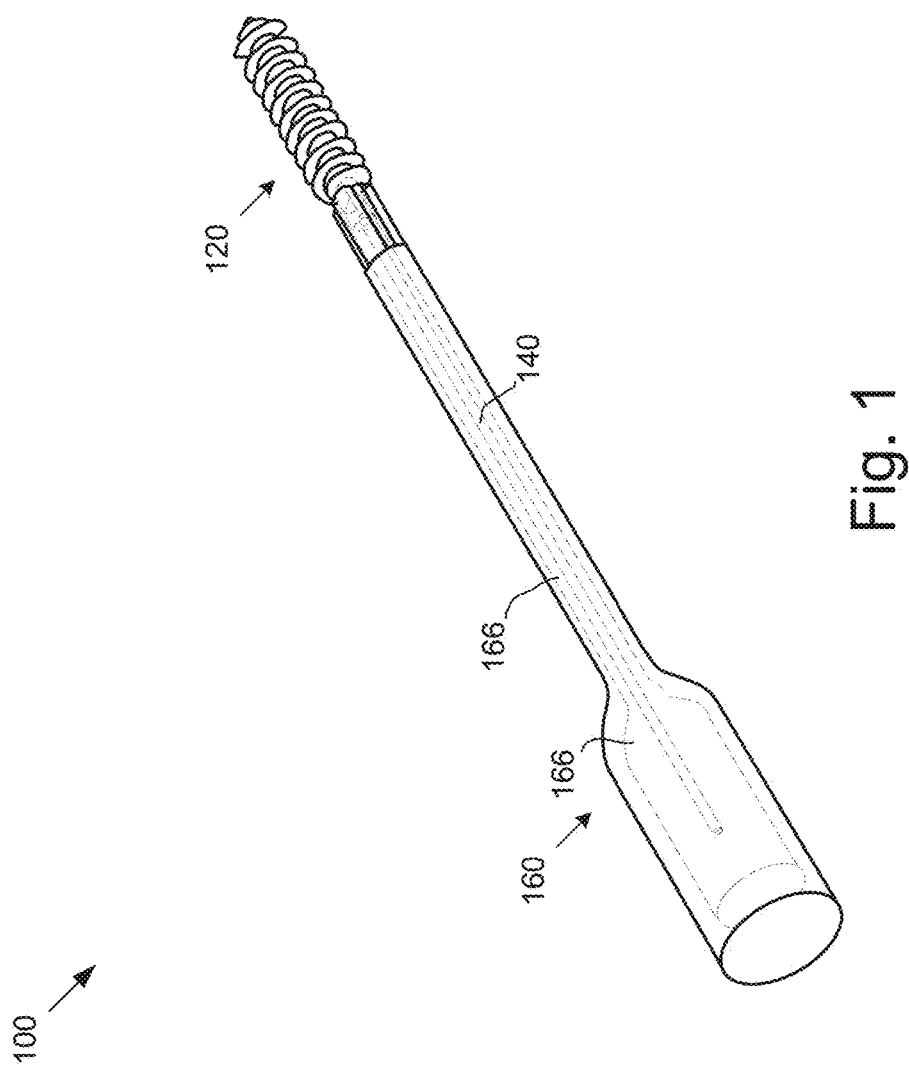
FIG. 1 is a perspective view of an apparatus for anchoring cable to bone, with a cable positioned within a passage of a cable housing, according to one embodiment.

Reference throughout this specification to "one embodiment," "an embodiment," or similar language means that a particular feature, structure, or characteristic described in connection with the embodiment is included in at least one embodiment of the present disclosure. Thus, appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

In the following description, numerous specific details are provided. One skilled in the relevant art will recognize, however, that the subject matter of the present application may be practiced without one or more of the specific details, or with other methods, components, materials, and so forth. In other instances, well-known structures, materials, or operations are not shown or described in detail to avoid obscuring aspects of the disclosure.

Anchoring Cable to Bone

Illustrated in FIGS. 1-7 are several representative embodiments of an apparatus 100 for anchoring cable to bone. As described herein, the apparatus for anchoring cable to bone provides various advantages and benefits over other medical tools and procedures. However, the recited advantages are not meant to be limiting in any way, as one skilled in the art will appreciate that other advantages may also be realized upon practicing the present disclosure.

FIGS. 1-4 are perspective views of the apparatus 100 for anchoring cable to bone. The apparatus 100 includes an anchor 120, a cable 140, and a cable housing 160. The anchor 120 has a threaded portion 122 and a shank 124. The cable 140 has a fixed-end portion 142 and a free-end portion 144. The cable housing 160 has a distal portion 162, a proximal portion 164, and a passage 166. The shank 124 of the anchor 120 is detachably and co-rotatably engageable with the distal portion 162 of the cable housing 160. Also, the fixed-end portion 142 of the cable 140 is fixedly coupled to the shank 124 of the anchor 120 while the free-end portion 144 of the cable 140 is non-fixedly positioned in the passage 166 of the cable housing 160.

The cable housing is at least partially hollow. In one embodiment, the passage 166 is a central chamber of the at least partially hollow cable housing 160. In another embodiment, the passage is not centrally located in the cable housing but instead is offset from center. As shown in FIG. 5, the passage 166 is open to and extends from a distal opening 161 at the distal end 168 of the distal portion 162 of the cable housing 160.

The cable housing 160 and the anchor 120 are detachably and co-rotatably coupled together so that rotation of the cable housing 160 causes the anchor 120 to also rotate. In other words, the cable housing 160 and the anchor 120 are coupleable to co-rotate together. A practitioner may engage the proximal portion 164 of the cable housing 160, either manually using a hand tool or indirectly using a power tool, to rotate the cable housing 160. Accordingly, the cable housing may include external engagement features, either disposed on the surface of the proximal portion 164 (e.g., hexagonal nut feature) or disposed on the proximal end 169 (e.g., chuck feature, shank feature, etc.) of the cable housing 160. When a practitioner engages the external engagement feature, the cable housing 160 and the anchor are co-rotatably coupled together and rotation of the cable housing 160 causes the anchor 120 to also rotate.

Figure 2:
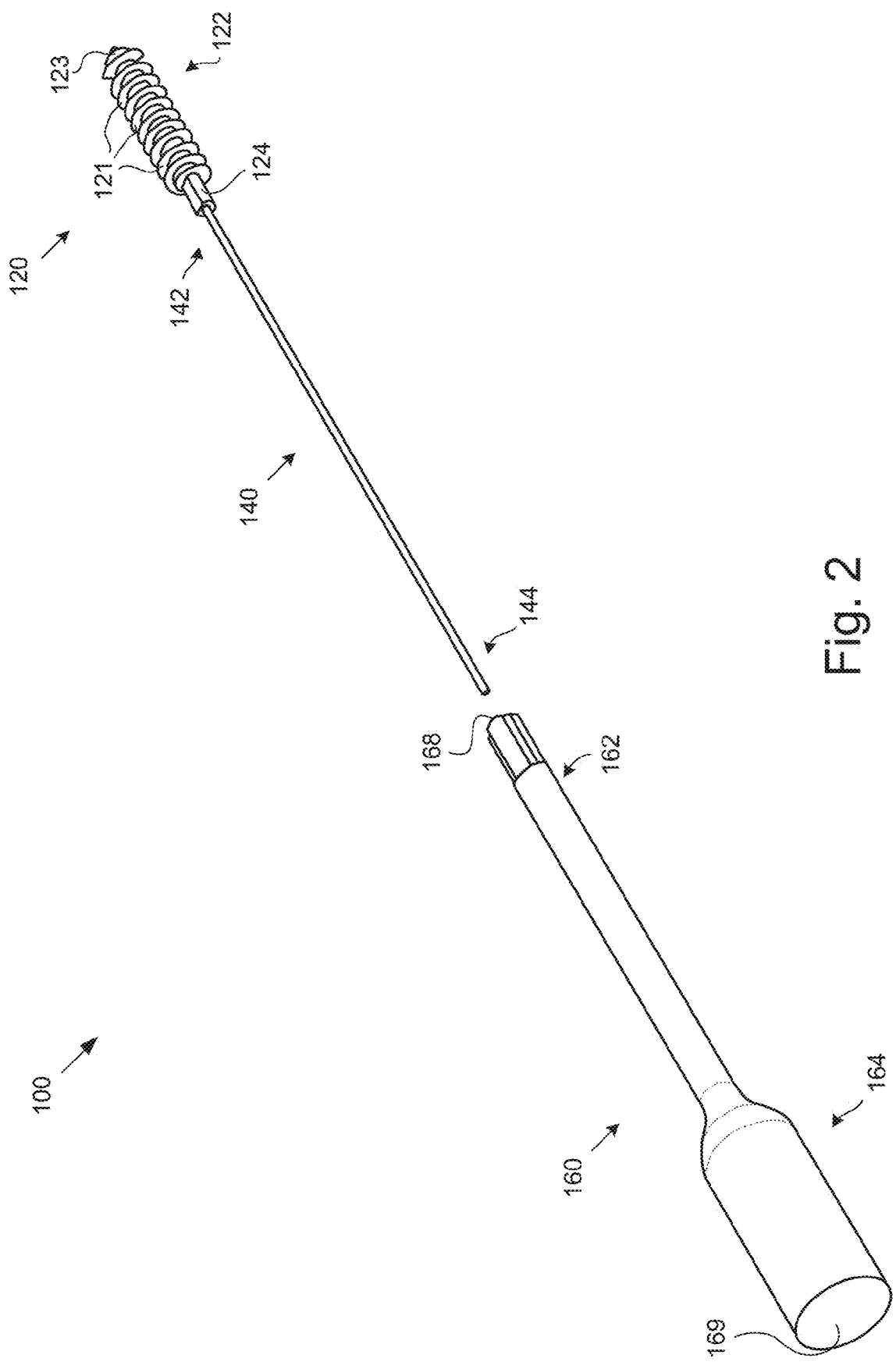
FIG. 2 is a perspective view of the apparatus of FIG. 1 but with the cable withdrawn from the passage of the cable housing, according to one embodiment.
Figure 3:
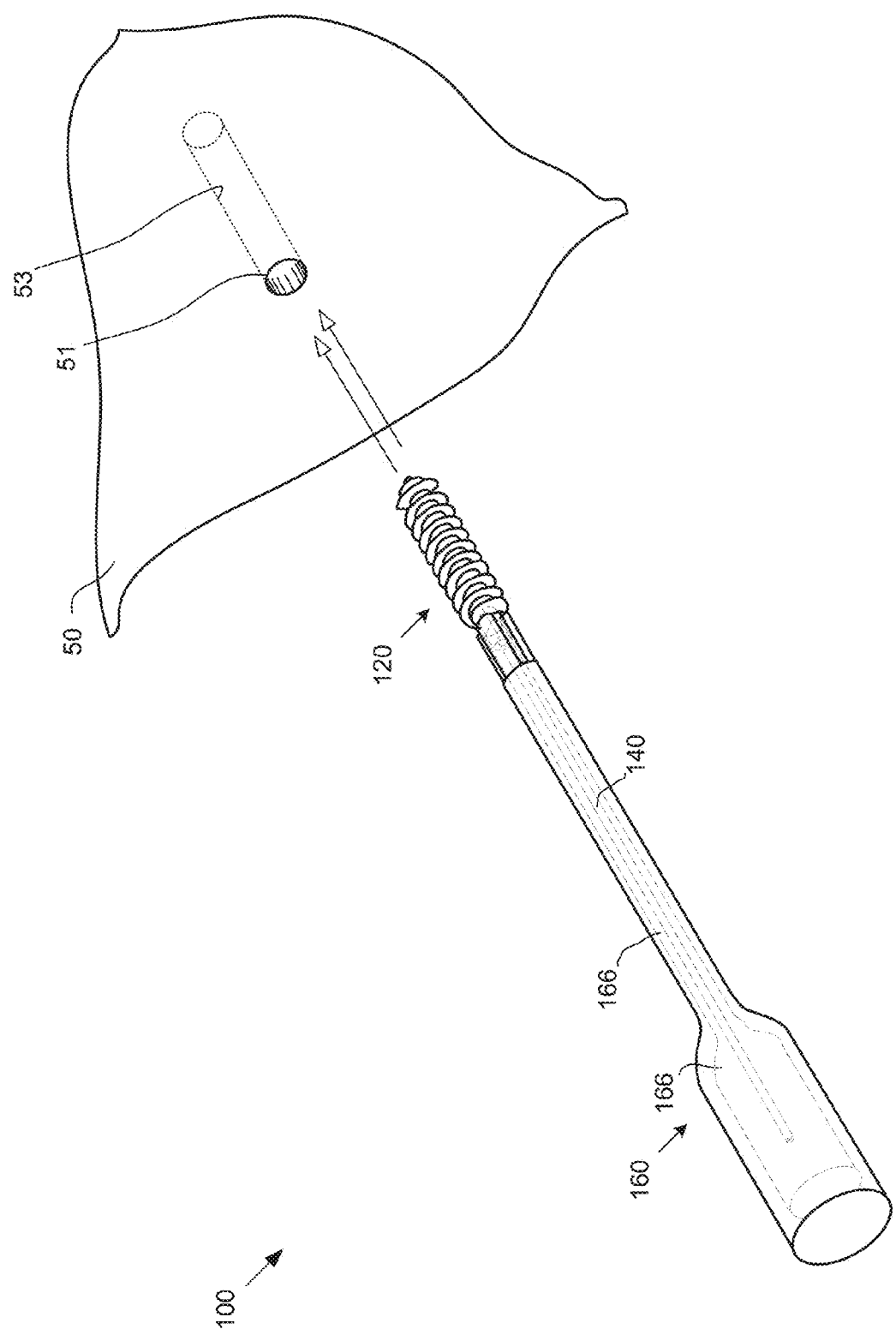
FIG. 3 is a perspective view of the apparatus before installing an anchor into a hole in a bone, according to one embodiment.
Figure 4:
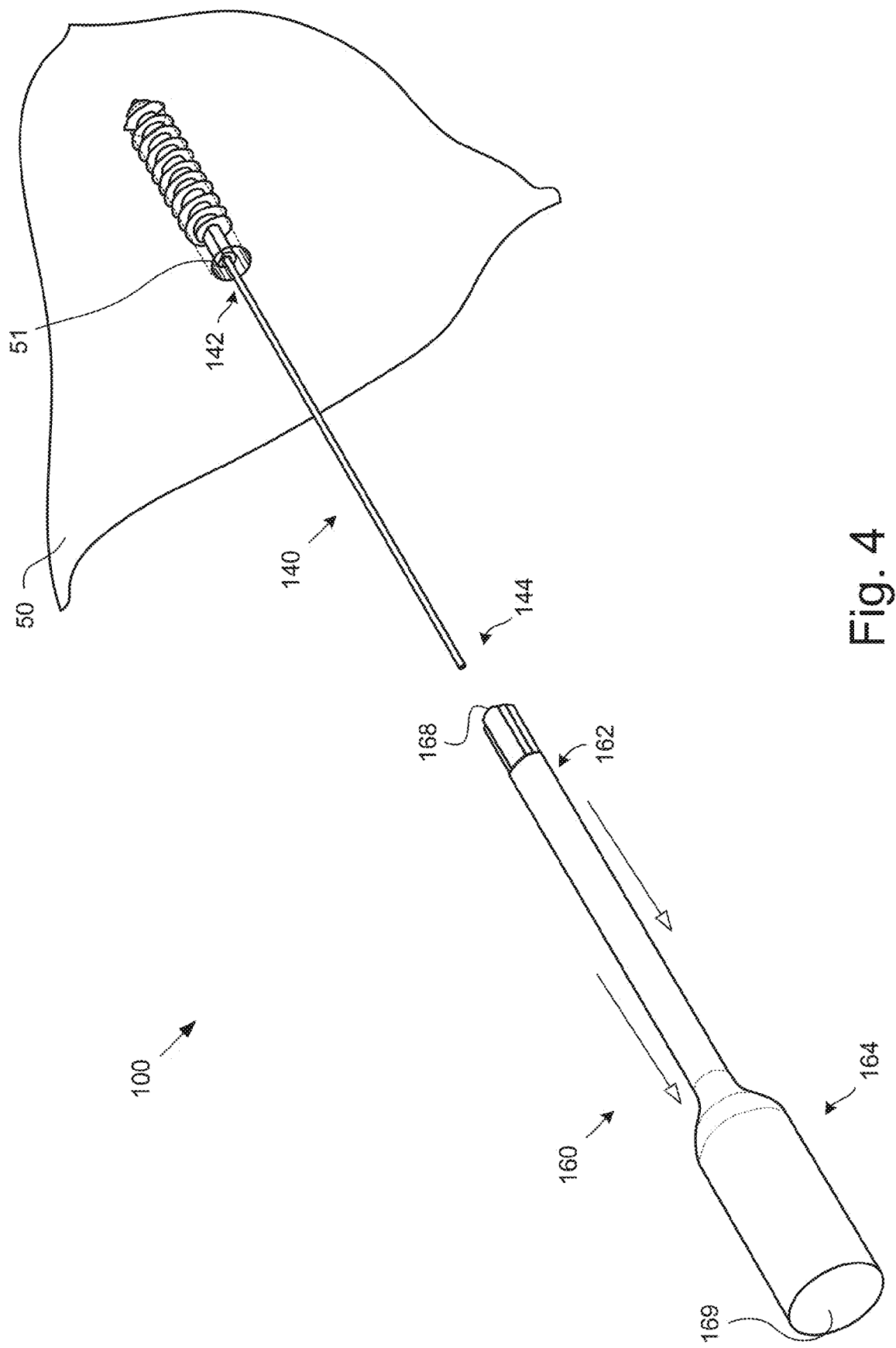
FIG. 4 is a perspective view of the apparatus, with the anchor secured to the bone and the cable withdrawn from the passage of the cable housing, according to one embodiment.

As shown in FIG. 2, the threaded portion 122 of the anchor 120 includes a cutting portion 123 and a plurality of external threads 121. The cutting portion 123 of the anchor 120 cuts into bone 50 as the anchor 120 rotates. In one embodiment, as depicted in FIGS. 3 and 4, the bone 50 already has a preformed hole 51 and the anchor 120 can be secured to the bone by being driven into the pilot hole 51 so that the external threads 121 securely engage the bone 50. In another embodiment, the bone does not have a pre-drilled hole and the cutting portion 123 of the anchor 120 drills and cuts into the bone 50 with the threads securely embedding in the side 53 of the hole 51 in the bone 50.

As described above, the fixed-end portion 142 of the cable 140 is permanently fixed to the shank 124 of the anchor 120 while the free-end portion 144 is positionable within the passage 166 of the cable housing 160. Once the anchor 120 has been securely anchored/embedded within the bone 50 by co-rotating the cable housing 160 and the anchor 120, the cable housing 160 may be detached from the shank 124 of the anchor 120 and the cable housing 160 may be withdrawn from the bone 50, thereby exposing the free-end portion 144 of the cable 140. The free-end portion 144 of the cable 140 can be used in a medical procedure or a surgery to hold skeletal tissue or soft-tissue in a desired position to allow the body of a patient to properly heal. For example, the cable 140 may be wrapped and tensioned around bone or soft-tissue, similar to a cerclage wire configuration. In another implementation, the free-end portion 144 of the cable 140 may be inserted through a through-hole (e.g., a tunnel, passage, or passageway) in a bone. Further, the cable 140 may be tensioned to a measurable and adjustable tension in order to facilitate reducing and stabilizing bone fractures or to facilitate the repair of dislocations or soft-tissue damage. In some implementations, tensioning the cable 140 to a measurable and adjustable tension causes a measurable and adjustable compression of the bone by the cable.

The anchor 120 may be made from stainless steel or titanium. In another embodiment, the anchor 120 may be made from low carbon steel, high carbon steel, high speed steel, cobalt steel alloys, tungsten carbide, and polycrystalline diamond, among other materials. In a further embodiment, the anchor 120 may be made from a ceramic material or a bio-absorbable material. The anchor 120 may also have one or more coatings to prevent corrosion, or improve the cutting and anchoring performance of the anchor 120. The coating, which may be antimicrobial, may also be useful to decrease the likelihood of toxicity and infection in the bone tissue.

According to one embodiment, the term "cable" refers to a cord-like element, such as a wire, filament, weave, or thread, whether bundled or individual, that is capable of holding a measurable and adjustable tension and causing a measurable and adjustable compression of bone. In other words, the tension in the cable can be measured, such as by a tension measuring device, and can be adjusted, such as after an initial tensioning of the cable. When used to compress bone (e.g., to compress two bone segments together), the measured tension in the cable is equal to a measured compression of the bone. Thus, as used herein, a measured and adjustable tension of a cable is synonymous with a measured and adjustable compression of bone by the cable.

In one embodiment, the measurable and adjustable tension may be a specific, known, predictable, expected, controllable, anticipated, desired, repeatable, sustainable, and/or adjustable tension. For example, the cable 140 may be passed through a pass-through hole in a bone and may be tensioned to a measurable and adjustable tension in order to facilitate the reduction and fixation of fractures or to otherwise facilitate the repair of dislocations or soft-tissue damage. In other words, the cable 140 is not a conventional suture or conventional thread material, since such materials are incapable of, or at least not well-suited for, maintaining a measurable and adjustable tension. Thus, the term "cable" refers to a flexible yet substantially non-stretchable element that can be tensioned to a measurable and adjustable tension. In such an embodiment, because the cable 140 is capable of maintaining or retaining a measurable and adjustable tension, the effectiveness and reproducibility of successful surgical procedures is improved. In other words, different surgical procedures relating to different bones in the body may involve different degrees of retention/fixation force (e.g., the fixation force required to reduce a fracture in the femur may be greater than the fixation force required to reduce a fracture in the patella). Accordingly, the ability of the cable 140 to be tensioned to a measurable and adjustable tension improves the reliability and reproducibility of surgical procedures when compared with other medical procedures that do not utilize cables. The cable 140 may be made from any one of various materials. For example, in specific implementations, the cable 140 is made from metal, such as stainless steel, titanium, or other metal.

The cable housing 160 may be made from various materials, including metals such as stainless steel and synthetics such as a rigid plastic, polymer, or composite. In one embodiment, the cable housing 160 is disposable. In another embodiment, the cable housing 160 may be sterilized, a new cable 140 may be loaded into the passage 166, and the cable housing 160 may be re-used. In one embodiment, as depicted in the figures, the proximal portion 164 of the cable housing 160 may have a comparatively larger external cross-sectional dimension than the distal portion 162 of the cable housing 160. However, in another embodiment, the cable housing 160 may have an external cross-sectional dimension that is substantially uniform along the entire length of the cable housing 160. Further, while the cross-sectional shape of the cable housing 160 is depicted as having a circular cross-sectional shape (e.g., a cylindrical), in other embodiments the cable housing 160 may have a rectangular or polygonal cross-sectional shape. Additional details regarding the anchor 120, the cable 140, and the cable housing 160 of the apparatus 100 are included below with reference to the remaining figures.

FIG. 5A is a distal perspective view of the distal portion 162 of the cable housing 160 and FIG. 5B is a proximal view of the shank 124 of the anchor 120. As mentioned above, the cable housing 160 is detachably and co-rotatably engageable with the anchor 120. In the embodiment depicted in FIGS. 5A and 5B, the shank 124 has a non-circular outer-periphery 126 that is engageable with a complementary non-circular interior surface 176 of the passage 166 at the distal portion 162 of the cable housing 160. In other words, the shank 124 of the anchor 120 is at least partially receivable through the distal opening 161 at the distal end 168 of the distal portion 162 of the cable housing 160 so that the shank 124 engages the interior surface 176 of the passage 166.

The non-circular but respectively conforming or complementary shape of the shank 124 of the anchor 120 and the distal portion 162 of the cable housing 160 enables the co-rotation of the two components 120, 160. In another embodiment, the detachable and co-rotatable engagement between the anchor 120 and the cable housing 160 may be accomplished using other configurations. For example, a tongue and groove configuration or a pin and bore configuration, among others, may be implemented to form the engagement between the anchor 120 and the cable housing 160.

The fixed-end portion 142 of the cable 140 is permanently coupled to the anchor 120. In one embodiment, the fixed-end portion 142 of the cable 140 may be inserted into a bore 175 in the shank 124 of the anchor 120. The fixed-end portion 142 of the cable 140 may be crimped, glued, welded, or otherwise fixed to the shank 124 of the anchor 120.

According to the embodiment depicted in FIG. 5A, the distal portion 162 of the cable housing 160 includes cutting features 178. The cutting features 178 are configured to counter-sink the bone. In one embodiment, at least a section of the distal portion of the cable housing may have a cross-sectional dimension that is small enough to fit within the hole 51, thus allowing the anchor 120 to be driven to a desired depth within the bone 50. In another embodiment, the cable housing 160 may include a flange or other stop-feature that prevents too much of the cable housing 160 from entering the hole 51, thus effectively restricting the depth of the anchor 120 within the bone 50.

FIG. 6 is a perspective view of the proximal portion 264 of the cable housing 260 with a cap 180 detachably engageable with the cable housing 260. As shown in the depicted embodiments, the cable housing 260, in addition to the distal opening 161 at the distal end 168, also has a proximal opening 271 at the proximal end 269 of the proximal portion 264. In other words, the passage 266 extends longitudinally within the cable housing 260 and has a proximal opening 271 at the proximal end 269 and a distal opening 161 at the distal end 168. The proximal portion 264 of the cable housing 260 may also have internal threads 267 that are threadably engageable with external threads 182 of the cap 180. As shown, the cap 180 may also include a connection feature (e.g., shank) 184 that is engageable/mateable with a driving tool or other surgical tool for driving the rotation of the cable housing 260.

In one embodiment, the loading of the cable 140 into the passage 266 may be facilitated by the cap 180. For example, connecting the cap 180 to cover the proximal opening 271 may securely hold the free-end portion 144 of the cable 140 within the passage. In one embodiment, the free-end portion 144 of the cable 140 is coiled within the passage 266.

FIG. 7 is a perspective view of one embodiment of the cable housing 360 showing the passage 366 having a proximal section 374 and a distal section 372. As described above, the external cross-sectional dimension of the cable housing may change along the length of the cable housing, according to the specifics of a given use. For example, the external dimensions of the cable housing 160 may be selected based on the type of driving tool used and/or the insertion depth of the anchor within the bone, among other considerations. Similarly, according to the embodiment shown in FIG. 7, the interior dimensions of the passage 366 may vary along the length of the passage 366. For example, the cable 140 may be coiled or otherwise packed within the proximal section 374 of the passage 366. The distal section 372 of the passage 366 may be configured to have an internal dimension that is just larger than the external diameter of the cable 140.

Figure 8:
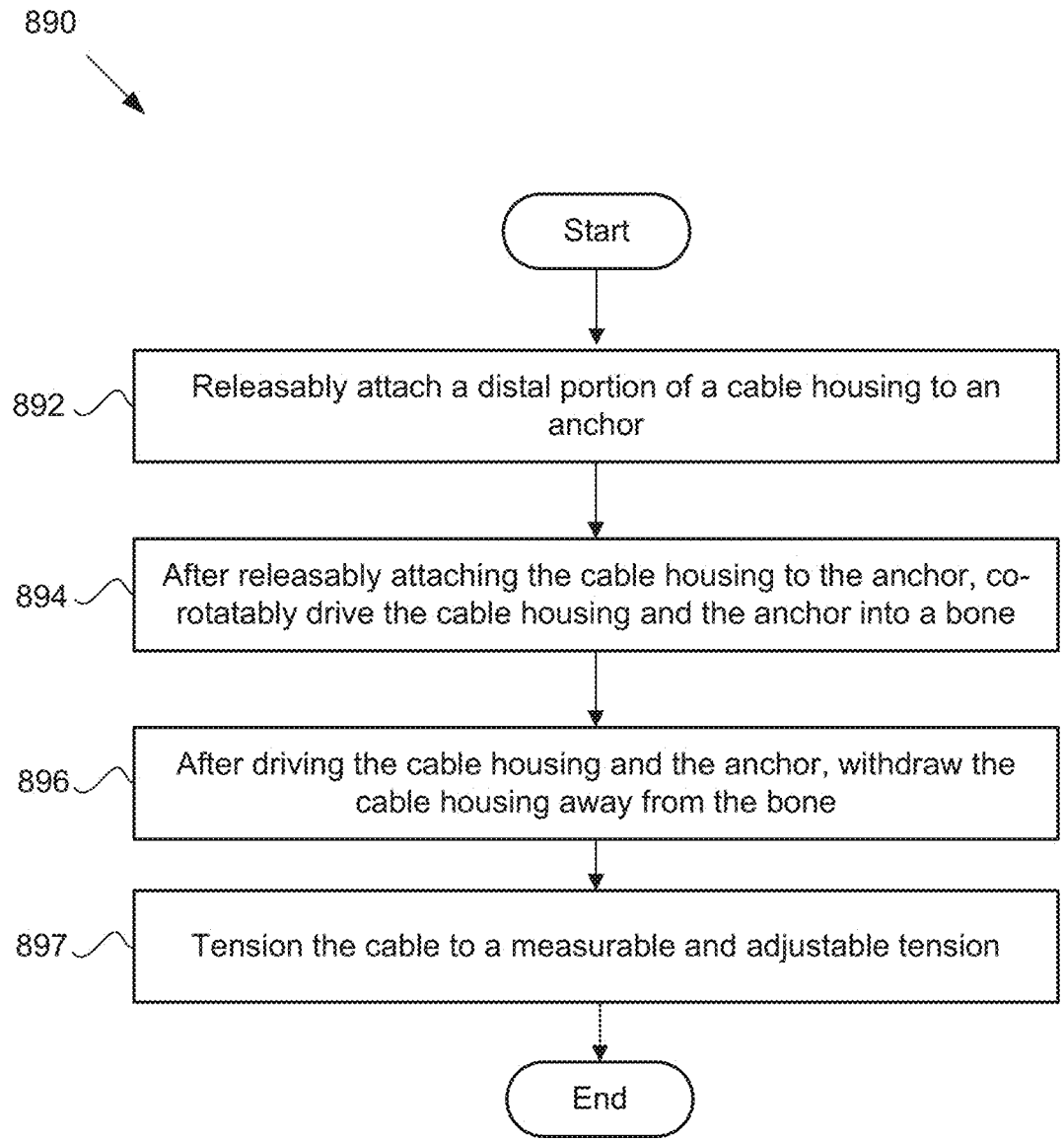
FIG. 8 is a schematic flowchart diagram of a method for anchoring cable to bone, according to one embodiment.

FIG. 8 is a schematic flowchart diagram of one embodiment of a method 890 for anchoring the cable 140 to bone 50. Generally, the method 890 includes at least partially embedding an anchor in bone and tensioning a cable, fixedly attached to the anchor, to a measurable and adjustable tension to cause, in some implementations, a measurable and adjustable compression of the bone by the cable. The cable can be pre-attached to the anchor prior to embedding the anchor in bone, or attached to the anchor after the anchor is embedded in bone. In specific implementations, the method 890 includes releasably attaching the distal portion of the cable housing to the anchor at 892. Attaching the cable housing to the anchor may involve engaging the non-circular outer-periphery of the shank of the anchor with the non-circular inner surface of the distal portion of the cable housing. The fixed-end portion of the cable is fixed to the anchor and the free-end portion of the cable is non-fixedly positioned in the passage. After attaching the distal portion of the cable housing to the anchor, the method 890 includes co-rotating the cable housing and the anchor to drive the anchor into a bone at 894. Driving the anchor into the bone at 894 can be performed with or without a pilot hole. Subsequently, the method 890 includes withdrawing the cable housing away from the bone to collectively detach the anchor from the cable housing and remove the cable from the passage of the cable housing at 896. The method 890 further includes tensioning the cable to a measurable and adjustable tension at 897, which may occur after withdrawing the cable housing at 896. According to an optional step of the method 890, after the cable is tensioned to a measurable and adjustable tension, the method can include releasing the tension in the cable and re-tensioning the cable to the same or different measurable and adjustable tension. Releasing the tension in the cable may include unlocking a lock that is configured to maintain the cable in tension. The ability to release tension in a cable and subsequently re-tension the cable provides various advantages, such as, for example, facilitating re-use of the cable on other targeted areas of the body in one or more subsequent procedures, in some implementations, and adjustment to the tension or position of the cable on the same targeted area of the body in the same or a subsequent procedure, in other implementations.

In one embodiment, co-rotating the cable housing and the anchor at 894 includes mating the proximal portion of the cable housing with a driving tool and actuating the driving tool to drive the anchor into the bone. In another embodiment, co-rotating the cable housing and the anchor at 894 further includes counter-sinking the bone with the cutting features disposed on the external surface of the distal portion of the cable housing. In another embodiment, before co-rotating the cable housing and the anchor at 894, the method 890 includes loading the cable into the passage of the cable housing. In yet another embodiment, the method 890 includes co-rotating the cable housing and the anchor in an opposite direction to remove the anchor from the bone. The method 890 may further include wrapping the cable around the bone before tensioning the cable. In another embodiment, the method 890 may include passing the cable through a pass-through hole in bone before tensioning the cable. In yet another embodiment, the method 890 may include passing the cable through a cable hole of a soft-tissue fixation device.

Passing Cable Through Hole in Bone

Illustrated in FIGS. 9A-13B are several representative embodiments of an apparatus 1100 for passing cable through bone. As described herein, the apparatus for passing cable through bone provides various advantages and benefits over other medical tools and procedures. However, the recited advantages are not meant to be limiting in any way, as one skilled in the art will appreciate that other advantages may also be realized upon practicing the present disclosure.

FIG. 9A is an exploded perspective view of the apparatus 1100 for passing cable through a pass-through hole (e.g., a tunnel) in bone. The apparatus 1100 includes a hole-forming tool 1120 and a cable 1140 coupleable to the hole-forming tool 1120. Generally, the hole-forming tool 1120 facilitates the formation of a pass-through hole in a bone. As defined herein, the hole-forming tool 1120 is any type of tool or device that can be used to form a hole in bone, such as, for example, a drilling tool (e.g., drill bit), a reaming tool, a cutting tool, or the like. Once the pass-through hole has been formed, the practitioner can couple the cable 1140 to the hole-forming tool and pull the hole-forming tool and cable through the hole. The apparatus 1100 eliminates the need to use both a drilling tool and a cable-passing tool.

The hole-forming tool 1120 has a shank 1121, a cutting portion 1122, and a first connection feature 1124. The cutting portion 1122 is interposed between the shank 1121 and the first connection feature 1124. In one embodiment, as shown in FIG. 9A, the hole-forming tool 1120 includes a non-cutting portion 1126 interposed between the shank 1121 and the cutting portion 1122. In another embodiment, the cutting portion 1122 extends substantially along an entire length between the shank 1121 and the first connection feature 1124. The shank 1121 is detachably coupleable to a driving tool, such as a power drill. The cable 1140 has a first-end portion 1141 and a second-end portion 1142. The first-end portion 1141 of the cable 1140 has a second connection feature 1144. The hole-forming tool 1120 is coupleable to the cable 1140 via the respective first and second connection features 1124, 1144. According to the embodiment shown in FIG. 9A, the hole-forming tool 1120 can be directly coupled to the cable 1140 via direct engagement between the first and the second connection features 1124, 1144. However, in an alternative embodiment, a coupler 1160 may be interposed between the hole-forming tool 1120 and the cable 1140 to facilitate the connection between the hole-forming tool 1120 and the cable 1140, as described in greater detail below with reference to FIG. 12. The coupler 1160 has a proximal-end portion 1161 and a distal-end portion 1162. The proximal-end portion 1161 has a third connection feature 1164 and the distal-end portion 1162 has a fourth connection feature 1166.

FIG. 9B is a partial perspective view of another embodiment of a hole-forming tool 1220. According to the embodiment shown in FIG. 9B, the shank 1221 of the hole-forming tool 1220 has a shank connection feature 1219 that is also coupleable with the cable 1140 via the second connection feature 1144. In other words, FIG. 9B shows an alternative shank 1221 that may be implemented with the apparatus 1100 depicted in FIG. 9A (i.e., shank 1221 replaces shank 1121). The shank 1221 is interposed between the shank connection feature 1219 and the cutting portion 1122. In such an implementation, as will be described in greater detail below with reference to FIGS. 11A and 11B, the cable 1140 may be coupled to the hole-forming tool on either end, thus allowing the cable to be pulled through the bone in either direction.

The hole-forming tool 1120 may be made from stainless steel or titanium. In another embodiment, the hole-forming tool 1120 may be made from low carbon steel, high carbon steel, high speed steel, cobalt steel alloys, tungsten carbide, and polycrystalline diamond, among other materials. The hole-forming tool 1120 may also have one or more coatings to prevent corrosion, or improve the cutting performance of the hole-forming tool 1120. The coating, which may be antimicrobial, may also be useful to decrease the likelihood of toxicity and infection in the bone tissue.

The shank 1121 may be shaped and configured according to a specific chuck of a drilling tool. For example, the shank 1121 may have a non-circular outer-periphery that can be received within a complimentary non-circular inner surface of a drill. In another embodiment, the shank may have a polygonal outer-periphery. In yet another embodiment, the shank may be cylindrical and the chuck of the drill may have sufficient clamping power to securely hold the shank and induce rotation of the hole-forming tool. The spiral, point angle, lip angle, and length of the cutting portion 1122 of the hole-forming tool 1120 may be selected according to the specifics of a given surgical procedure.

As defined herein, the term "cable" refers to a cord-like element, such as a wire, filament, weave, or thread, whether bundled or individual, that is capable of holding a measurable and adjustable tension and causing a measurable and adjustable compression of bone. In other words, the tension in the cable can be measured, such as by a tension measuring device, and can be adjusted, such as after an initial tensioning of the cable. When used to compress bone (e.g., to compress two bone segments together), the measured tension in the cable is equal to a measured compression of the bone. Thus, as used herein, a measured and adjustable tension of a cable is synonymous with a measured and adjustable compression of bone by the cable.

In one embodiment, the measurable and adjustable tension may be a specific, known, predictable, expected, controllable, anticipated, desired, repeatable, sustainable, and/or predeterminable tension. For example, the cable 1140 may be passed through a pass-through hole in a bone and may be tensioned to a measurable and adjustable tension in order to facilitate the reduction and fixation of fractures or to otherwise facilitate the repair of dislocations or soft-tissue damage. In other words, the cable 1140 is not a conventional suture or conventional thread material, since such materials are incapable of, or at least not well-suited for, maintaining a measurable and adjustable tension. Thus, the term "cable" refers to a flexible yet substantially non-stretchable element that can be tensioned to a measurable and adjustable tension. Because the cable 1140 is capable of maintaining or retaining a measurable and adjustable tension, the effectiveness and reproducibility of successful surgical procedures is improved. In other words, different surgical procedures relating to different bones in the body may involve different degrees of retention/fixation force (e.g., the fixation force required to reduce a fracture in the femur may be greater than the fixation force required to reduce a fracture in the patella). Accordingly, the ability of the cable 1140 to be tensioned to a measurable and adjustable tension improves the reliability and reproducibility of surgical procedures when compared with other medical procedures that do not utilize cables. The cable 1140 may be made from any one of various materials. For example, in specific implementations, the cable 1140 is made from metal, such as stainless steel, titanium, or other metal.

Figure 10:
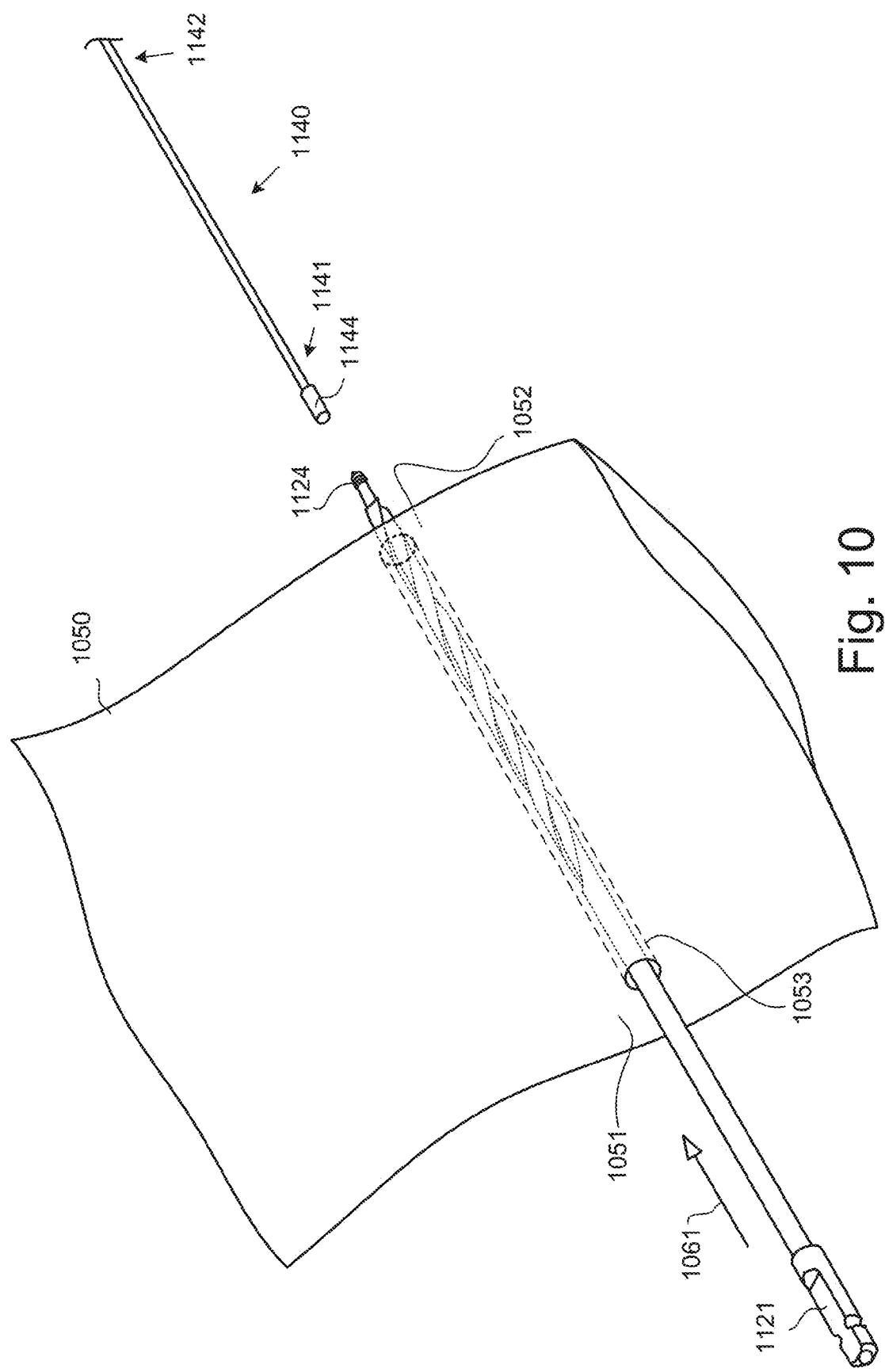
FIG. 10 is a perspective view of the hole-forming tool extending in a first direction through a pass-through hole in a bone, according to one embodiment.

FIG. 10 shows the hole-forming tool 1120 extending in a first direction 1061 through a pass-through hole 1053 in a bone 1050. The hole-forming tool 1120 extends from a first side 1051 of the bone 1050 to a second side 1052 of the bone 1050. Once the pass-through hole 1053 has been formed, the cable 1140 may be coupled to the hole-forming tool 1120 (as shown in FIG. 11A) to collectively pass the hole-forming tool 1120 and the cable 1140 through the pass-through hole 1053.

Figure 11A:
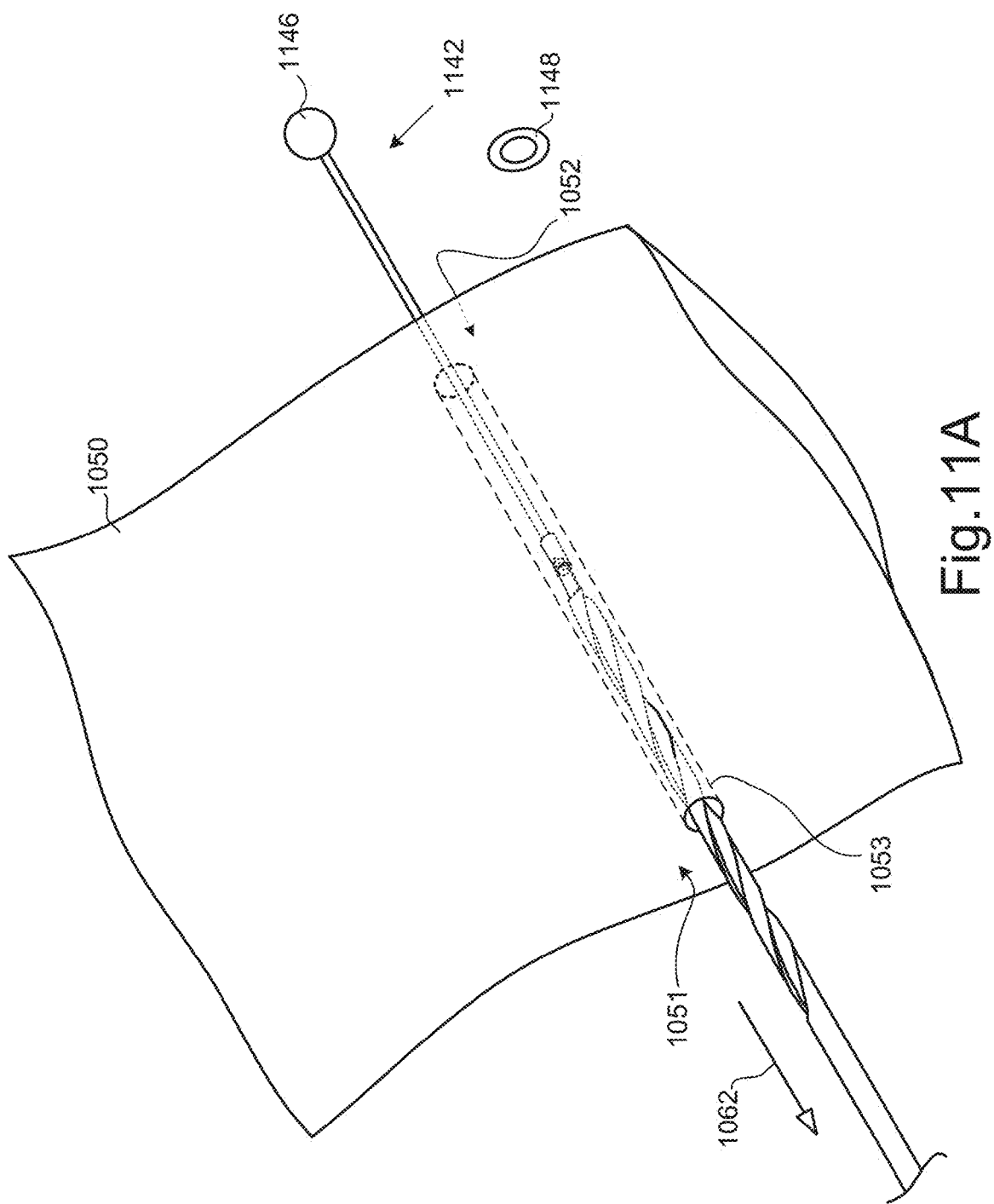
FIG. 11A is a perspective view of the hole-forming tool, with the cable coupled to the first connection feature of the hole-forming tool, being pulled in a second direction through the pass-through hole in the bone, according to one embodiment.

FIG. 11A shows the hole-forming tool 1120 being pulled in a second direction 1062 through the pass-through hole 1053 in the bone 1050 (e.g., from the second side 1052 of the bone 1050 to the first side 1051 of the bone 1050). With the second connection feature 1144 of the first-end portion 1141 of the cable 1140 being coupled to the first connection feature 1124 of the hole-forming tool 1120, the cable 1140 is pulled through the pass-through hole 1053 along with the hole-forming tool 1120. In other words, after the hole-forming tool 1120 has drilled completely through the bone 1050 and at least the first connection feature 1124 of the hole-forming tool 1120 is protruding from the pass-through hole 1053 on the second side 1052 of the bone 1050, the cable 1140 is coupled to the hole-forming tool 1120 and subsequently pulled back through the pass-through hole 1053 with the hole-forming tool 1120.

Figure 11B:
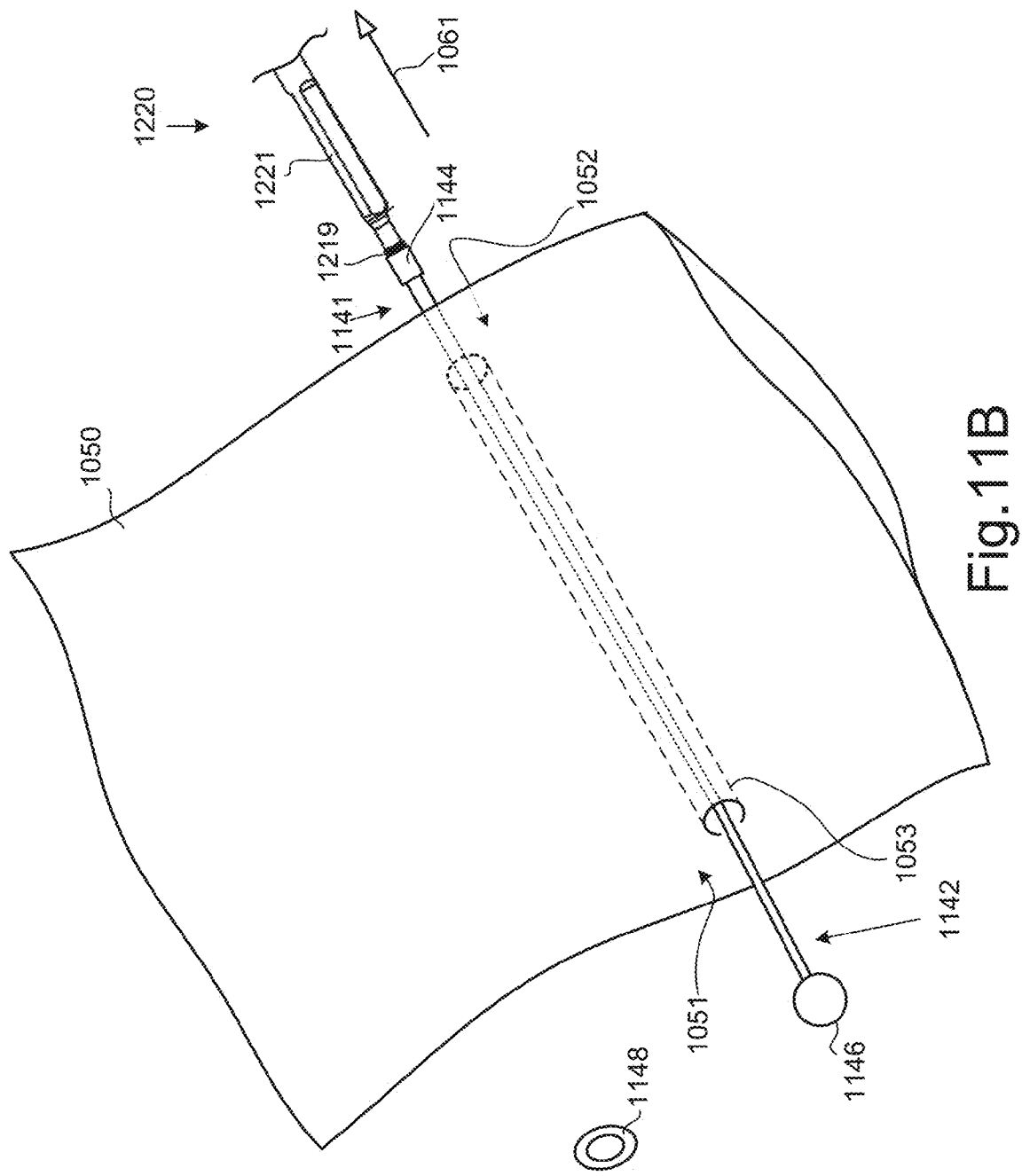
FIG. 11B is a perspective view of the hole-forming tool, with the cable coupled to the shank connection feature of the hole-forming tool, being pulled in the second direction through the pass-through hole in the bone, according to one embodiment.

In contrast to FIG. 11A, FIG. 11B shows the cable 1140 being passed through the pass-through hole 1053 in the first direction 1061, which is opposite the second direction 1062. In other words, FIG. 11B shows how the cable 1140 can be passed through the pass-through hole 1053 in the same direction the hole-forming tool 1220 (FIG. 9B) was driven to form the pass-through hole 1053. As introduced above with reference to FIG. 9B, according to one embodiment, the hole-forming tool 1220 includes the shank connection feature 1219 disposed at the end of the shank 1221 of the hole-forming tool 1220. In such an embodiment, the second connection feature 1144 of the first-end portion 1141 of the cable 1140 can be coupled to the shank connection feature 1219 of the hole-forming tool 1220. In other words, after the hole-forming tool 1220 has drilled completely through the bone 1050, leaving at least a portion of the hole-forming tool 1220 (e.g., the first connection feature 1124) protruding from the pass-through hole 1053 on the second side 1052 of the bone 1050, the drilling tool may be detached from the shank 1221, thus leaving the shank connection feature 1219 protruding from the pass-through hole 1053 on the first side 1051 of the bone 1050. In one embodiment, the cable 1140 is pre-attached to the shank connection feature 1219. In other embodiments, the cable 1140 may be coupled to the hole-forming tool 1220 via the respective connection features 1144, 1219 and the hole-forming tool 1220 and the cable may be collectively pulled through the pass-through hole 1053.

After passing the cable 1140 through the pass-through hole 1053, the cable 1140 can be tensioned to a measurable and adjustable tension, and maintained in tension by fixing retaining features to the cable 1140 at opposing open ends of the pass-through hole 1053. In some implementations, the pass-through hole 1053 extends through two bone segments of a fractured bone such that tensioning the cable 1140 to a measurable and adjustable tension in this manner causes the two bone segments to compress together with a measurable and adjustable compression. Moreover, because the cable 1140 passes through the bone, as opposed to around the bone, the compression of the two bone segments is applied in one direction (e.g., unidirectionally) concentric with the cable 1140, to more uniformly and evenly distribute the compressive load to the bone segments, as opposed to multiple directions when compression is applied by a cable passing around the bone.

In one embodiment, as an example only, the connection features 1124, 1219 of the hole-forming tool are threads that compliment and are threadably engageable with threads of the second connection feature 1144 of the cable 1140. The threads of the second connection feature 1144 may be pass-by-threads, thereby enabling the cable 1140 to rotate about its axis independent of the hole-forming tool 1120 once the threads of the second connection feature 1144 have been threaded beyond the threads of connection features 1124, 1219 so that the threads of the second connection feature 1144 are disposed proximate a non-threaded portion 1118 (as shown in FIG. 13B) of the hole-forming tool 1120. In other words, the threads of the second connection feature 1144, while no longer directly and threadably engaged with the threads of the connection features 1124, 1219 of the hole-forming tool 1120, are still retained on the non-threaded portion 1118 because the threads of the connection features 1124, 1219 act as a stop, thus allowing the hole-forming tool and the cable to rotate independently (e.g., rotate relative to each other) while still being coupled together.

Depending on the details of a specific surgical procedure, it may not be possible to pull the hole-forming tool through the pass-through hole 1053 in one of the directions. For example, if the hole-forming tool is not able to be pulled backwards (i.e., in the second direction 1062) through the pass-through hole 1053 it just formed, the cable 1140 may be connected to the shank connection feature 1219 and the hole-forming tool may continue moving through the pass-through hole 1053 in the first direction 1061. Alternatively, if working space is relatively limited on the second side 1052 of the bone 1050, it may be difficult or impossible to pass the entire hole-forming tool through the pass-through hole 1053, thus the cable 1140 may be connected to the first connection feature 1124 and the cable 1140 and hole-forming tool 1120 may be pulled backwards through the pass-through hole 1053 in the second direction 1062.

According to the embodiments depicted in FIGS. 11A and 11B, the second-end portion 1142 of the cable 1140 includes a retainer feature 1146. The retainer feature 1146 has a dimension that is larger than the diameter of the pass-through hole 1053, thus prevent the retainer feature 1146 from entering into or passing through the pass-through hole 1053. In other words, the retainer feature 1146 engages an opening of the pass-through hole 1053 on the second side 1052 of the bone 1050 (FIG. 11A) or the first side 1051 of the bone 1050 (FIG. 11B).

In one embodiment, the retainer feature 1146 is a spherical or rounded. In another embodiment, the retainer feature 1146 resembles a flange or a washer. The retainer feature 1146 may be integrated or permanently attached to the second-end portion 1142 of the cable 1140. For example, the retainer feature 1146 may be swaged to the cable 1140. In another embodiment, the retainer feature 1146 may be detachably coupled to the cable 1140, thus allowing for retainer features that have different shapes, dimensions, angles, etc. to be implemented. In another embodiment, the apparatus 1100 may also include a washer 1148 that further facilitates proper retaining engagement between the retainer feature 1146 and the surface of the bone 1050 adjacent the opening of the pass-through hole 1053. In other words, the washer 1148 may directly engage the surface of the bone 1050 and the retainer feature 1146 may be secured to, or at least engaged with, the washer 1148.

In certain surgical procedures, the practitioner may need to tension the cable 1140 in order to use the cable 1140 to adequately hold and support the various tissues (e.g., bone tissue, soft-tissue) in a desired orientation. The retainer feature 1146 enables the cable 1140 to be tensioned by preventing the cable 1140 from slipping through the pass-through hole 1053.

Figure 12:
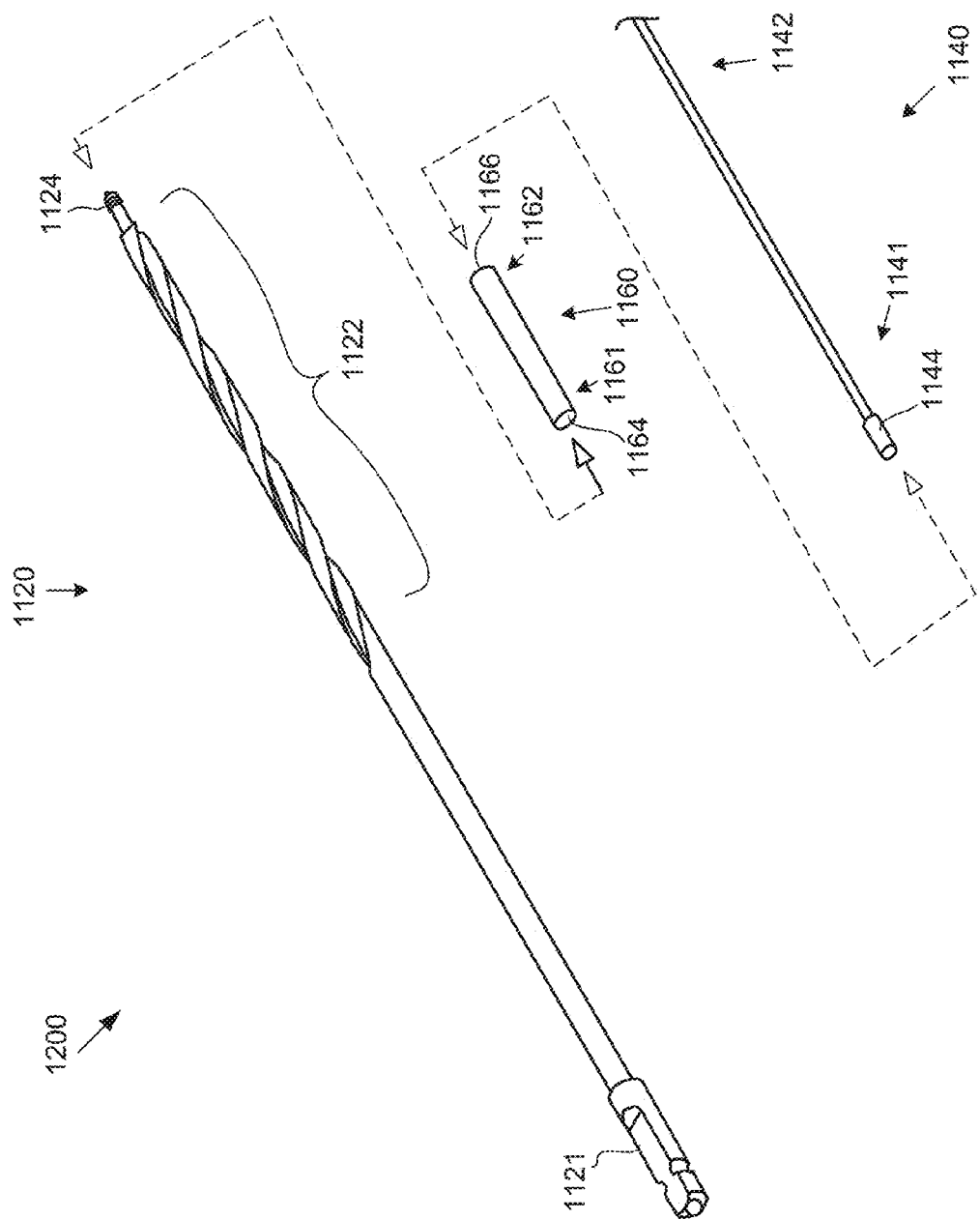
FIG. 12 is a perspective exploded view of the apparatus with a coupler, according to one embodiment.

FIG. 12 is a perspective exploded view of the apparatus 1200 with the coupler 1160, according to one embodiment. As introduced above, the coupler 1160 has a proximal-end portion 1161 and a distal-end portion 1162. The proximal-end portion 1161 has a third connection feature 1164 and the distal-end portion 1162 has a fourth connection feature 1166. The third connection feature 1164 is coupled to either the first connection feature 1124 or the shank connection feature 1219 and the fourth connection feature 1166 is coupled to the second connection feature 1144 of the first-end portion 1141 of the cable 1140.

The connecting structure of the respective complimentary connection features may include any of various connection elements. In other words, the connection features may include threads, clasps, tongue-and-groove elements, interference fit elements, magnets, and swage lock elements, among others. In one embodiment, the connection features 1124, 1219 on the hole-forming tool have a different connection structure than the second connection feature 1144 of the cable 1140, thus preventing the hole-forming tool from directly connecting to the cable 1140. In such an embodiment, the third connection feature 1164 of the coupler 1160 has a connection structure that is complimentary to the connection features 1124, 1219 of the hole-forming tool while the fourth connection feature 1166 has a connection structure that is complimentary to the second connection feature 1144 of the cable 1140, thus allowing otherwise incompatible connection features on the hole-forming tool and the cable 1140 to be indirectly coupled together via the coupler 1160.

In one example, the connection features 1124, 1219 of the hole-forming tool have externally facing threads and the third connection feature 1164 of the coupler 1160 has internally facing threads that are threadably engageable with the externally facing threads of the hole-forming tool connection features 1124, 1219. In one embodiment, the third connection feature 1164 of the coupler 1160 has pass-by-threads, thereby enabling the coupler to rotate about its axis independent of the hole-forming tool once the threads of the third connection feature 1164 have been threaded entirely through the threads of the first connection feature 1124 or the shank connection feature 1219. In another embodiment, the second connection feature 1144 of the first-end portion 1141 of the cable 1140 has a non-threaded protrusion and the fourth connection feature 1166 of the distal-end portion 1162 of the coupler 1160 has a complimentary non-threaded cavity such that the non-threaded protrusion of the second connection feature 1144 is configured to be received into the non-threaded cavity of the fourth connection feature 1166 via an interference fit.

In one embodiment, the coupler 1160 facilitates a quick and easy connection between the hole-forming tool and the cable 1140. For example, in certain surgical conditions it may be difficult to couple the cable 1140 directly to the hole-forming tool 1120 due to lack of space on one side of the bone or limited visibility on that side of the bone.

The coupler 1160 may be made from various materials, including metals such as stainless steel and synthetics such as plastic, polymer, and composite material. The coupler 1160 material may be flexible, resiliently flexible, or rigid. In one embodiment, the coupler 1160 is disposable. In another embodiment, the coupler 1160 may be sterilized for re-use. The coupler 1160 may have an external cross-sectional dimension that is substantially uniform along the entire length of the coupler. In another embodiment, the external cross-sectional dimension of the coupler 1160 may vary along its length. Also, while the cross-sectional shape of the coupler 1160 is depicted as being circular (e.g., a cylindrical body), in other embodiments the coupler 1160 may have a rectangular or polygonal cross-sectional shape. In one embodiment, the diameter of the coupler 1160 is at least less than the diameter of the cutting portion 1122 of the hole-forming tool, thus allowing the coupler to easily pass through the pass-through hole 1053.

FIG. 13A is a perspective view the first connection feature 1124 of the hole-forming tool 1120 and FIG. 13B is a side view of the first connection feature 1124 of the hole-forming tool 1120, according to one embodiment. The hole-forming tool 1120 includes a second cutting portion 1128. In other words, the first connection feature 1124 is interposed between the first cutting portion 1122 (described above) and the second cutting portion 1128. The second cutting portion 1128 includes a cutting tip 1130 that has a diameter that is smaller than the diameter of the first cutting portion 1122. In other words, the cutting tip 1130 drills a guide hole and the first cutting portion 1122 expands the guide hole to the size of the pass-through hole 1053 shown in the figures. In one embodiment, the diameter of the second cutting portion 1128 may be the same size or just larger than the diameter of the first connection feature 1124. In other words, the first connection feature 1124 may be slightly radially recessed relative to the second cutting portion 1128, thus ensuring the guide hole/pilot hole is large enough to not damage the first connection feature 1124 (e.g., threads). In the embodiment depicted in FIGS. 13A and 13B, the hole-forming tool may also include cutaway portions that further facilitate cutting and drilling through the bone 1050.

Figure 14A:
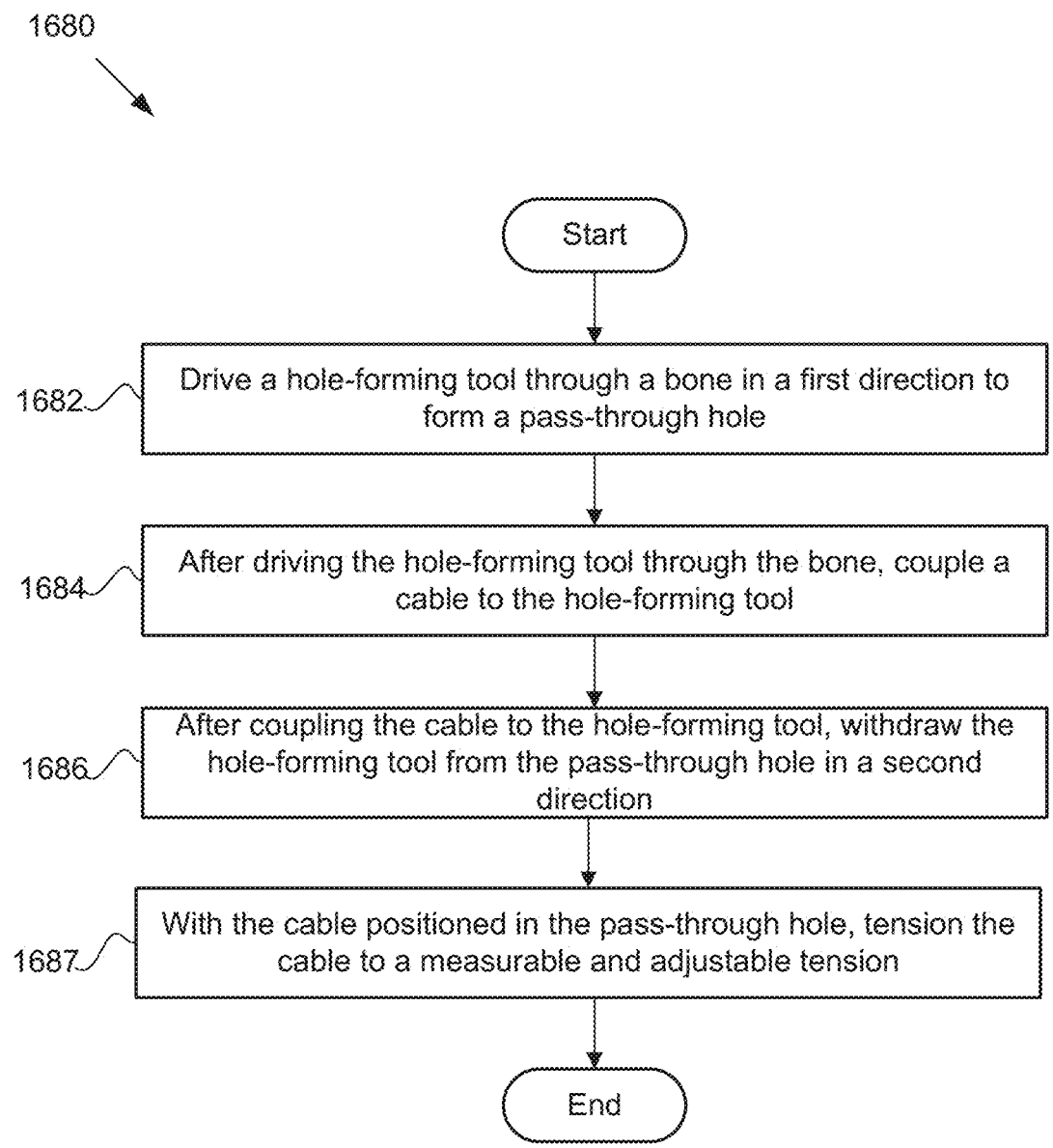
FIG. 14A is a schematic flowchart diagram of a method for passing cable through bone in the second direction, according to one embodiment.
Figure 14B:
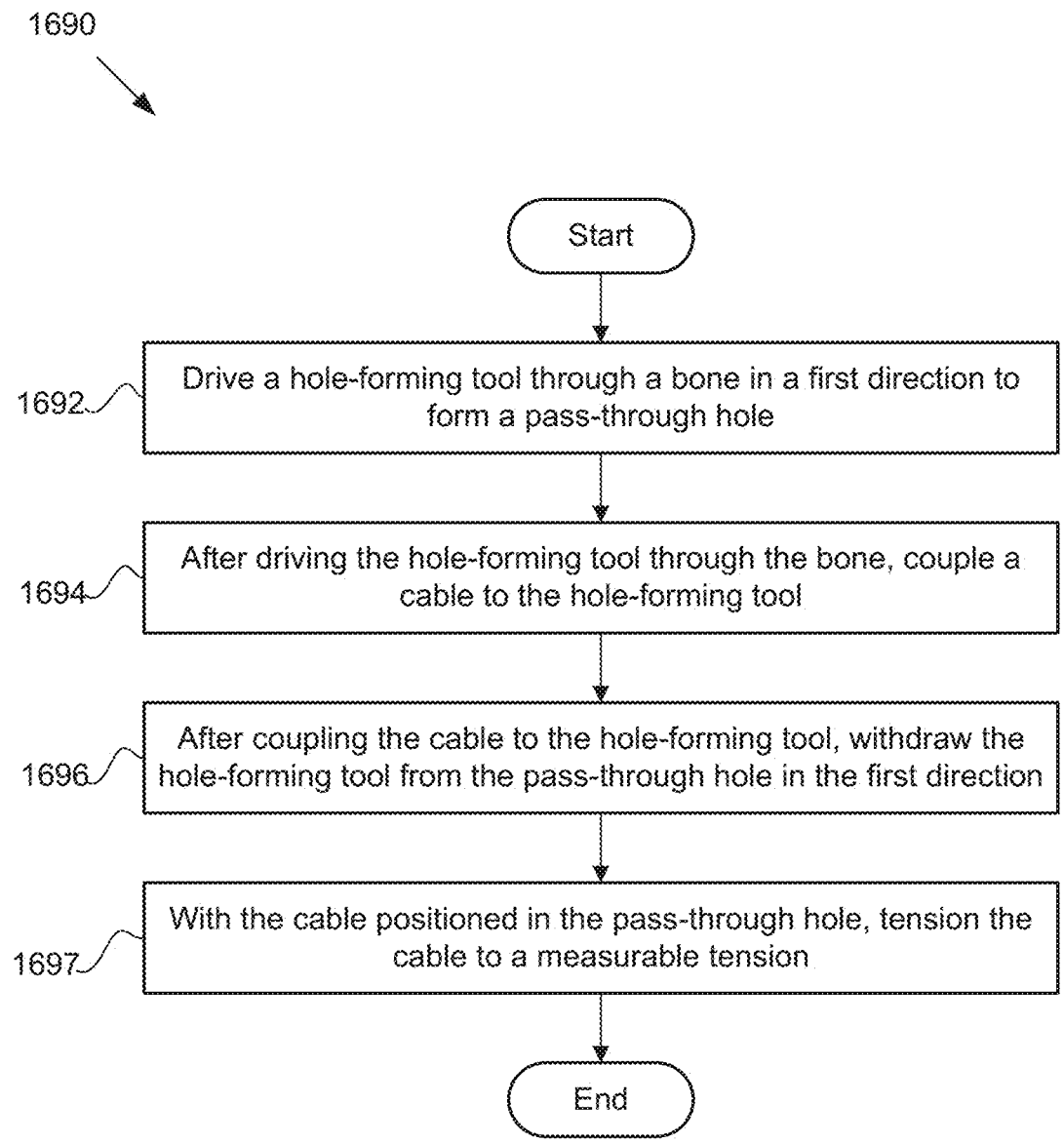
FIG. 14B is a schematic flowchart diagram of the method for passing cable through bone in the first direction, according to one embodiment.

FIG. 14A is a schematic flowchart diagram of a first method 1680 for passing cable through bone in the second direction 1062, according to one embodiment, and FIG. 14B is a schematic flowchart diagram of a second method 1690 for passing cable through bone in the first direction 1061, according to one embodiment. The first method 1680 includes driving the hole-forming tool 1120 through the bone in the first direction 1061 to form a pass-through hole 1053 extending from the first side 1051 of the bone 1050 to the second side 1052 of the bone until at least the first connection feature 1124 of the hole-forming tool 1120 protrudes from the pass-through hole 1053 on the second side 1052 of the bone 1050 at 1682. The first method 1680 further includes subsequently coupling the cable 1140 to the hole-forming tool 1120 via the first connection feature 1124 of the hole-forming tool 1120 and the second connection feature 1144 of the cable 1140 at 1684 and then withdrawing the hole-forming tool 1120 from the pass-through hole 1053 in the second direction 1062 opposite the first direction 1061 to pull the cable 1140 through the pass-through hole 1053 such that at least a portion of the cable 1140 protrudes from the first side 1051 of the bone 1050 at 1686. With the cable positioned in the pass-through hole, the method 1680 further includes tensioning the cable to a measurable and adjustable tension at 1687, to cause a measurable and adjustable compression of the bone by the cable in some implementations. In one embodiment, the method 1680 may optionally include, after the cable is tensioned to a measurable and adjustable tension, releasing the tension in the cable and re-tensioning the cable, while positioned in the pass-through hole or otherwise, to the same or different measurable and adjustable tension. Releasing the tension in the cable may include unlocking a lock that is configured to maintain the cable in tension. The ability to release tension in a cable and subsequently re-tension the cable provides various advantages, such as, for example, facilitating re-use of the cable on other targeted areas of the body in one or more subsequent procedures, in some implementations, and adjustment to the tension or position of the cable on the same targeted area of the body in the same or a subsequent procedure, in other implementations.

Coupling the cable 1140 to the hole-forming tool 1120 may include coupling the hole-forming tool 1120 directly to the coupler 1160 via engagement between the first connection feature 1124 of the hole-forming tool 1120 and the third connection feature 1164 of the proximal-end portion 1161 of the coupler 1160 and also coupling the coupler 1160 directly to the cable 1140 via engagement between the fourth connection feature 1166 of the distal-end portion 1162 of the coupler 1160 and the second connection feature 1144 of the first-end portion 1141 of the cable 1140. In another implementation, the step of withdrawing the hole-forming tool from the pass-through hole at 1686 includes engaging the retainer feature 1146 of the second-end portion 1142 of the cable 1140 with an opening of the pass-through hole 1053 on the second side 1052 of the bone 1050. In one implementation, driving the hole-forming tool at 1682 includes cutting the bone with the first cutting portion 1122 of the hole-forming tool and the second cutting portion 1128 of the hole-forming tool 1120, with the second cutting portion 1128 forming a pilot hole for the first cutting portion 1122.

The second method 1690 shown in FIG. 14B includes driving the hole-forming tool 1220 through the bone 1050 in the first direction 1061 to form the pass-through hole 1053 extending from the first side 1051 of the bone 1050 to the second side 1052 of the bone 1050, leaving at least the shank connection feature 1219 of the hole-forming tool 1220 protruding from the pass-through hole 1053 on the first side 1051 of the bone 1050 at 1692. The second method 1690 subsequently includes coupling the cable 1140 to the hole-forming tool 1220 via the shank connection feature 1219 of the hole-forming tool 1220 and the second connection feature 1144 of the cable 1140 at 1694 and then withdrawing the hole-forming tool 1220 from the pass-through hole 1053 in the first direction 1061 to pull the cable 1140 through the pass-through hole 1053 such that at least a portion of the cable 1140 protrudes from the second side 1052 of the bone 1050. With the cable positioned in the pass-through hole, the method 1690 further includes tensioning the cable to a measurable and adjustable tension at 1697, to cause a measurable and adjustable compression of the bone by the cable in some implementations. In one embodiment, the method 1690 may optionally include, after the cable is tensioned to a measurable and adjustable tension, releasing the tension in the cable and re-tensioning the cable, while positioned in the pass-through hole or otherwise, to the same or different measurable and adjustable tension.

In one embodiment, coupling the cable 1140 to the hole-forming tool 1220 at 1696 includes coupling the hole-forming tool 1220 directly to the coupler 1160 via engagement between the shank connection feature 1219 of the hole-forming tool 1220 and the third connection feature 1164 of the coupler 1160 and also coupling the coupler 1160 directly to the cable 1140 via direct engagement between the fourth connection feature 1166 of the coupler 1160 and the second connection feature 1144 of the first-end portion 1141 of the cable 1140. In another implementation, withdrawing the hole-forming tool 1220 from the pass-through hole 1053 includes engaging a retainer feature 1146 of the second-end portion 1142 of the cable 1140 with an opening of the pass-through hole 1053 on the first side 1051 of the bone 1050.

Soft-Tissue Fixation Devices

Illustrated in FIGS. 15A-18 are several representative embodiments of a soft-tissue fixation device for repairing damaged or torn soft-tissues, such as tendons and ligaments. In some implementations, the soft-tissue fixation device is configured to both fixate soft tissue relative to the soft-tissue fixation device and fixate the soft tissue relative to bone. More specifically, with the soft tissue fixated or secured by the soft-tissue fixation device, the soft-tissue fixation device can be fixated to bone by securing at least one tensionable cable to the soft-tissue fixation device and fixating the cable relative to the bone by tensioning the cables. Accordingly, the soft-tissue fixation device can be any device configured to fixate soft tissue, such as clamps, staples, braces, bands, clasps, and the like. In this regard, although the example of the soft-tissue fixation device specifically described and illustrated herein resembles a clamp, with two separate portions configured to fixate soft tissue between them, in other embodiments, the soft-tissue fixation device can be configured more like a staple, with a single portion that bends or deforms to fixate soft tissue. As described herein, the soft-tissue fixation device provides various advantages and benefits over other medical tools and procedures. However, the recited advantages are not meant to be limiting in any way, as one skilled in the art will appreciate that other advantages may also be realized upon practicing the present disclosure.

Figure 15A:
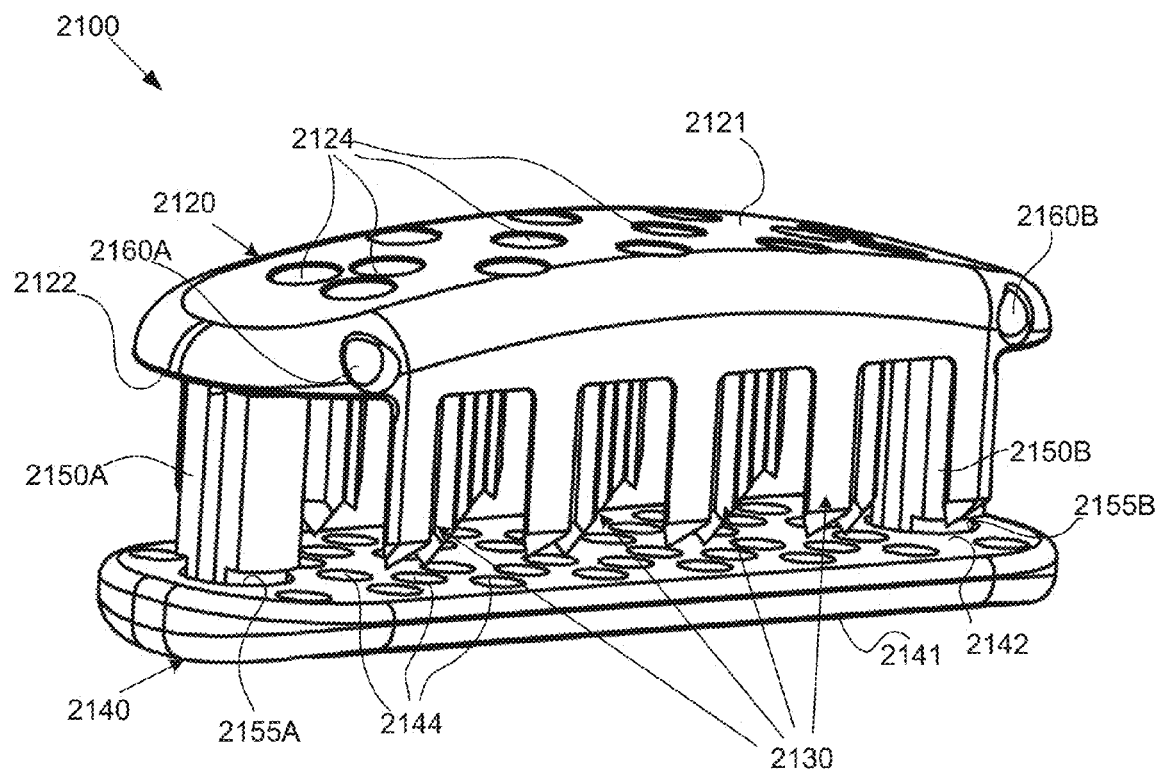
FIG. 15A is a front perspective view of a soft-tissue fixation device having a first plate, a second plate, and a plurality of tines, according to one embodiment.
Figure 15B:
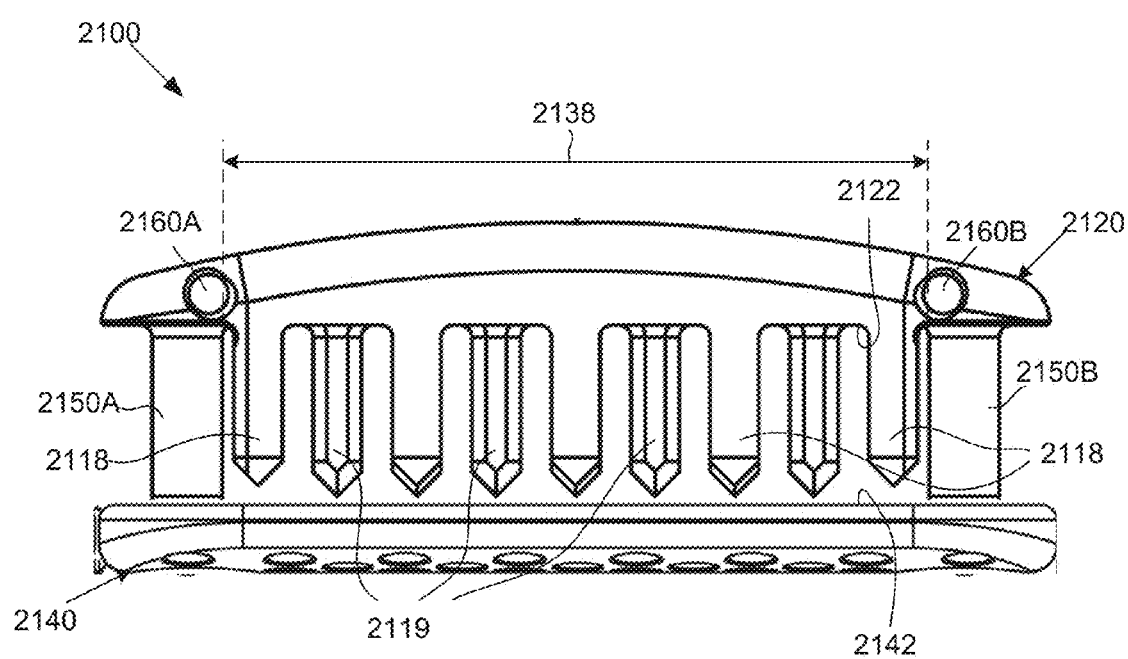
FIG. 15B is a front view of the soft-tissue fixation device of FIG. 15A, according to one embodiment.

FIGS. 15A and 15B show a front perspective view and a front view, respectively, of one embodiment of the soft-tissue fixation device 2100. The soft-tissue fixation device 2100 has a first plate 2120, a second plate 2140, and a plurality of tines 2130. The first plate 2120 has a first clamping surface 2122 and the plurality of tines 2130 extend from the first clamping surface 2122. According to the embodiment depicted in the figures, the tines 2130 are substantially parallel to each other. In another embodiment, the tines 2130 may not be parallel to each other and may have different extension directions. For example, the tines 2130 may have alternating extension directions. In another embodiment, tines may extend from both plates 2120, 2140.

The first plate 2120 is configured to be positioned on a first side of a soft-tissue segment and the plurality of tines 2130 extending from the first clamping surface 2122 of the first plate 2120 are configured to extend through the soft-tissue segment. The second plate 2140 has a second clamping surface 2142 and the second plate 2140 is configured to be positioned on a second side of the soft-tissue segment with the second clamping surface 2142 facing the first clamping surface 2122. With the plates 2120, 2140 positioned on opposite sides of the soft-tissue segment, the tines 2130 may be inserted and extend through the soft-tissue segment until the first plate 2120 and the second plate 2140 are connected together using a connection mechanism. The term "soft-tissue segment" refers to at least a partial portion or a partial section of a soft tissue. For example, in one embodiment, the plates 2120, 2140 are configured to clamp around the entire cross-sectional dimension of a soft tissue. However, in another embodiment, the plates 2120, 2140 clamp around only a partial cross-section of the soft tissue, thus one or both of the plates 2120, 2140 may actually be embedded within or disposed within the soft tissue. In other words, the use of the terms "first side" and "second side" of the soft-tissue segment may not necessarily refer to external sides of a soft tissue but instead may refer to internal surfaces/sides of the soft-tissue.

The soft-tissue fixation device 2100 may be made from any of various materials, including metals, such as stainless steel and titanium, and synthetics, such as a rigid plastic, polymer, or composite. In another embodiment, the soft-tissue fixation device 2100 is made from a bio-resorbable material. In an alternative embodiment, the soft-tissue fixation device is not implemented with the second plate, but instead the plurality of tines extending from the first plate are made from a shape-memory alloy (e.g., Nitinol). The shape of shape-memory alloys are temperature dependent. Accordingly, the tines may be inserted to extend through the soft-tissue segment and thereafter when the temperature of the plurality of tines is raised or lowered to a predetermined temperature (e.g., body temperature), the plurality of tines may undergo torsional deformation. The torsionally deformed tines intertwine with the fibers of the soft-tissue segment to securely hold the soft-tissue fixation device in place (while still allowing blood to flow through the soft-tissue segment).

The soft-tissue fixation device 2100 is configured to securely attach to the soft-tissue segment while still allowing blood to flow through the soft-tissue segment. In one example, the soft-tissue fixation device 2100 may be used to couple together two sections of a torn tendon. In another embodiment, to secure the soft tissue to bone, the soft-tissue fixation device 2100 may be used as an anchor point to which cables or other surgically installed implements (pins, screws, etc) may be coupled. For example, the soft-tissue fixation device 2100 may be used to secure soft-tissue to bone. According to the embodiment shown in the figures, the plates 2120, 2140 also include one or more pass-through apertures 2124 and one or more cable holes 2160A, 2160B. The pass-through apertures 2124, according to one embodiment, extend through the plates 2120, 2140 to promote proper blood flow through the soft-tissue segment being clamped by the soft-tissue fixation device 2100.

Figure 16A:
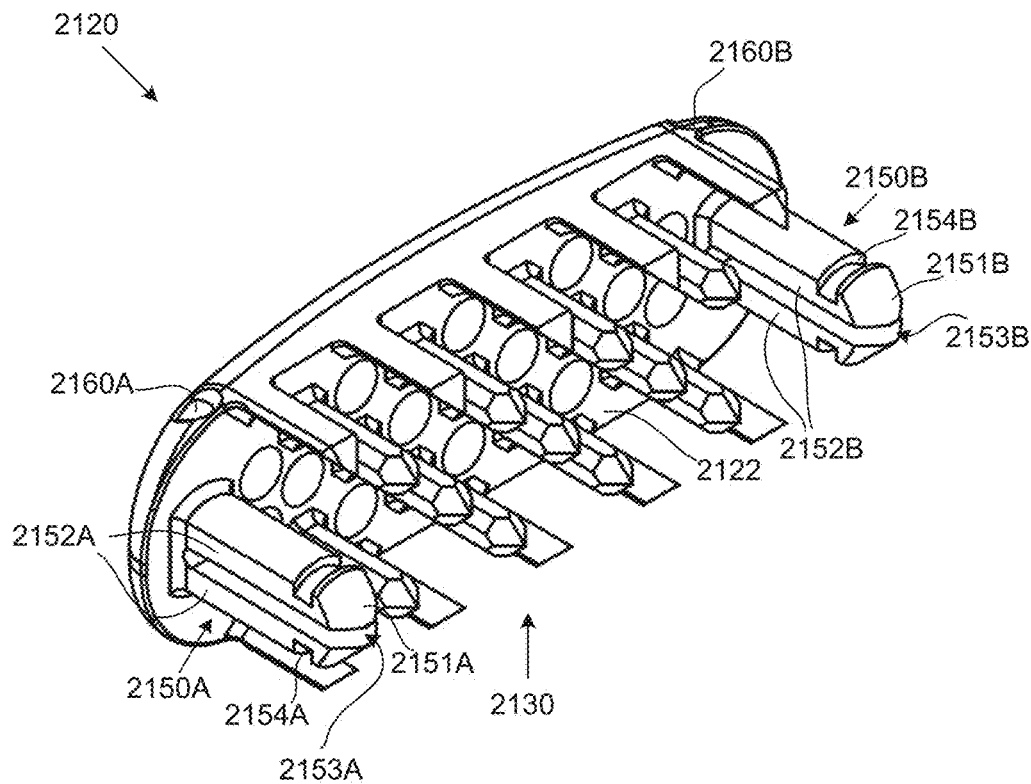
FIG. 16A is a bottom perspective view of the first plate of the soft-tissue fixation device, according to one embodiment.
Figure 16B:
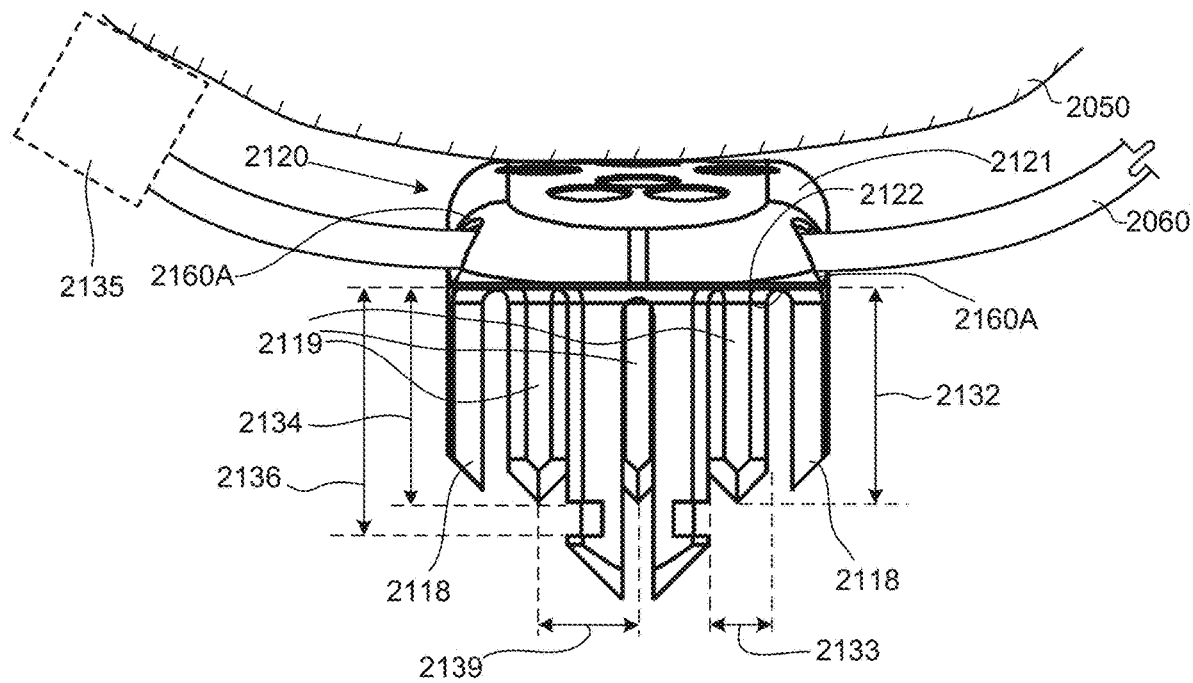
FIG. 16B is a side view of the first plate of the soft-tissue fixation device, according to one embodiment.

Referring to FIG. 16B, the soft-tissue fixation device 2100 can be coupled with at least one other object using one or more tensionable cables 2060. Generally, the soft-tissue fixation device 2100 is coupled with another object to fixate the soft-tissue fixation device 2100, and thus soft-tissue fixated by the soft-tissue fixation device, relative to that object. The at least one object can be one or more of any of various objects, such as the bone 2050 and/or the object 2135. The soft-tissue fixation device 2100 and the at least one other object are coupled together by coupling at least one cable 2060 with both the soft-tissue fixation device and the at least one other object. Then, the soft-tissue fixation device 2100 is fixated relative to the at least one other object by tensioning the at least one cable 2060 to a measurable and adjustable tension. The soft-tissue fixation device 2100 may include at least one cable-retention feature to facilitate the coupling of the cable 2060 to the soft-tissue fixation device 2100.

The object 2135 can be any of various objects, such as bone-anchoring objects, soft-tissue fixation devices, or other medical devices. For example, in one implementation, the object 2135 is a bone-anchoring object (e.g., a bone anchor, bone pin, washer, external bone fixation device, internal bone fixation device, etc.) attached or fixed relative to the bone 2050 such that directly coupling or fixating the soft-tissue fixation device 2100 to the object 2135 via the cable 2060 indirectly couples or fixates the soft-tissue fixation device to the bone 2050. As another example, in one implementation, the object 2135 is a soft-tissue fixation device (secured or unsecured relative to bone) such that directly coupling or fixating the cable 2060 to the soft-tissue fixation devices directly couples or fixates together the soft-tissue fixation devices.

In some implementations, the cable-retention features of the soft-tissue fixation device 2100 are one or more cable holes 2160A, 2160B. The cables 2060 are coupled to the soft-tissue fixation device 2100 by passing the cables 2060 through one or more of the cable holes 2160A, 2160B in the fixation device 2100 as shown in FIG. 16B. In one embodiment, the cable holes 2160A, 2160B extend through the plates 2120, 2140 in a direction that is perpendicular to the extension direction of the tines 2130. In another embodiment, the cable holes 2160A, 2160B may extend through the plates 2120, 2140 in a direction that is parallel with the extension direction of the tines 2130. In yet another embodiment, the extension direction of the cable holes through the plates may be oblique relative to the extension direction of the tines. The cable-retention feature may be a recess or cavity that receives an end of the cables to facilitate pre-attachment of the cables 2060 to the soft-tissue fixation device 2100, such as by being fastened to, adhered to, boned to, embedded in, or crimped by, the soft-tissue fixation device. As mentioned above, after passing through one of the cable holes 2160A, 2160B of the soft-tissue fixation device 2100, or after being pre-attached to the soft-tissue fixation device, a cable 2060 may pass-through a hole or tunnel in a bone, or wrap around one or more tissues or bones (e.g., a cerclage configuration), before being tensioned.

According to one embodiment, the term "cable" refers to a cord-like element, such as a wire, filament, weave, or thread, whether bundled or individual, that is capable of holding a measurable and adjustable tension and causing a measurable and adjustable compression of bone. In other words, the tension in the cable can be measured, such as by a tension measuring device, and can be adjusted, such as after an initial tensioning of the cable. When used to compress bone (e.g., to compress two bone segments together), the measured tension in the cable is equal to a measured compression of the bone. Thus, as used herein, a measured and adjustable tension of a cable is synonymous with a measured and adjustable compression of bone by the cable.

In one embodiment, the measurable and adjustable tension may be a specific, known, predictable, expected, controllable, anticipated, desired, repeatable, sustainable, and/or predeterminable tension. For example, the cable may be passed through a pass-through hole in a bone and may be tensioned to a measurable and adjustable tension in order to facilitate the reduction and fixation of fractures or to otherwise facilitate the repair of dislocations or soft-tissue damage. In other words, the cable is not a conventional suture or conventional thread material, since such materials are incapable of, or at least not well-suited for, maintaining a measurable and adjustable tension. Thus, the term "cable" refers to a flexible yet substantially non-stretchable element that can be tensioned to a measurable and adjustable tension. In such an embodiment, because the cable is capable of maintaining or retaining a measurable and adjustable tension, the effectiveness and reproducibility of successful surgical procedures is improved. In other words, different surgical procedures relating to different bones in the body may involve different degrees of retention/fixation force (e.g., the fixation force required to reduce a fracture in the femur may be greater than the fixation force required to reduce a fracture in the patella). Accordingly, the ability of the cable to be tensioned to a measurable and adjustable tension improves the reliability and reproducibility of surgical procedures when compared with other medical procedures that do not utilize cables. The cable 2060 may be made from any one of various materials. For example, in specific implementations, the cable 2060 is made from metal, such as stainless steel, titanium, or other metal. As mentioned above, the tensioned cables can extend through the cable holes 2160A, 2160B in the soft-tissue fixation device 2100 to secure or reattach the soft-tissue to bone.

As shown in FIGS. 15A-17B, the first plate 2120 and the second plate 2140 each has an external surface 2121, 2141 that is opposite the respective clamping surface 2122, 2142. According to one embodiment, the clamping surfaces 2122, 2142 are planar while the external surfaces 2121, 2141 of the plates 2120, 2140 are curved. In the depicted embodiment, the external surfaces 2121, 2141 also have curved edges and smooth corners. The curved and smooth nature of the external surfaces 2121, 2141 may conform to the shape of the tissues and body parts surrounding the soft-tissue segment.

Various types of connection mechanisms may be implemented to connect the two plates 2120, 2140 together to clamp around the soft-tissue segment with the tines 2130 extending through the soft-tissue segment. In one embodiment, the connection mechanism not only connects the two plates 2120, 2140 together but also is configured as a spacing member to control the minimum distance between the clamping surfaces 2122, 2142 of the plates 2120, 2140. According to the embodiment depicted in the figures, the soft-tissue fixation device 2100 includes two spacing members 2150A, 2150B extending from the first plate 2120. These spacing members 2150A, 2150B are respectively engageable with two engagement features 2155A, 2155B of the second plate 2140. In another embodiment, the spacing members may extend from the second plate and the engagement features may be disposed on the first plate.

The engagement between the spacing members 2150A, 2150B and the engagement features 2155A, 2155B maintains a predetermined distance between the first clamping surface 2122 and the second clamping surface 2142 that is equal to or more than a length 2132 of the longest tine of the plurality of tines 2130 (see, e.g., FIG. 16B). In one embodiment, the tines 2130 may all have the same length. However, in another embodiment the tines 2130 may have different lengths. Additional details relating to the dimensions and configuration of the tines 2130 are included below with reference to the remaining figures. In one embodiment, the soft-tissue fixation device may have a single spacing member and its corresponding engagement feature. In another embodiment, the soft-tissue fixation device may have more than two spacing members. Additional details regarding the spacing members are included below with reference to FIG. 18.

Figure 17A:
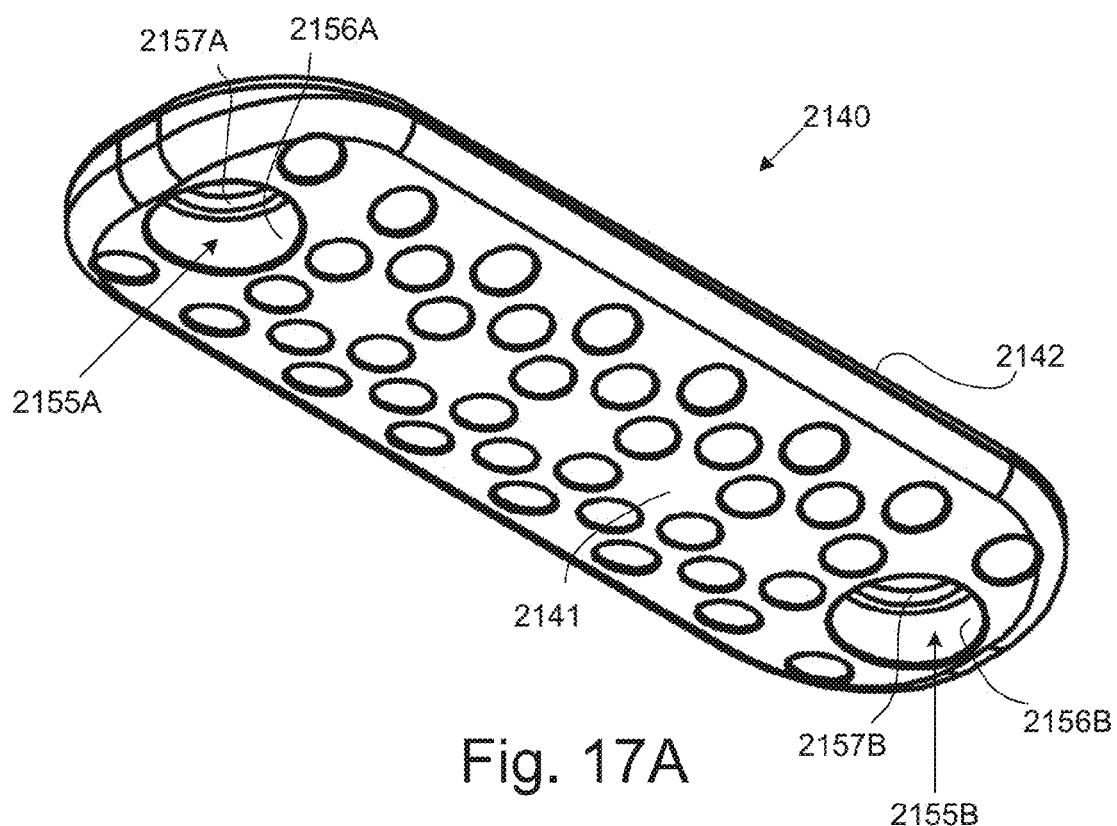
FIG. 17A is a bottom perspective view of the second plate of the soft-tissue fixation device, according to one embodiment.
Figure 17B:
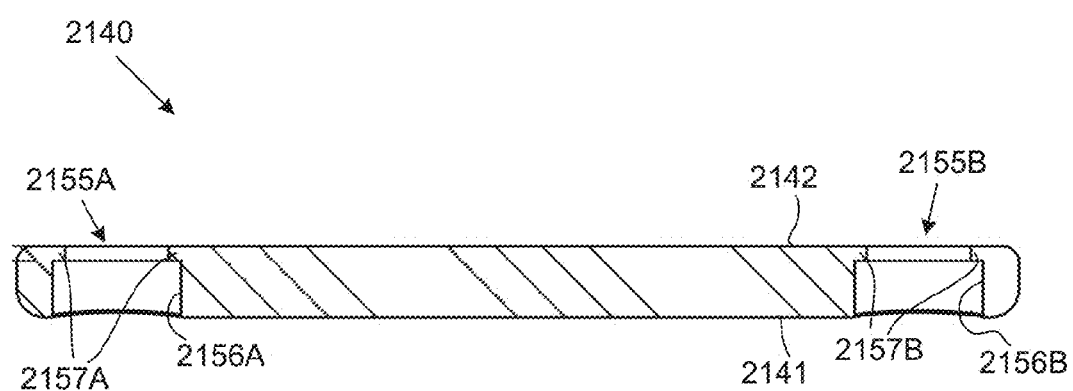
FIG. 17B is a front view of the second plate of the soft-tissue fixation device, according to one embodiment.

FIGS. 16A and 16B are a perspective view and a side view, respectively, of the first plate 2120 of the soft-tissue fixation device 2100. According to the depicted embodiment, at least a portion of each of the spacing members 2150A, 2150B is structured to have two prongs 2152A, 2152B made from a resiliently flexible material (in another embodiment, the spacing members may have more than two prongs). A gap 2153A, 2153B is interposed between the two prongs 2152A, 2152B such that the prongs 2152A, 2152B are bendable inwards toward each other. Each prong 2152A, 2152B has a tip 2151A, 2151B that converges towards the gap 2153A, 2153B in a direction from the first clamping surface 2122 to the second clamping surface 2142. Also, at least one of the prongs 2152A, 2152B of each spacing member 2150A, 2150B has a notch 2154A, 2154B on a lateral side. According to the depicted embodiment, the engagement features 2155A, 2155B are holes 2156A, 2156B and each hole has a lip 2157A, 2157B (FIGS. 17A and 17B). The two prongs 2152A, 2152B are configured to bend inwards as the tip 2151A, 2151B of each prong 2152A, 2152B of each spacing member 2150A, 2150B engages the lip 2157A, 2157B of the hole 2156A, 2156B upon insertion of the spacing member 2150A, 2150B into the hole 2156A, 2156B until the lip 2157A, 2157B is receivably engaged in the notch 2154A, 2154B.

According to the embodiments depicted in FIGS. 15A, 15B, 16A, and 16B, the notch 2154A, 2154B of each spacing member 2150A, 2150B has a width, as measured in a direction extending between the two plates 2120, 2140, that enables a degree of fluctuation in the distance between the first and second clamping surfaces 2122, 2142. For example, the lips 2157A, 2157B of the engagement features 2155A, 2155B may be able to move in the direction extending between the two plates while remaining locked within the notches 2154A, 2154B of the spacing members 2150A, 2150B. In such an example, the distance between the two plates 2120, 2140 may be allowed to fluctuate between a minimum distance 2134 and a maximum distance 2136. As mentioned above, the soft-tissue fixation device 2100 holds securely to the soft-tissue segment while still allowing blood to flow through the soft-tissue segment clamped between the soft-tissue fixation device 2100. Accordingly, the slight fluctuation in the distance between the two plates 2120, 2140 may facilitate adequate blood flow through the fixation device 2100.

In one embodiment, the tines 2130 are organized into one or more arrays of tines. As used herein, the term "array" refers to a section of tines 2130 that has a uniform extension direction, a common location relative to the plates 2120, 2140, a common shape, etc. In one embodiment, all of the tines 2130 form an array that is interposed between two spacing members 2150A, 2150B. In such an embodiment, the width of the array of tines may correspond with the width of the soft-tissue segment. In other words, a specific soft-tissue fixation device may be selected based on the width of its array of tines and the width of the specific soft-tissue segment to which the fixation device 2100 will be coupled. In one embodiment, the soft-tissue segment has a width that allows it to fit between the two spacing members 2150A, 2150B, (i.e., the spacing members 2150A, 2150B are positioned and extend from proximate opposing edges of the first clamping surface 2122) thus allowing the tines to intersect and extend through the soft-tissue segment while the spacing members 2150A, 2150B do not extend through the soft-tissue segment but instead form borders around the soft-tissue segment, thus improving the stability of the attachment of the soft-tissue fixation device 2100 to the soft-tissue segment. However, in another embodiment, the spacing members 2150A, 2150B may be configured to intersect and extend through the soft-tissue segment.

In one embodiment, the tines are organized into an array that has rows of tines. The distance 2139 between adjacent tines and/or adjacent rows of tines may be selected based on the specific type of soft-tissue segment. In one embodiment, the spacing between tines 2130 has a significant effect on the amount of blood that is able to flow through the soft-tissue segment and also a significant effect on the stability of the attachment between the fixation device 2100 and the soft-tissue segment. If the tines 2130 are spaced too far apart from each other, the fixation device 2100 will not be securely attached to the soft-tissue segment. Conversely, if the tines 2130 are spaced too close to each other, the fixation device 2100 will restrict blood flow through the soft-tissue segment, thus adversely affecting the natural healing process. In one embodiment, the distance 2139 between rows of tines 2130 is about 0.075 inches. The cross-sectional dimension 2133 of each tine also has an effect on the blood flow of the soft-tissue segment and the stability of the fixation device 2100.

In one embodiment, the plurality of tines 2130 extends substantially perpendicularly from the first clamping surface 2122. In one embodiment, each of the tines 2130 has a non-circular cross-section (e.g., rectangular, polygonal, ovular, obround, etc). In another embodiment, the cross-section of the tines may be circular. According to the embodiment depicted in the figures, the tines also have a pointed tip that facilitates insertion of the tines through the soft-tissue segment. In another embodiment, as depicted in FIG. 16B, the plurality of tines 2130 has peripheral tines 2118 and middle tines 2119. The peripheral tines 2118 are the tines extending from proximate the edge of the first clamping surface 2122 and the middle tines 2119 are centrally located relative to the peripheral tines 2118. In one embodiment, the peripheral tines 2118 have tips of a first configuration (e.g., single surfaced) and the middle tines 2119 have tips of a second configuration (e.g., multi-surfaced), the first configuration being different than the second configuration. In another embodiment, the length of the peripheral tines is different than the length of the middle tines (FIG. 15B). In yet another embodiment, the tines may be inclined relative to the clamping surface 2122 (e.g., the tines may be oblique to the clamping surface 2122).

Figure 18:
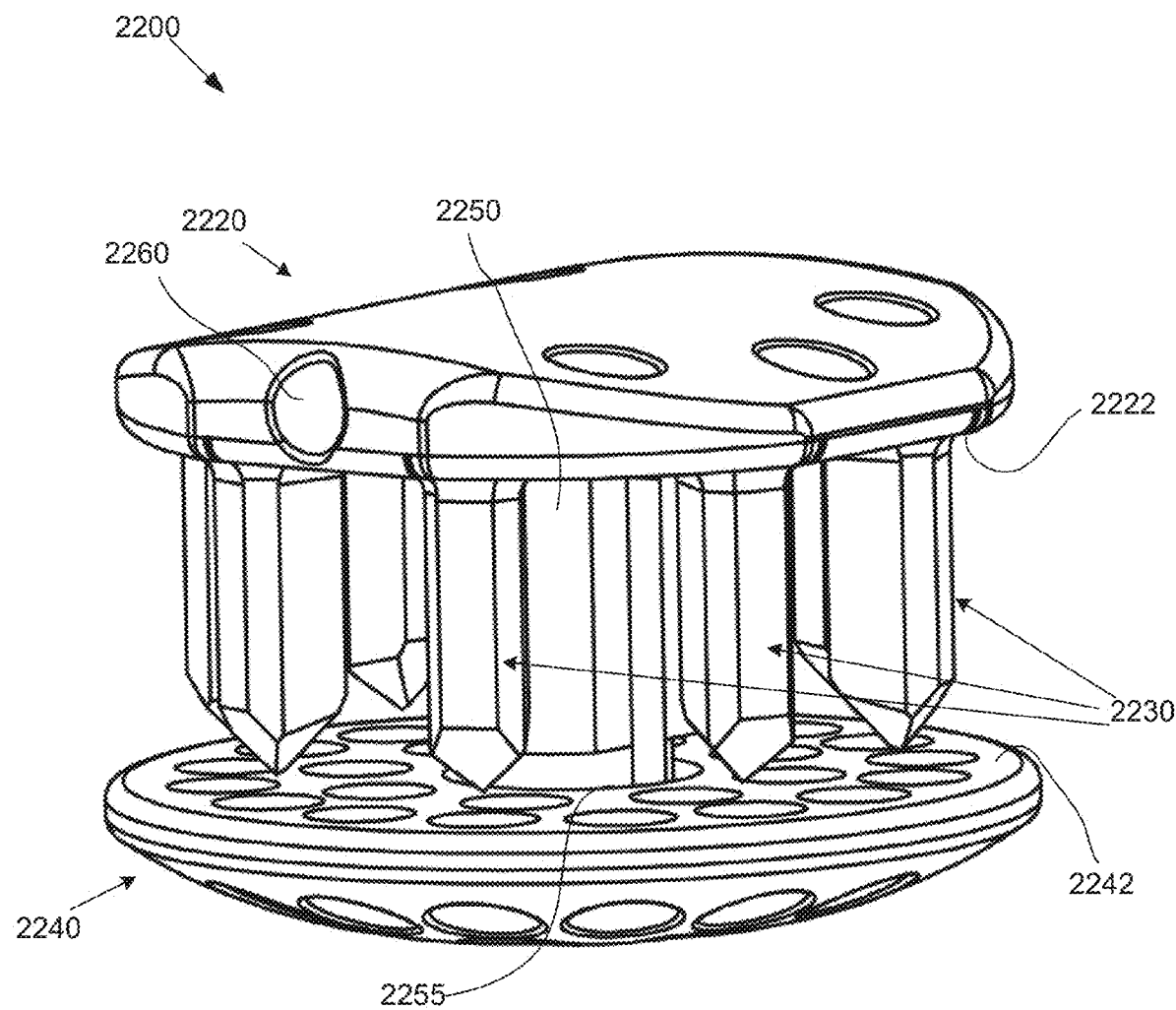
FIG. 18 is a front perspective view of another embodiment of the soft-tissue fixation device.

FIG. 18 is a front perspective view of another embodiment of the soft-tissue fixation device 2200. In the depicted embodiment, the soft-tissue fixation device 2200 has a single spacing member 2250 that extends from a central location of the clamping surface 2222 of the first plate 2220. The central spacing member 2250 engages the single central engagement feature 2255 disposed on a central location of the second plate 2240. The plurality of tines 2230 are arranged around the central spacing member 2250. The soft-tissue fixation device 2200 depicted in FIG. 18 also shows a single cable hole 2260 extending through the first plate 2220 in a direction that is perpendicular to the extension direction of the tines 2230. In one embodiment, the plates 2120, 2140 have a circular shape. In another embodiment, the plates 2120, 2140 are ovular, elliptical, or obround (e.g., racetrack like)

Figure 19:
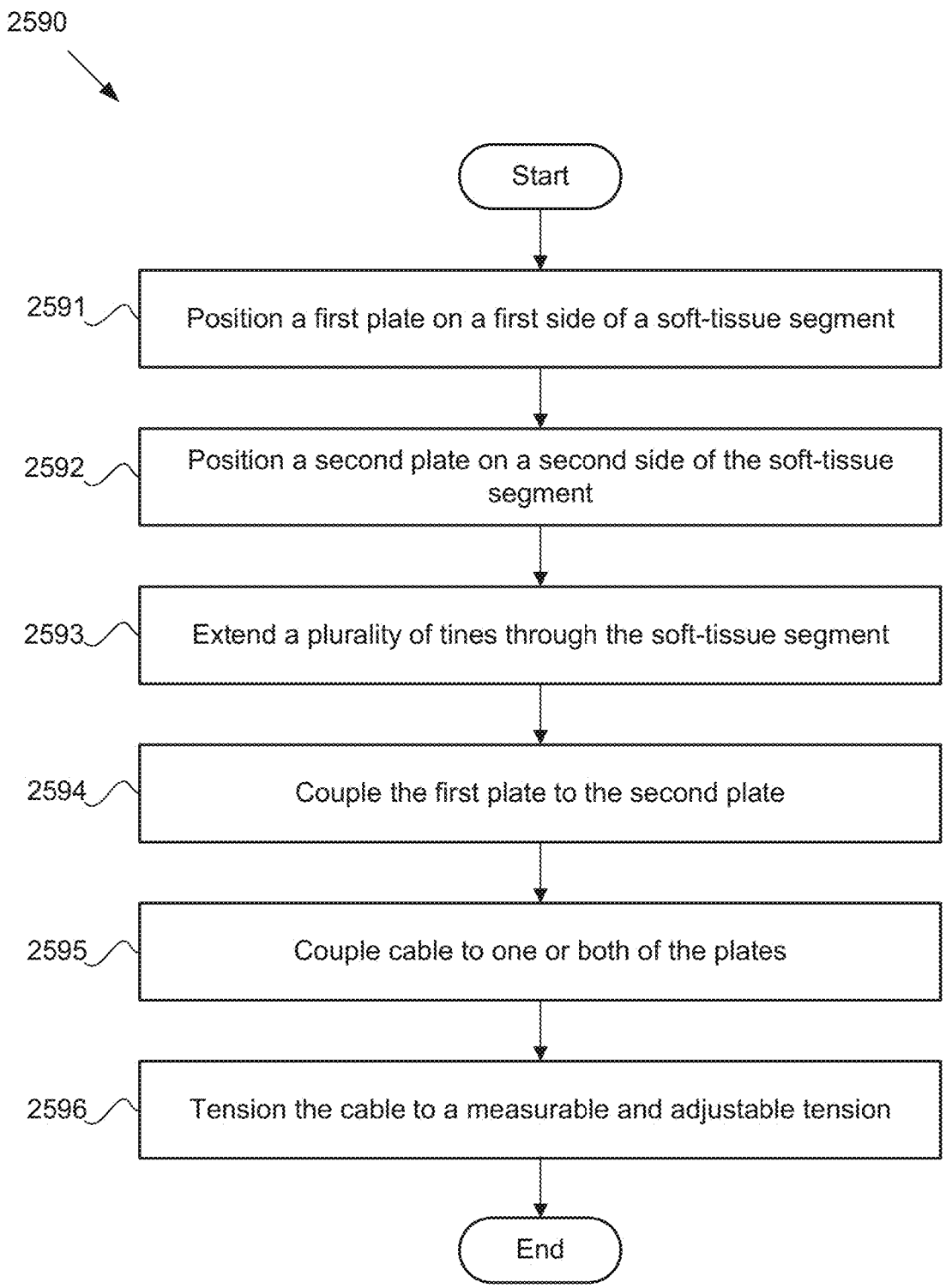
FIG. 19 is a schematic flowchart diagram of a method for repairing a damaged or torn soft-tissue, according to one embodiment.

FIG. 19 is a schematic flowchart diagram of a method 2590 for stapling a soft-tissue segment. The method 2590 includes positioning the first plate on the first side of the soft-tissue segment at 2591 and positioning the second plate on the second side of the soft-tissue segment at 2592. The method 2590 further includes extending the plurality of tines through the soft-tissue segment at 2593 and then subsequently coupling the first plate to the second plate by engaging at least one spacing member of one of the first plate and the second plate with at least one engagement feature of the other of the first plate and the second plate at 2594. Engagement between the at least one spacing member and the at least one engagement feature maintains a predetermined distance between the first clamping surface and the second clamping surface that is more than a length of any one of the tines.

In one embodiment, the soft-tissue segment is a first soft-tissue segment and positioning the first plate on the first side of the first soft-tissue segment includes positioning the first plate on a first side of a second soft-tissue segment. In such an embodiment, positioning the second plate on the second side of the first soft-tissue segment includes positioning the second plate on a second side of the second soft-tissue segment. Accordingly, extending the plurality of tines through the first soft-tissue segment includes extending a first grouping of the plurality of tines through only the first soft-tissue segment, extending a second grouping of the plurality of tines through only the second soft-tissue segment, and extending a third grouping of the plurality of tines through both the first and second soft-tissue segments to couple the first and second soft-tissue segments together. In other words, the first and second soft-tissues segments are partially overlapped before being secured together. The method 2590 further includes coupling a cable to one or both of the first or second plates, which may include extending a cable through a cable-hole in one of the first or second plates, at 2595 and tensioning the cable to fixate the soft-tissue fixation device relative to an object at 2596. In one embodiment, the method 2590 may optionally include releasing and re-tensioning the cable to the same or a different measurable and adjustable tension.

Figure 20:
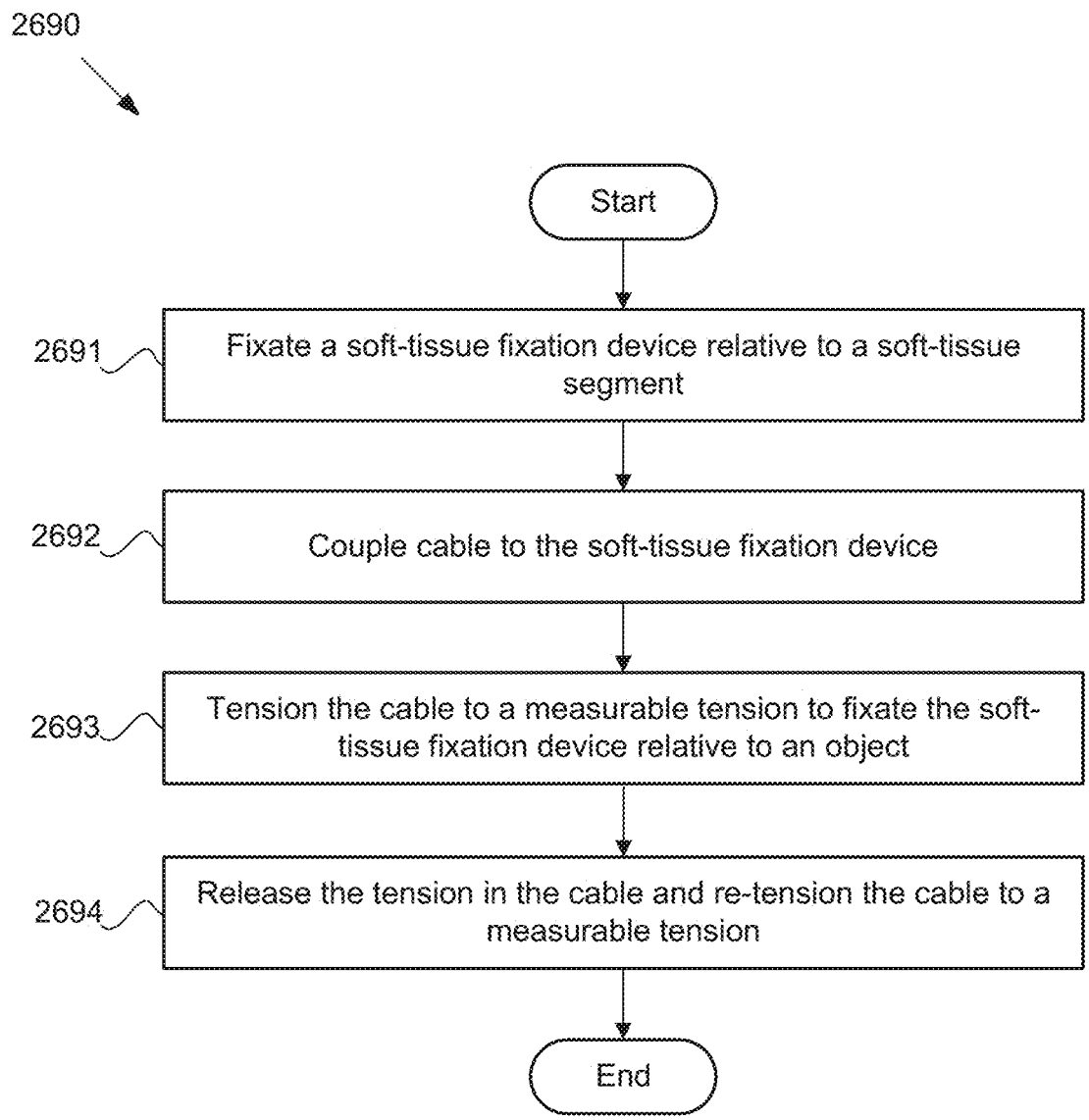
FIG. 20 is a schematic flow chart diagram of one embodiment of a method for fixating soft-tissue relative to bone.

FIG. 20 is a schematic flow chart diagram of one embodiment of a method 2690 for fixating soft-tissue relative to bone. The method 2690 includes fixating a soft-tissue fixation device relative to a soft-tissue segment at 2691, coupling a cable to the soft-tissue fixation device at 2692, and tensioning the cable to a measurable and adjustable tension to fixate the soft-tissue fixation device relative to an object at 2693.

As described above with reference to method 2590, method 2690 may optionally include, after the cable is tensioned to a measurable and adjustable tension, releasing the tension in the cable and re-tensioning the cable to the same or different measurable and adjustable tension. Releasing the tension in the cable may include unlocking a lock that is configured to maintain the cable in tension. The ability to release tension in a cable and subsequently re-tension the cable provides various advantages, such as, for example, facilitating re-use of the cable on other targeted areas of the body in one or more subsequent procedures, in some implementations, and adjustment to the tension or position of the cable on the same targeted area of the body in the same or a subsequent procedure, in other implementations.

Cable Washers

Illustrated in FIGS. 21A-24B are several representative embodiments of a washer for supporting a cable extending from a hole (e.g., a tunnel, passage, or passageway) in a bone, As described herein, the washer for supporting the cable provides various advantages and benefits over other medical tools and procedures. However, the recited advantages are not meant to be limiting in any way, as one skilled in the art will appreciate that other advantages may also be realized upon practicing the present disclosure.

Figure 21A:
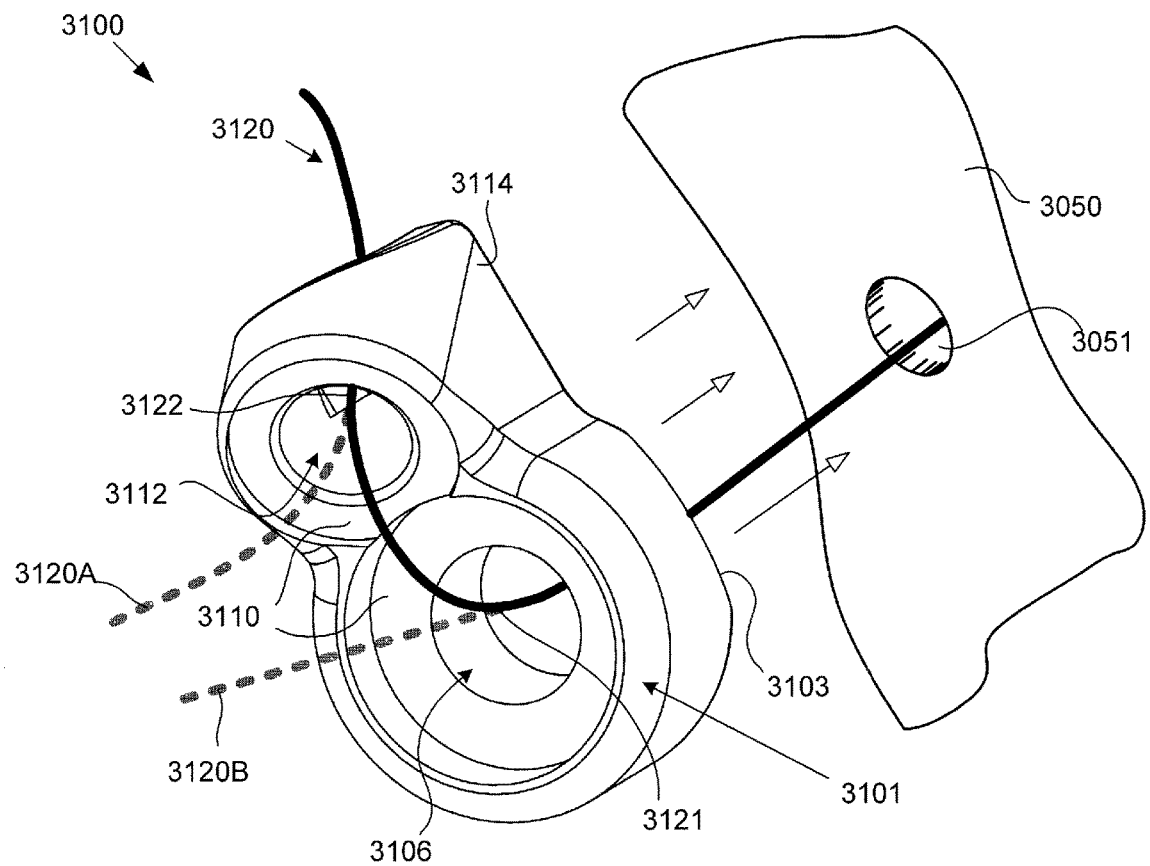
FIG. 21A is a top perspective view of a washer for supporting a cable extending from a hole in a bone, with the washer having a pass-through aperture and a channel, according to one embodiment.
Figure 21B:
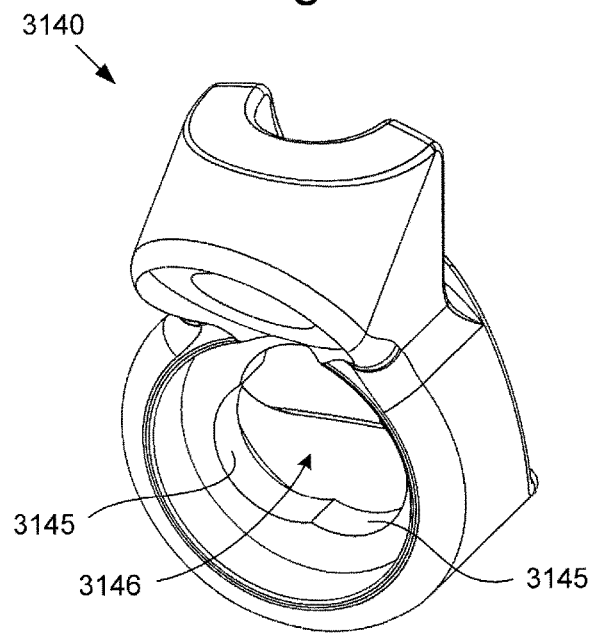
FIG. 21B is a top perspective view of another embodiment of the washer for supporting a cable extending from a hole in a bone, with the washer having a non-circular pass-through aperture.
Figure 21C:
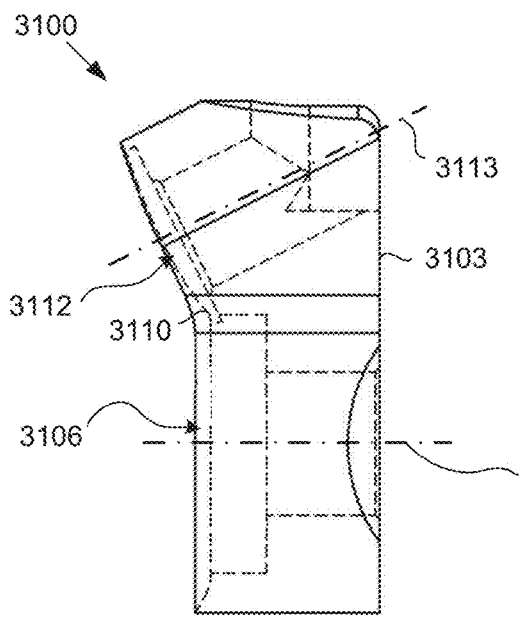
FIG. 21C is a side view of the washer of FIG. 21A, according to one embodiment.

FIG. 21A is a top perspective view of the washer 3100 for supporting a cable 3120 extending from a hole 3051 in a bone 3050, according to one embodiment. The washer 3100 includes a bone-engaging surface 3103 and a cable-engaging surface 3110 opposing the bone-engaging surface 3103. The washer 3100 further includes a pass-through aperture 3106 extending through the washer 3100 and a channel 3112 extending through the washer 3100. The extension direction of the pass-through aperture 3106 is along a first axis 3107 (FIG. 21C) and the extension direction of the channel 3112 is along a second axis 3113 that is at least one of non-parallel to or offset from the first axis 3107. In one embodiment, the channel 3112 extends from a location proximate the pass-through aperture 3106. The pass-through aperture 3106 of the washer 3100 in FIG. 21A has a substantially circular cross-section. According to another embodiment, as depicted in FIG. 21B, the pass-through aperture 3106 of the washer 3140 has a non-circular cross-section. For example, sidewalls 3145 of the pass-through aperture 3106 can form a lobed-shape (e.g., three lobes), thus allowing greater flexibility when positioning the washer 3140 over the hole 3051 in the bone 3050.

The washer 3100 is configured to be positioned directly adjacent (e.g., abutting) the bone 3050 so as to cover the hole 3051 in the bone 3050. For depiction clarity, the washer 3100 in FIG. 21A is shown a distance removed from the bone 3050, but directional arrows indicate how the washer 3100, during use, will be positioned to directly contact the surface of the bone 3050 proximate the hole 3051. The cable 3120 extends from the hole 3051 and passes through the pass-through aperture 3106, across the cable-engaging surface 3110, and through the channel 3112. A first portion 3121 of the cable 3120 is disposed in the pass-through aperture 3106 and a second portion 3122 of the cable 3120 is disposed in the channel 3112. In this manner, the washer 3100 is configured to redirect the cable 3120 after extending out from the hole 3051.

As defined herein, the term "cable" refers to a cord-like element, such as a wire, filament, weave, or thread, whether bundled or individual, that is capable of holding a measurable and adjustable tension and causing a measurable and adjustable compression of bone. In other words, the tension in the cable can be measured, such as by a tension measuring device, and can be adjusted, such as after an initial tensioning of the cable. When used to compress bone (e.g., to compress two bone segments together), the measured tension in the cable is equal to a measured compression of the bone. Thus, as used herein, a measured and adjustable tension of a cable is synonymous with a measured and adjustable compression of bone by the cable.

In one embodiment, the measurable and adjustable tension may be a specific, known, predictable, expected, controllable, anticipated, desired, repeatable, sustainable, and/or predeterminable tension. For example, the cable 3120 may be passed through a pass-through hole in a bone and may be tensioned to a measurable and adjustable tension in order to facilitate the reduction and fixation of fractures or to otherwise facilitate the repair of dislocations or soft-tissue damage. In other words, the cable 3120 is not a conventional suture or conventional thread material, since such materials are incapable of, or at least not well-suited for, maintaining a measurable and adjustable tension. Thus, the term "cable" refers to a flexible yet substantially non-stretchable element that can be tensioned to a measurable and adjustable tension. Because the cable 3120 is capable of maintaining or retaining a measurable and adjustable tension, the effectiveness and reproducibility of successful surgical procedures is improved. In other words, different surgical procedures relating to different bones in the body may involve different degrees of retention/fixation force (e.g., the fixation force required to reduce a fracture in the femur may be greater than the fixation force required to reduce a fracture in the patella). Accordingly, the ability of the cable 3120 to be tensioned to a measurable and adjustable tension improves the reliability and reproducibility of surgical procedures when compared with other medical procedures that do not utilize cables. The cable 3120 may be made from any one of various materials. For example, in specific implementations, the cable 3120 is made from metal, such as stainless steel, titanium, or other metal.

As introduced above in the Background section, cables can be used to suture torn tissue back together and/or to hold bone fragments securely in place. For example, one end of a cable may be anchored to a bone while the other end of the cable is wrapped around the bone to provide external reinforcement after the fractured bone has been set (e.g., a cerclage configuration). In another example, a cable may be used to couple the bone to a soft-tissue segment or to another bone. The washer 3100 described herein is specifically configured to engage and support a cable 3120 as it changes directions upon extending from a hole 3051 in a bone 3050. In other words, the washer 3100 facilitates a change in the direction of the cable 3120 by mitigating wear and damage to the bone 3050 that would otherwise occur if the washer 3100 were not employed. Also, cables may be tensioned in order to adequately hold the various tissues in place. Accordingly, if the washer 3100 was not employed to cover the hole 3051, the tensioned cable, extending in a different direction upon exiting the hole 3051, would potentially cut into the edge of the bone defining the hole 3051, causing the patient to experience pain and/or causing the surgery to be compromised as the cable loses tension, cuts through the bone, or fractures the bone. In other words, the washer 3100 prevents the cable 3120 from directly contacting and potentially damaging the edge of the hole 3051 in the bone 3050 and also engages the cable 3120 within the channel 3112 to direct and retain the cable 3120 in a desired direction (e.g., across the surface of the bone).

In order for the cable 3120 to be tensioned, the opposing end of the cable (e.g., the end of the cable that extends into the hole 3051 of the bone 3050) must be anchored or securely retained. In one embodiment, the cable 3120 is coupled to a bone anchor that has been installed in the hole 3051 or on an opposite side of the bone 3050. In another embodiment, the opposing end of the cable 3120 has a stop, such as a crimp body, that is engageable with the opposing surface of the bone proximate the opposite opening of the hole, thus preventing the cable 3120 from sliding through the hole in the bone 3050 and thereby ensuring that the cable 3120 remains securely anchored.

In another embodiment, two separate cables 3120A, 3120B (depicted as dashed lines) each extends through a respective one of the pass-through aperture 3106 and the channel 3112. In such an embodiment, to retain the cables 3120A, 3120B in place relative to the washer 3100, a crimp body (not shown) may be crimped to each of the cables 3120A, 120B. The crimp body can be configured to engage the cable-engaging surface 3110 of the washer 3100 (e.g., nestably engage or be seated on the cable-engaging surface 3110), thereby retaining the cables 3120A, 3120B in place relative to the washer 3100. In one implementation, the cable 3120B is retained on the washer 3100 and extends through the hole 3051 in the bone 3050, and the cable 3120A is retained on the washer 3100 and extends around (e.g., to cerclage) the bone 3050. In yet another implementation, one end of a cable can extend through the hole 3051 in the bone 3050 and the pass-through aperture 3106, and be retained to the washer 3100 by a crimp body, and another end of the same cable can wrap around the bone 3050, pass through the channel 3112, and be retained to the washer 3100 by a separate crimp body.

As described above, the pass-through aperture 3106 of the washer 3100 extends along the first axis 3107 and the channel 3112 extends along the second axis 3113. The channel 3112 is specifically configured to direct the cable 3120 in a specific direction and prevent the cable from inadvertently slipping laterally across the surface of the bone 3050.

According to the depicted embodiment, the first and second axes 3107, 3113 are non-parallel. In one embodiment, the first axis 3107 is perpendicular to the second axis 3113. In another embodiment, a minor angle between the first axis 3107 and the second axis 3113 is less than 45 degrees. In yet another embodiment, the minor angle between the first axis 3107 and the second axis 3113 is about 30 degrees. In another embodiment, the angle between the first axis 3107 and the second axis 3113 may be dependent on the configuration and dimensions of the bone (e.g., the angle between the first and second axes may be greater than 90 degrees).

As described above, the pass-through aperture 3106 and the channel 3112 extend along the first axis 3107 and second axis 3113, respectively. The washer 3100 may be configured to have a specific angle between the first and second axes 3107, 3113 that corresponds with the specific dimensions of the bone 3050 and that corresponds with the desired extension direction of the cable 3120 after it exits the hole 3051 of the bone 3050. Nevertheless, despite a practitioner's intent to match the desired extension direction of the second portion 3122 of the cable 3120 with the second axis 3113 of the channel 3112, the direction of the cable and the second axis 3113 may not be parallel. In other words, the extension directions of the first and second portions 3121, 3122 of the cable 3120 are not necessarily parallel with the first and second axes 3107, 3113 of the pass-through aperture 3106 and the channel 3112. For example, the first portion 3121 of the cable 3120 may extend at an angle relative to the first axis 3107 through the pass-through aperture 3106 and/or the second portion 3122 of the cable 3120 may extend at an angle relative to the second axis 3113 of the cable 3120 through the channel 3112. The extent of the offset between the extension direction of the cable and the first and second axes may be based on the relative sizes of the diameter of cable 3120 and the cross-sectional dimensions of the pass-through aperture 3106 and channel 3112.

The cable-engaging surface 3110 is the portion of the washer 3100 upon which the cable 3120 is directly engaged as it transitions between the pass-through aperture 3106 and the channel 3112. The cable-engaging surface 3110 may be smooth and/or have rounded edges and corners to prevent wear on the cable 3120. In one embodiment, as described in greater detail below with reference to FIGS. 24A and 24B, the cable-engaging surface 3110 may have a groove that further facilitates the proper and secure engagement between the cable 3120 and the washer 3100.

Figure 21D:
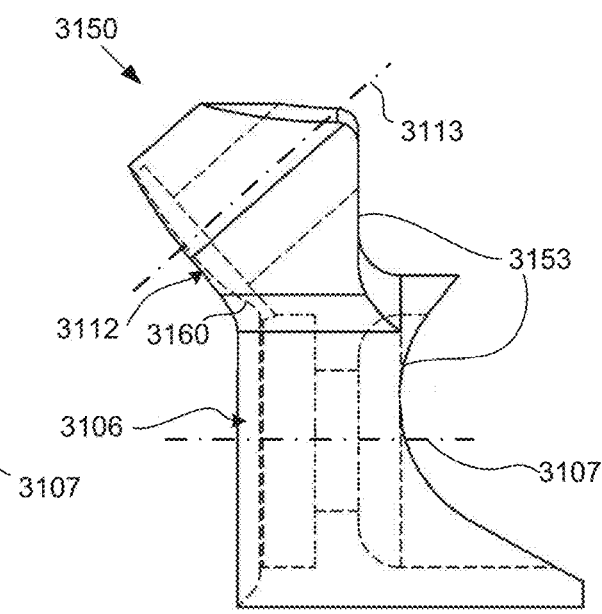
FIG. 21D is a side view of the washer, with the washer having a contoured bone-engagement surface complimentary to the shape of a bone, according to one embodiment.

The bone-engaging surface 3103, opposite the cable-engaging surface 3110, is the portion of the washer 3100 that directly contacts the bone 3050. In one embodiment, the cable-engaging surface and the bone-engaging surface are substantially parallel. In another embodiment, the bone-engaging surface 3103 is substantially coplanar. In yet another embodiment, the bone-engaging surface 3153 may be specifically shaped and designed to conform to and/or complement the surface shape of the bone 3050 upon which it is engaged. For example, the side view of the washer 3150 in FIG. 21D shows the bone-engaging surface 3153 having undulations or indents that correspond with a specific shape of the bone against which the washer 3150 will be positioned.

The footprint of the washer 3100, according to the depicted embodiments, is non-circular. In other words, the washer may include an arm 3114 extending radially outward away from a main body 3101 of the washer, through which the pass-through aperture 3106 extends, with the channel 3112 extending from proximate the pass-through aperture through the arm 3114. Also, according to the depicted embodiment, at least a portion of the channel 3112 is circumferentially closed. In another embodiment, the channel may be open (i.e., only partially circumferentially closed) as described in greater detail below with reference to FIGS. 24A and 24B.

Figure 22A:
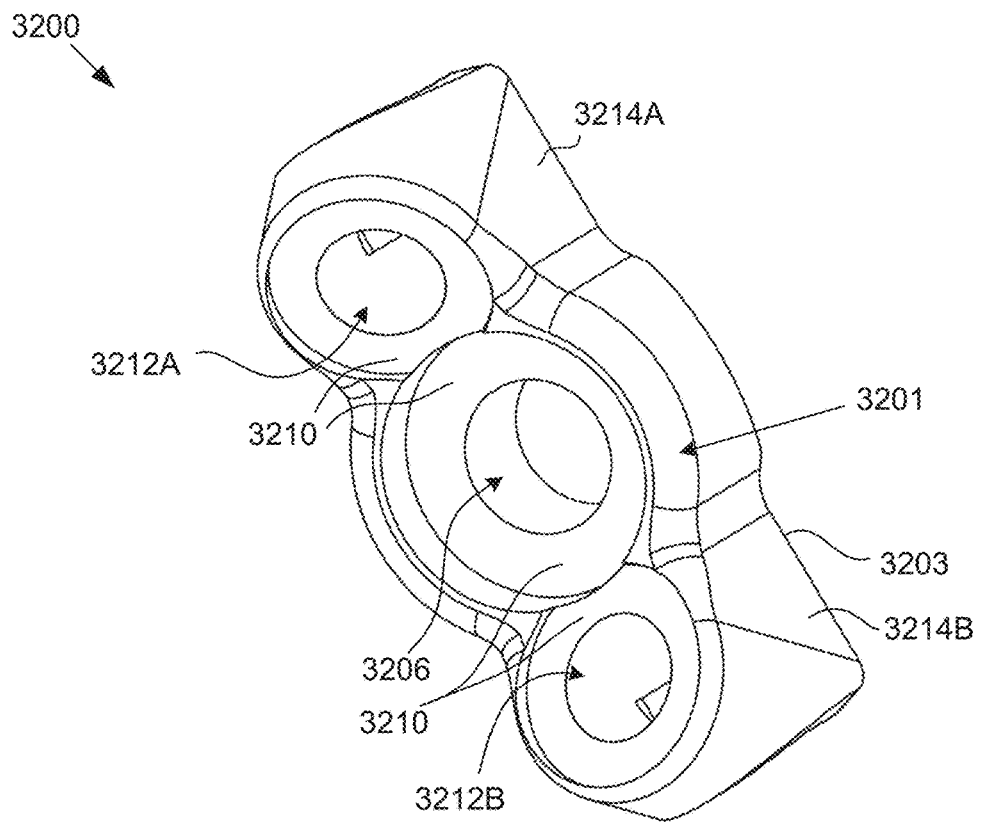
FIG. 22A is a top perspective view of the washer, with the washer having two channels, according to one embodiment.
Figure 22B:
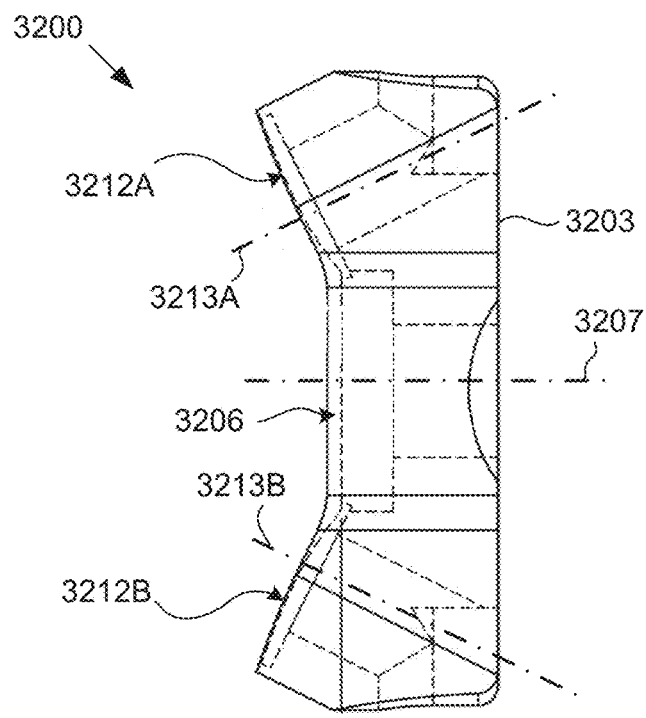
FIG. 22B is a side view of the washer of FIG. 22A, according to one embodiment.
Figure 22C:
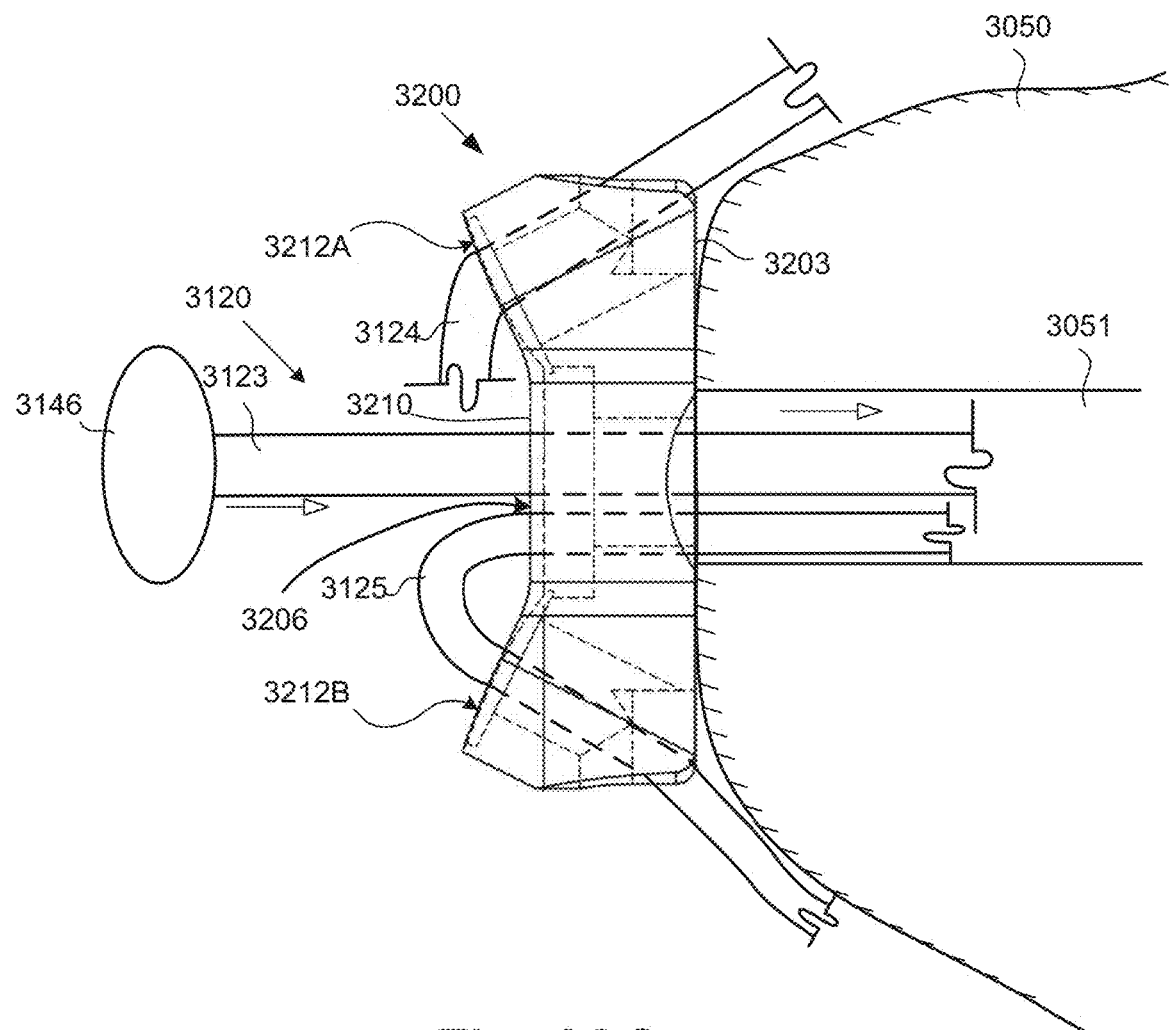
FIG. 22C is a side view of the washer of FIG. 22A showing a first portion of the cable having an affixed stop that seats against the cable-engaging surface of the washer; according to one embodiment.
Figure 22D:
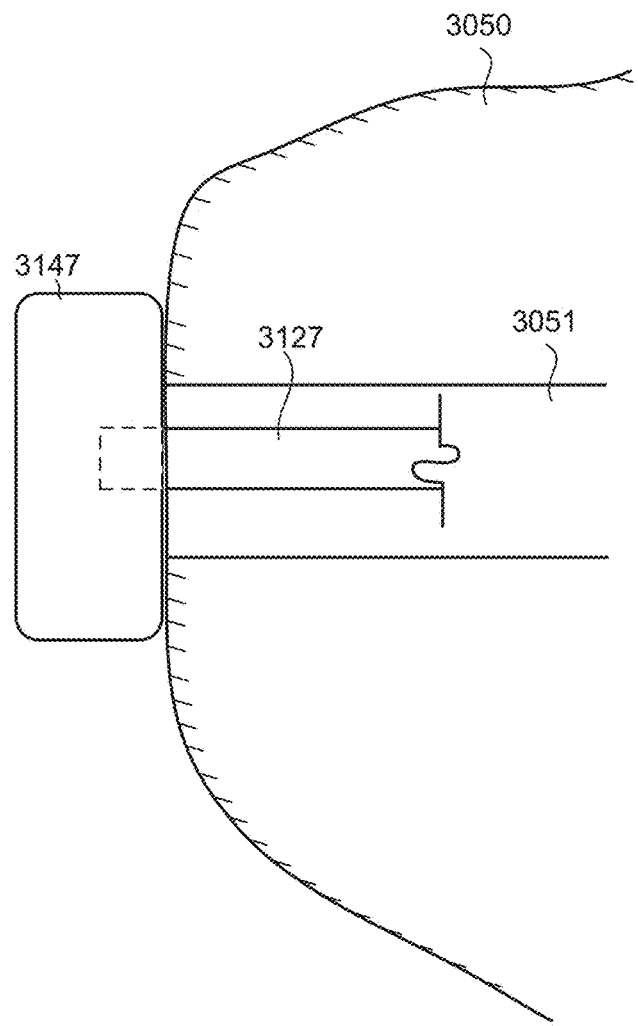
FIG. 22D is a schematic side view of a stop having a cable pre-attached to the stop.
Figure 23:
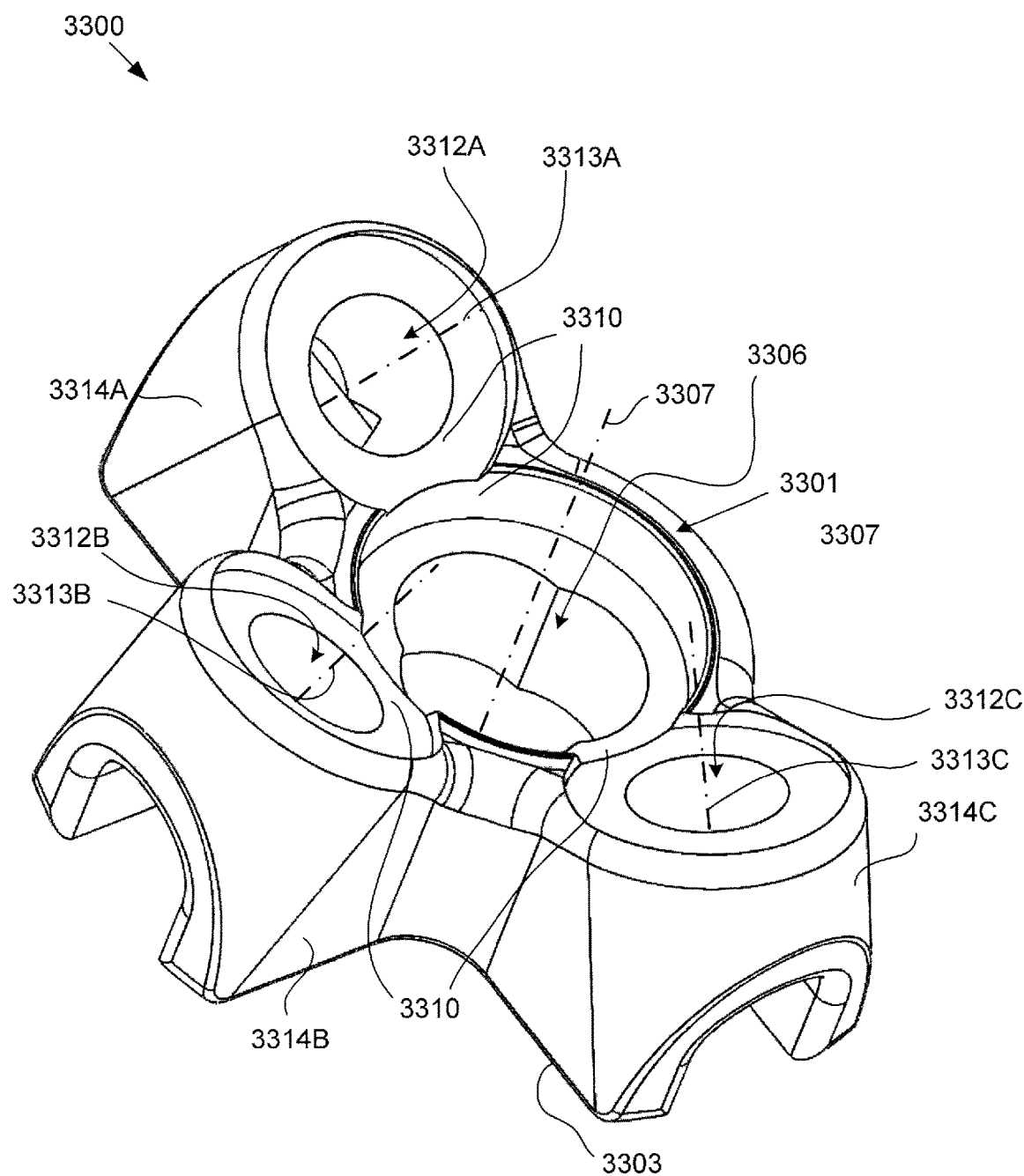
FIG. 23 is a top perspective view of the washer, with the washer having three channels, according to one embodiment.

FIGS. 22A-23 show various embodiments of the washer having multiple channels. More specifically, FIGS. 22A and 22B show a top perspective view and a side view, respectively, of one embodiment of the washer 3200 with two channels 3212A, 3212B while FIG. 23 shows a top perspective view of the washer 3300 with three channels 3312A, 3312B, 3312C.

The washer 3200 in FIGS. 22A and 22B has the pass-through aperture 3206 disposed in between the two arms 3214A, 3214B, each arm having one of the channels 3212A, 3212B. In one embodiment, the two axes 3213A, 3213B of the channels 3212A, 3212B extend in mirror image directions (i.e., both angles are the same relative to the first axis 3207 of the pass-through aperture 3206). In another embodiment, however, the two axes 3213A, 3213B of the channels 3212A, 3212B extend in different directions relative to the first axis 3207 of the pass-through apertures 3206. In other words, the first channel 3212A on the first arm 3214A of the washer 3200 may be configured to extend the cable in a direction, relative to the first axis 3207, that is different than the second channel 3212B in the second arm 3214B of the washer 3200 based on the specific dimensions and shape of the bone 3050.

FIG. 22C is a side view of the washer 3200 of FIG. 22A showing a first portion 3123 of the cable 3120 having a stop 3146 affixed to an end of the cable 3120. The stop 3146 is configured to seat against the cable-engaging surface 3210 of the washer 3200. The direction arrows in FIG. 22C show the direction the cable 3120 is pulled through the pass-through aperture 3206 of the washer 3200 to move the stop 3146 into seated engagement with the washer 3200. After a portion of the cable is passed through the pass-through aperture 3206 of the washer 3200, the portion of the cable 3120 may be passed through a hole in the bone and/or wrapped around bone. A pulling force may be exerted on the cable 3120 to tension the cable 3120 to a measurable tension. Furthermore, after passing through a hole in the bone and tensioned, a free end of the cable 3120 can be locked and/or crimped to retain the tension in the cable. In some implementations, the pass-through hole 3051 extends through two bone segments of a fractured bone such that tensioning the cable 3120 to a measurable and adjustable tension in this manner causes the two bone segments to compress together with a measurable and adjustable compression. Moreover, because the cable 3120 passes through the bone, as opposed to around the bone, the compression of the two bone segments is applied in one direction (e.g., unidirectionally) concentric with the cable 3120, to more uniformly and evenly distribute the compressive load to the bone segments, as opposed to multiple directions when compression is applied by a cable passing around the bone.

As defined herein, a stop is any of various features, such as nuts, clips, conventional washers, pins, balls, caps, lids, or the like, that are attachable to a cable and capable of engaging an opening (e.g., a surface adjacent to or defining the opening) to prevent further passage of the cable through the opening. In one embodiment, the stop 3146, shown schematically in FIG. 22C, is spherical or rounded. In another embodiment, the stop 3146 resembles a flange or conventional washer, and has a shape that complements the shape of the cable engaging surface 3210 of the washer 3200 such that the stop 3146 is configured to nestably engage the washer 3200. According to yet another embodiment, the stop 3146 is at least partially deformable to compliment the shape of the cable-engaging surface 3210 of the washer 3210 as the cable 3120 is tensioned.

The stop 3146 can be integrated into or permanently attached to a first end portion 3123 of the cable 3120. For example, the stop 3146 may be swaged, crimped, welded, bonded, or otherwise fixedly secured to the cable 3120. In another embodiment, the stop 3146 can be detachably coupled to the cable 3120, thus allowing for stops with different shapes, dimensions, angles, etc. to be alternatively coupled to the same cable as desired.

Referring again to FIG. 22C, after or prior to the cable 3120 being passed through the washer 3200 and the stop 3146 seating on the washer 3200, other cables, such as cable 3124, 3125, can pass through any of the channels or aperture of the washer 3200 such that the washer can be used to redirect other cables passing through or around the bone. Alternatively, after passing through the hole in the bone, the cable 3120 may wrap around or pass back through the hole in the bone to again engage and be redirected by the washer 3200 (e.g., the representations of the cable 3124, 3125 could be opposing ends of the cable 3120 after the cable 3120 has passed through the hole in the bone in the direction indicated).

FIG. 22D is a schematic side view of a stop 3147 having a cable 3127 pre-attached. In one embodiment, the stop 3147 has a cross-sectional dimension that is larger than the diameter of the hole 3051 in the bone 3050, thereby preventing the stop 3147 from passing through the hole 3051. In one embodiment, the stop 3147 is a disk-like stop, analogous to the stop 3146 described above. For example, the stop 3147 can directly engage the surface of the bone 3050 or the stop 3147 can be seated in a separate washer that is analogous to the washers described herein. In another embodiment, the stop 3147 has features that are analogous to the washers described herein, but with a pre-attached cable 3127.

The washer 300 in FIG. 23 has three arms 3314A, 3314B, 3314C extending radially outward from the main body 3301 of the washer 3300, with three channels 3312A, 3312B, 3312C that all extend along non-parallel axes 3313A, 3313B, 3313C relative to the first axis 3307 of the pass-through aperture 3306. The bone-engaging surface 3303 of the arms 3314A, 3314B, 3314C of the washer 3300 may be substantially co-planar with each other but may extend outward away from the pass-through aperture 3306 at 90 degrees from each other (thereby leaving 180 degrees between two of the arms 3314A, 3314B, 3314C). In another embodiment, the arms 3314A, 3314B, 3314C are still substantially coplanar but are equally spaced apart in their extension directions (i.e., 120 degrees between adjacent arms). In yet another embodiment, the arms 3314A, 3314B, 3314C are not coplanar, with one arm having a different relative elevation in order to complement the shape of the surface of the bone 3050. For example, the arms 3314A, 3314B, 3314C may have different relative vertical elevations and/or the arms 3314A, 3314B, 3314C may be contoured to complement to a specific shape/dimension of a bone.

In another embodiment, four or more arms, each with its own channel, may extend outward away from the main body of the washer, through which the pass-through aperture extends. Alternatively, the washer may include multiple pass-through apertures with multiple arms extending from each pass-through aperture. In other words, the washer may resemble a panel that is configured to span a comparatively larger span of bone surface for a more extensive surgical procedure. In one embodiment, one or more cables may be pre-attached to the washer, as described above with reference to FIG. 22D.

Figure 24A:
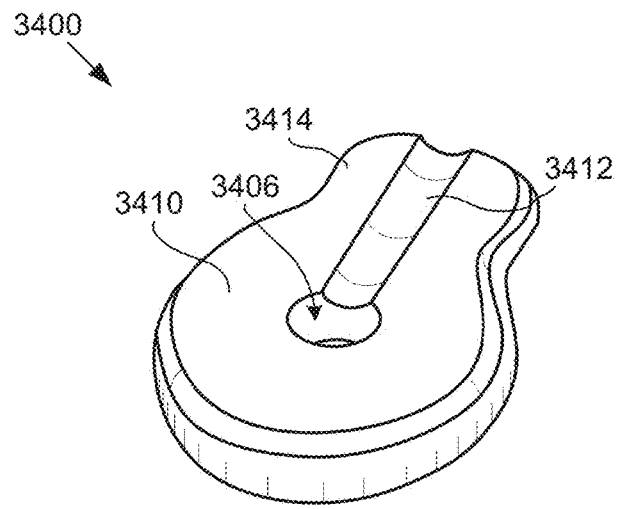
FIG. 24A is a top perspective view of the washer, with the channel of the washer being a groove in the cable-engaging surface extending to a peripheral edge of the washer, according to one embodiment.

FIG. 24A is a top perspective view of the washer 3400, with the groove 3412 of the washer being an open groove in the cable-engaging surface 3410 extending to a peripheral edge of the washer 3400. In such an embodiment, with the cable received within the groove 3412, the cable is prevented from moving laterally but is not prevented from slipping out of engagement with the groove 3412 if the cable experiences an upward away force, relative to the cable-engaging surface, that moves the cable out of the groove 3412.

Figure 24B:
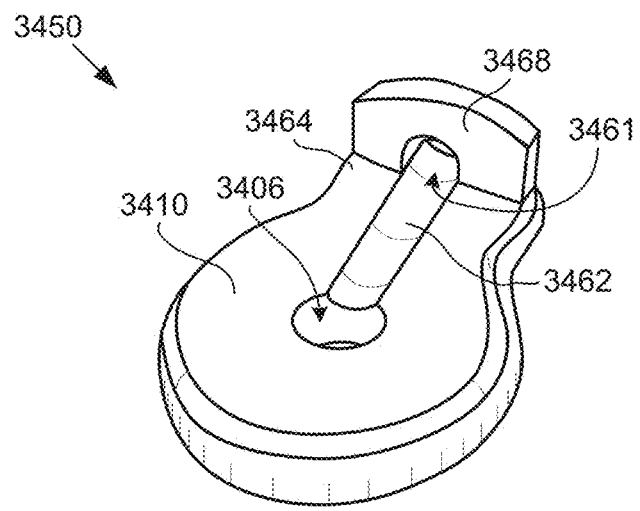
FIG. 24B is a top perspective view of the washer, with a portion of the channel of the washer being circumferentially enclosed, according to one embodiment.

FIG. 24B is a top perspective view of the washer 3450, with a portion 3468 of the groove 3462 of the washer 3450 being circumferentially closed. In such an embodiment, the circumferentially closed portion 3468 is a protruding lip extending away from the cable-engaging surface 3410. In one embodiment, the circumferentially closed portion 3468 of the groove 3462 includes a crimping mechanism that enables the cable passing through circumferentially closed portion to be crimped and secured to the washer 3450. In one embodiment, the circumferentially closed portion 3468 is not disposed near the edge of the washer 3450 but instead is disposed comparatively closer to the aperture 3406 or alternatively spans the entire length of the groove 3462.

Figure 25:
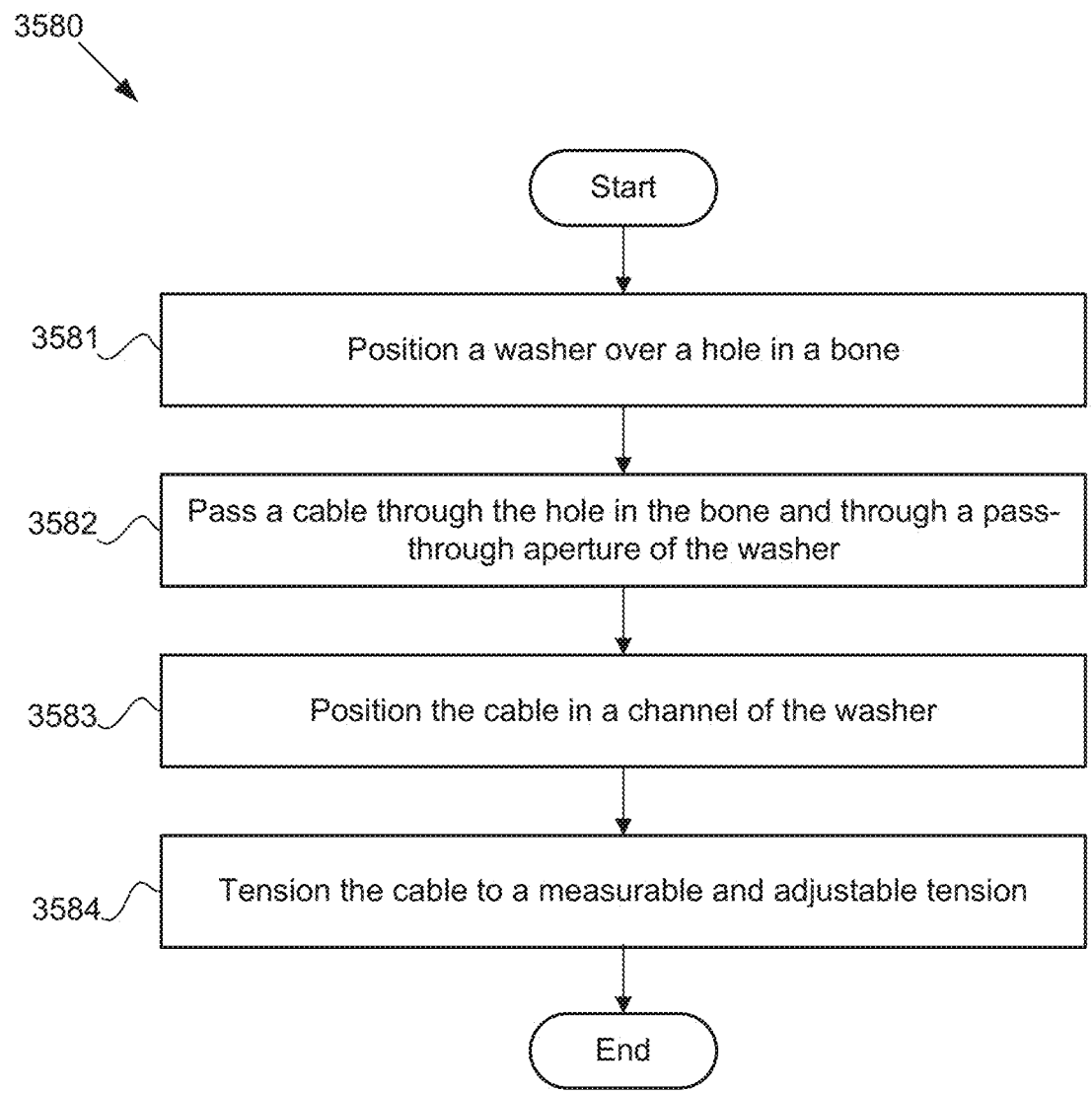
FIG. 25 is a schematic flowchart diagram of a method using the washer to support a cable extending from a hole in a bone.

FIG. 25 is a schematic flowchart diagram of one embodiment of a method 3580 for using the washer to support a cable extending from the bone. The method 3580 includes positioning the washer over the hole in the bone such that the bone-engaging surface of the washer engages the surface of the bone adjacent the hole at 3581. The method 3580 further includes passing the cable through the hole in the bone and through the pass-through aperture in the washer extending along a first axis from the bone engaging surface to a cable-engaging surface at 3582. Still further, the method 3580 includes positioning the cable in the channel of the washer with the channel extending along a second axis that is at least one of non-parallel to or offset from the first axis at 3583.

In one embodiment, positioning the cable in the channel includes passing the cable through a circumferentially closed portion of the channel. In such a configuration, the method 3580 further includes crimping the cable in the circumferentially closed portion of the channel. The method 3580 also includes tensioning the cable, to a measurable and adjustable tension, after passing the cable through the hole in the bone and after positioning the cable in the channel of the washer at 3584, to cause a measurable and adjustable compression of the bone by the cable in some implementations. In one embodiment, the method 3580 may further include releasing and re-tensioning the cable to the same or a different measurable and adjustable tension.

Figure 26:
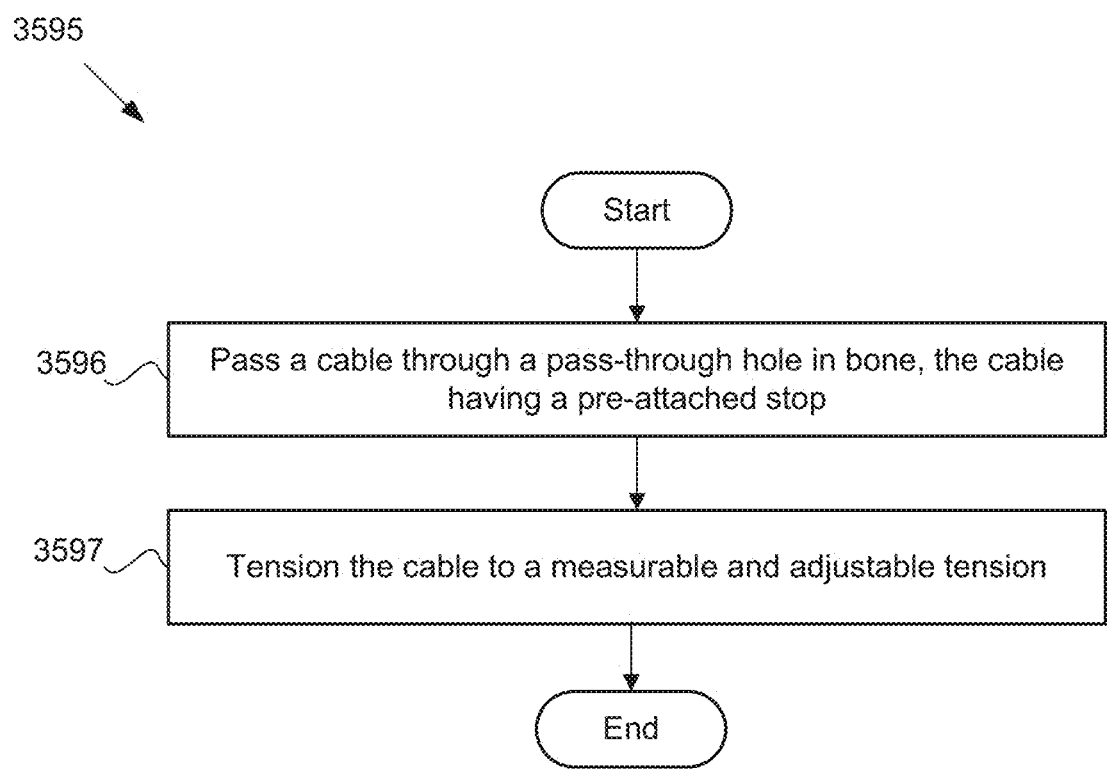
FIG. 26 is a schematic flowchart diagram of one embodiment of a method for extending a cable through a pass-through hole in a bone.

FIG. 26 is a schematic flowchart diagram of one embodiment of a method 3595 for extending a cable through a pass-through hole in a bone. The method 3595 includes passing a cable through the pass-through hole in the bone, with the cable having a stop that is pre-attached at 3596. The method 3595 further includes tensioning the cable to a measurable and adjustable tension and 3597, to cause a measurable and adjustable compression of the bone by the cable in some implementations. In one embodiment, before tensioning the cable, the method 3595 further includes positioning a washer over the pass-through hole in the bone so that a bone-engaging surface of the washer engages a surface of the bone adjacent the pass-through hole and passing the cable through a pass-through aperture in the washer extending along a first axis from the bone engaging surface to a cable-engaging surface. The method further may include seating the stop against a complimentary shape of the cable-engaging surface of the washer (e.g. as described above with reference to FIG. 22C). In one implementation, the stop is a washer and the method 3595 further includes redirecting one or more additional cables or an opposite end portion of the cable across a cable-engaging surface of the washer.

As mentioned above with reference to method 580, method 595 may optionally include, after the cable is tensioned to a measurable and adjustable tension, releasing the tension in the cable and re-tensioning the cable to the same or different measurable and adjustable tension. Releasing the tension in the cable may include unlocking a lock that is configured to maintain the cable in tension. The ability to release tension in a cable and subsequently re-tension the cable provides various advantages, such as, for example, facilitating re-use of the cable on other targeted areas of the body in one or more subsequent procedures, in some implementations, and adjustment to the tension or position of the cable on the same targeted area of the body in the same or a subsequent procedure, in other implementations.

Tensioning, Crimping, Cutting Cable

Illustrated in FIGS. 27-35 are several representative embodiments of an apparatus 4100 for attaching a crimp body 4105 to a cable. As described herein, the apparatus for attaching the crimp body to the cable provides various advantages and benefits over other medical tools and procedures. However, the recited advantages are not meant to be limiting in any way, as one skilled in the art will appreciate that other advantages may also be realized upon practicing the present disclosure.

Figure 27:
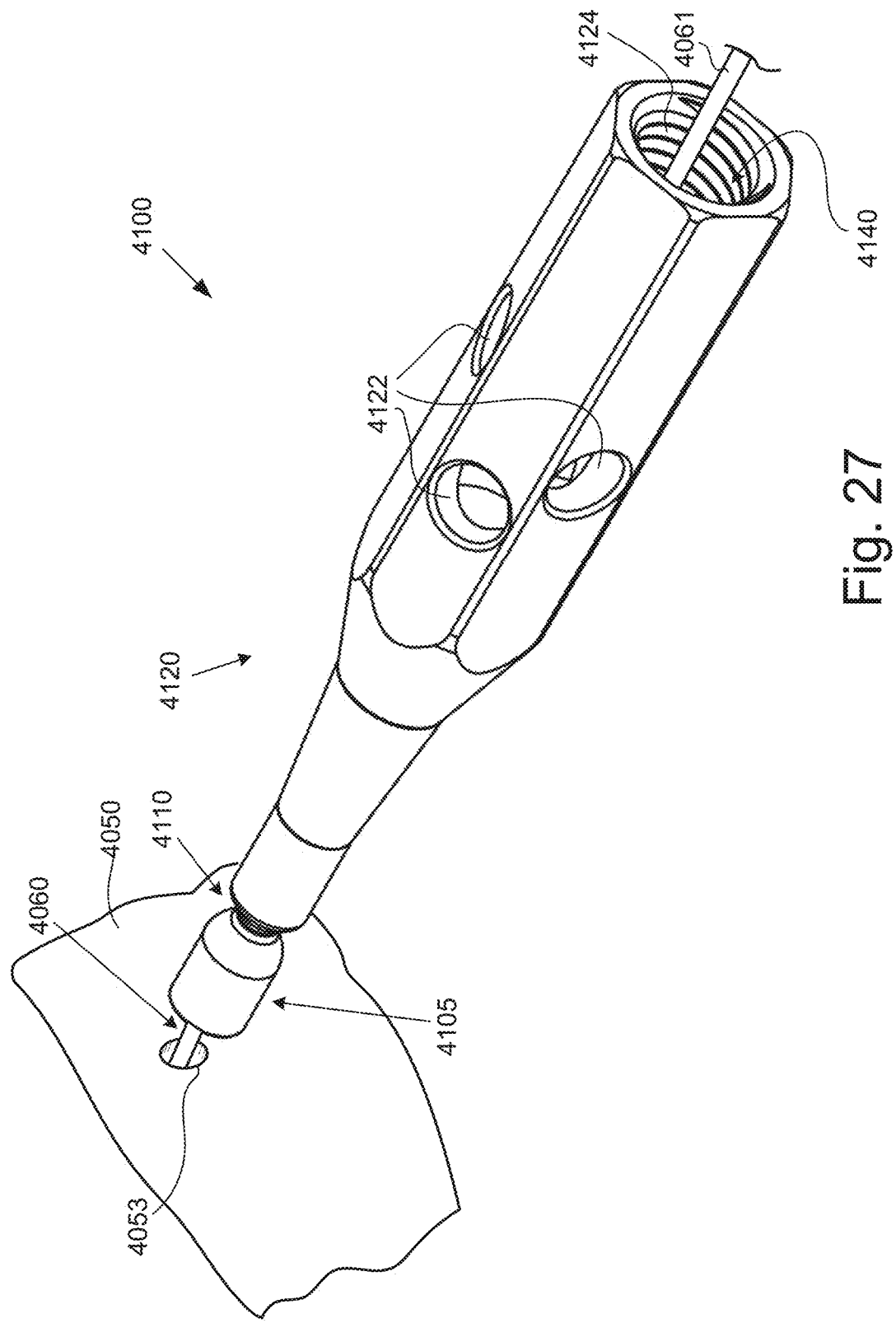
FIG. 27 is side perspective view of an apparatus for attaching a crimp body to a cable, with the apparatus including a crimp body, a neck, and an elongate shaft, according to one embodiment.

FIG. 27 is a perspective view of one embodiment of the apparatus 4100 for attaching the crimp body 4105 to a cable. The apparatus 4100 includes the crimp body 4105, a neck 4110, and an elongate shaft 4120. The neck 4110 is interposed between the crimp body 4105 and the elongate shaft 4120. A continuous central passage 4140 extends through the crimp body 4105, neck 4110, and elongate shaft 4120 such that the cable 4060 is concurrently positionable within the crimp body 4105, neck 4110, and elongate shaft 4120 via the central passage 4140. In one embodiment, at least two of the crimp body 4105, the neck 4110, and the elongate shaft 4120 are integrated together to form a one-piece monolithic construction. For example, the crimp body 4105 and the neck 4110 may be formed together as one-piece monolithic construction that is separately coupled to the elongate shaft 4120. Alternatively, as an example, the crimp body 4105, the neck 4110, and the elongate shaft 4120 may all be formed together as a one-piece monolithic construction.

As defined herein, the term "cable" refers to a cord-like element, such as a wire, filament, weave, or thread, whether bundled or individual, that is capable of holding a measurable and adjustable tension and causing a measurable and adjustable compression of bone. In other words, the tension in the cable can be measured, such as by a tension measuring device, and can be adjusted, such as after an initial tensioning of the cable. When used to compress bone (e.g., to compress two bone segments together), the measured tension in the cable is equal to a measured compression of the bone. Thus, as used herein, a measured and adjustable tension of a cable is synonymous with a measured and adjustable compression of bone by the cable.

In one embodiment, the measurable and adjustable tension may be a specific, known, predictable, expected, controllable, anticipated, desired, repeatable, sustainable, and/or predeterminable tension. For example, the cable 4060 may be passed through a pass-through hole (e.g., a tunnel, passage, or passageway) in a bone and may be tensioned to a measurable and adjustable tension in order to facilitate the reduction and fixation of fractures or to otherwise facilitate the repair of dislocations or soft-tissue damage. In other words, the cable 4060 is not a conventional suture or conventional thread material, since such materials are incapable of, or at least not well-suited for, maintaining a measurable and adjustable tension. Thus, the term "cable" can refer to a flexible, yet substantially non-stretchable, elongate cord-like element that can be tensioned to a measurable and adjustable tension. Because the cable 4060 is capable of maintaining or retaining a measurable and adjustable tension, the effectiveness and reproducibility of successful surgical procedures is improved. In other words, different surgical procedures relating to different bones in the body may involve different degrees of retention/fixation force (e.g., the fixation force required to reduce a fracture in the femur may be greater than the fixation force required to reduce a fracture in the patella). Accordingly, the ability of the cable 4060 to be tensioned to a measurable and adjustable tension improves the reliability and reproducibility of surgical procedures when compared with other medical procedures that do not utilize cables. The cable 4060 may be made from any one of various materials. For example, in specific implementations, the cable 4060 is made from metal, such as stainless steel, titanium, or other metal.

Generally, the apparatus 4100 enables a practitioner (e.g., a surgeon or other medical professional) to feed a cable 4060 already extending from a hole 4053 in a bone 4050 through the central passage 4140 of the apparatus 4100 (i.e., the cable 4060 is passed through the crimp body 4105, the neck 4110, and the elongate shaft 4120). The practitioner then positions the crimp body 4105 adjacent the bone, proximate the opening of the hole 4053 in the bone 4050, and tensions the cable 4060 extending through central passage 4140 of the apparatus 4100 (i.e., the cable extends through the crimp body 4105, the neck 4110, and the elongate shaft 4120). As described in greater detail below, the cable 4060 may be tensioned manually by hand (e.g., pulling on a portion 4061 of the cable 4060 protruding from back side of the elongate shaft 4120) or a tensioner device may be employed to exert a specified tension on the cable. In order for the cable to be tensioned, the opposing end of the cable must be anchored or securely retained. In one embodiment, the cable 4060 may be coupled to a bone anchor that has been installed in a bone or on the surface of a bone. In another embodiment, the opposing end of the cable 4060 has an attached crimp body or some other type of retainer feature that is engageable with the opposing surface of the bone proximate the opposite opening of the hole 4053, thus preventing the cable from sliding through the hole in the bone and thereby ensuring that the cable holds tension.

With the cable tensioned and the crimp body 4105 positioned adjacent the bone 4050, proximate the opening of the hole 4053 in the bone 4050, the practitioner can crimp the crimp body 4105 to the cable 4060, detach the crimp body 4105 from the elongate shaft 4120 by cutting the apparatus 4100 at the neck 4110, and cut the cable 4060. According to one embodiment, crimping the crimp body 4105 is performed first, but the two steps of cutting the neck 4110 and cutting the cable 4060 may be performed concurrently or sequentially. For example, a cutting tool may cut both the neck 4110 and the cable 4060 extending through the neck 4110 in a single cutting action. In another embodiment, as shown in FIG. 35, a single tool 4270 may be used to both crimp, the crimp body 4105, and cut, the neck 4110 and cable, in a single action. Moreover, in some implementations, the tool 4270 may fit over at least a portion of the apparatus and/or be coaxial with the apparatus.

Although a single tool 4270 is shown in FIG. 35, it is recognized that separate tools can be used. For example a first tool may be used to crimp the crimp body and a second tool may be used to cut the cable. However, in such an embodiment, the crimping would need to still occur before cutting the cable to avoid losing the tension in the cable. Since the cross-sectional dimension of the crimp body 4105 is larger than the diameter of the hole 4053 in the bone 4050, after the cable 4060 is cut the portion of the cable extending through the hole 4053 in the bone 4050 holds the tension since the crimp body 4105 prevents the cable 4060 from withdrawing into the hole 4053 in the bone 4050.

Although the depiction in FIG. 27 shows the crimp body 4105 positioned a distance away from the opening of the hole 4053 in the bone 4050, in one embodiment the crimp body 4105 is positioned in direct contact with the surface of the bone 4050 surrounding the opening of the hole 4053, thereby preventing any slack (e.g., loss of tension) in the cable 4060 upon cutting the cable 4060. In another embodiment, the crimp body 4105 is shaped and formed to nestably engage the cable-engaging surface of the cable washers described above (e.g., the cable-engaging surface 3110 of the washer 3100 in shown in FIG. 21A) in order to maintain tension in the cable 4060.

The apparatus has advantages over conventional tools and procedures. For example, the elongate shaft 4120 provides a way for the practitioner to easily position the crimp body 4105 into direct contact with the bone 4050 without requiring the practitioner's hands to be inserted into the surgical area to hold a traditional crimp ball/feature in place. Further, a tensioner device may be mounted to the elongate shaft 4120, thus allowing the tensioner device to be removed a distance away from the surgical tissue. Additional details relating to the method of using the apparatus, as well as details regarding additional components of the apparatus, are included below with reference to the remaining figures.

According to the embodiment shown in FIG. 27, the outer-periphery of the elongate shaft 4120 is non-circular and the elongate shaft 4120 has internal threads 4124 and one or more pass-through apertures 4122. The internal threads 4124 and the pass-through apertures 4122 are optional in certain implementations. Nevertheless, the internal threads 4124 and pass-through apertures 4122 are shown in FIGS. 27-29 in order to clearly disclose an alternative embodiment that is described below with reference to FIGS. 30-35.

As shown in the embodiment depicted in FIGS. 27-29, a maximum cross-sectional dimension of the crimp body 4105 is larger than a maximum cross-sectional dimension of the neck 4110 and a maximum cross-sectional dimension of the elongate shaft 4120 is larger than the maximum cross-sectional dimension of the crimp body 4105. The neck 4110 may be configured to have a small cross-sectional dimension to allow the neck 4110 to be easily cut. Also, the elongate shaft 4120 may have a comparatively larger cross-sectional dimension to allow the practitioner to easily grasp the apparatus 4100 or to allow room for a locking mechanism to be positioned within the central passage 4140 of the elongate shaft 4120. In an alternative embodiment, the apparatus may have a substantially uniform cross-sectional dimension along its length. The locking mechanism may be configured to lock the cable extending through the central passage 4140, thus preventing the cable 4060 from moving through the central passage 4140 and also holding any tension that may have been imparted to the cable 4060. In one embodiment, a set screw threadably engages with the elongate shaft and can be rotated into contact with the cable 4060 to lock the cable 4060 in place relative to the apparatus 4100 in order to retain any tension imparted to the cable 4060. In such an embodiment, the set screw can be subsequently loosened to allow the cable to be re-tensioned and re-locked. In another embodiment, for example, a collet member 4260, as described below with reference to FIGS. 30-35, may be used as the locking mechanism.

The apparatus 4100 may be constructed of various materials. For example, the apparatus 4100 may be constructed from metals such as stainless steel or synthetic materials such as plastics, polymers, or composites. In one embodiment, different elements 4105, 4110, 4120 of the apparatus 4100 may be constructed from different materials. In one embodiment, the apparatus 4100 is disposable. In another embodiment, the elongate shaft 4120 may be configured to be reusable by attaching a new crimp body to the elongate shaft 4120.

FIGS. 28 and 29 are a side view and cross-sectional side view, respectively, of the apparatus 4100 of FIG. 27, but with a washer 4103 disposed adjacent the crimp body 4105. As described above, the crimp body 4105 is configured to engage the hole 4053 in the bone 4050 to prevent the cable 4060 from withdrawing into the hole 4053 and thereby holding the tension in the cable 4060. According to the embodiment shown in FIGS. 28 and 29, the washer 4103 is disposed at the end of the apparatus 4100 (i.e., the crimp body 4105 is interposed between the washer 4103 and neck 4110). The washer 4103 may further facilitate a proper engagement with the surface of the bone 4050 surrounding the opening of the hole 4053.

In one embodiment, at least two of the crimp body 4105, neck 4110, elongate shaft 4120, and washer 4103 are integrated to form a one-piece monolithic construction. In one implementation, all four of the crimp body 4105, neck 4110, elongate shaft 4120, and washer 4103 are integrated to form a one-piece monolithic construction. In some implementations, for example, the washer 4103, crimp body 4105, and neck 4110 may be formed together as a one-piece monolithic construction that is coupled to the elongate shaft 4120. In one embodiment, the washer 4103 is integrated with the crimp body 4105 to form a one-piece monolithic construction with the crimp body 4105. In another embodiment, the washer 4103 is detachable or detached from the apparatus 4100.

In one embodiment, the washer 4103 may include one or more pre-embedded cables that can be extended across or through the surface of the bone 4050. For example, a first end portion 4102A of the pre-embedded cable may be fixed to the washer 4103 (e.g. secured within a channel formed in the washer 4103 and a second portion 4102B of the cable may be wrapped around the bone (e.g., in a cerclage configuration) and/or extended through the hole in the bone. With the second portion 4102B of the cable wrapped around and/or extend through the bone, the second portion 4102B of the cable can then be inserted through the central passage 4140 of the apparatus 4100 to be crimped, cut, and tensioned. In one embodiment, the pre-embedded cable 4102 extends from an outer edge of the washer 4103. The pre-embedded cable may be used to wrap around tissue (e.g., cerclage configuration) to facilitate the reduction and fixation of a fracture. In another embodiment, the channel(s) of the washer 4103 may pass-through the entire washer, thus allowing one or more cables to pass through the washer.

According to the embodiment shown in FIG. 29, the central passage 4140 has an interior surface 4128 that converges in a direction extending from the elongate shaft 4120 to the crimp body 4105. Such a feature is described in greater detail below with reference to FIGS. 30-35. In one embodiment, locking mechanism elements may extend through the pass-through apertures 4122 to engage the cable 4060 and lock the cable 4060 in place, thereby holding the tension in the cable 4060. For example, one or more of the pass-through apertures 4122 may have threads that allow one or more set screws or other similar elements to extend transversely into the central passage 4140 to securely lock the cable 4060 in place.

Figure 30:
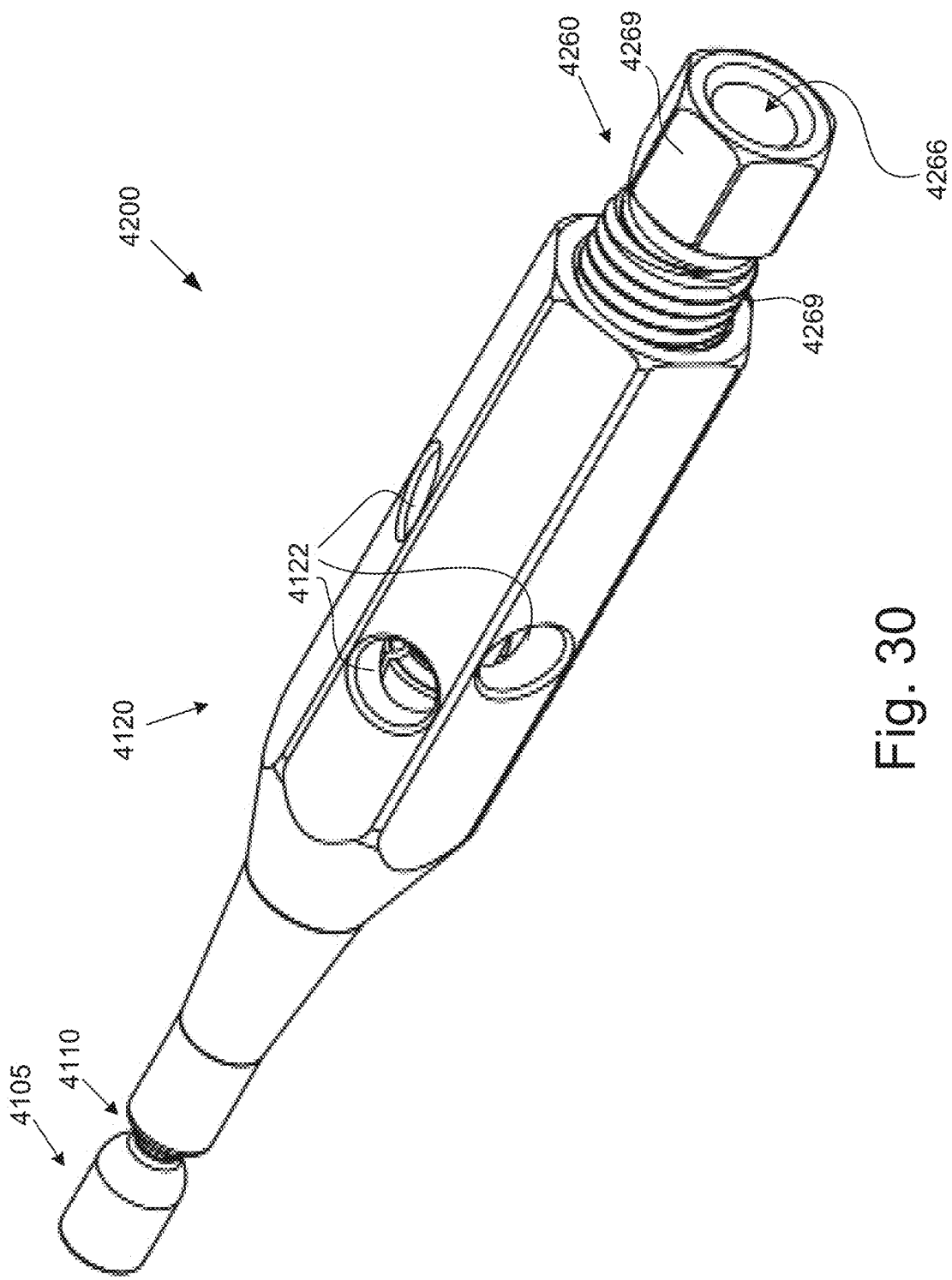
FIG. 30 is a side perspective view of another embodiment of the apparatus, with a collet member partially disposed within a central passage of the elongate shaft.
Figure 31:
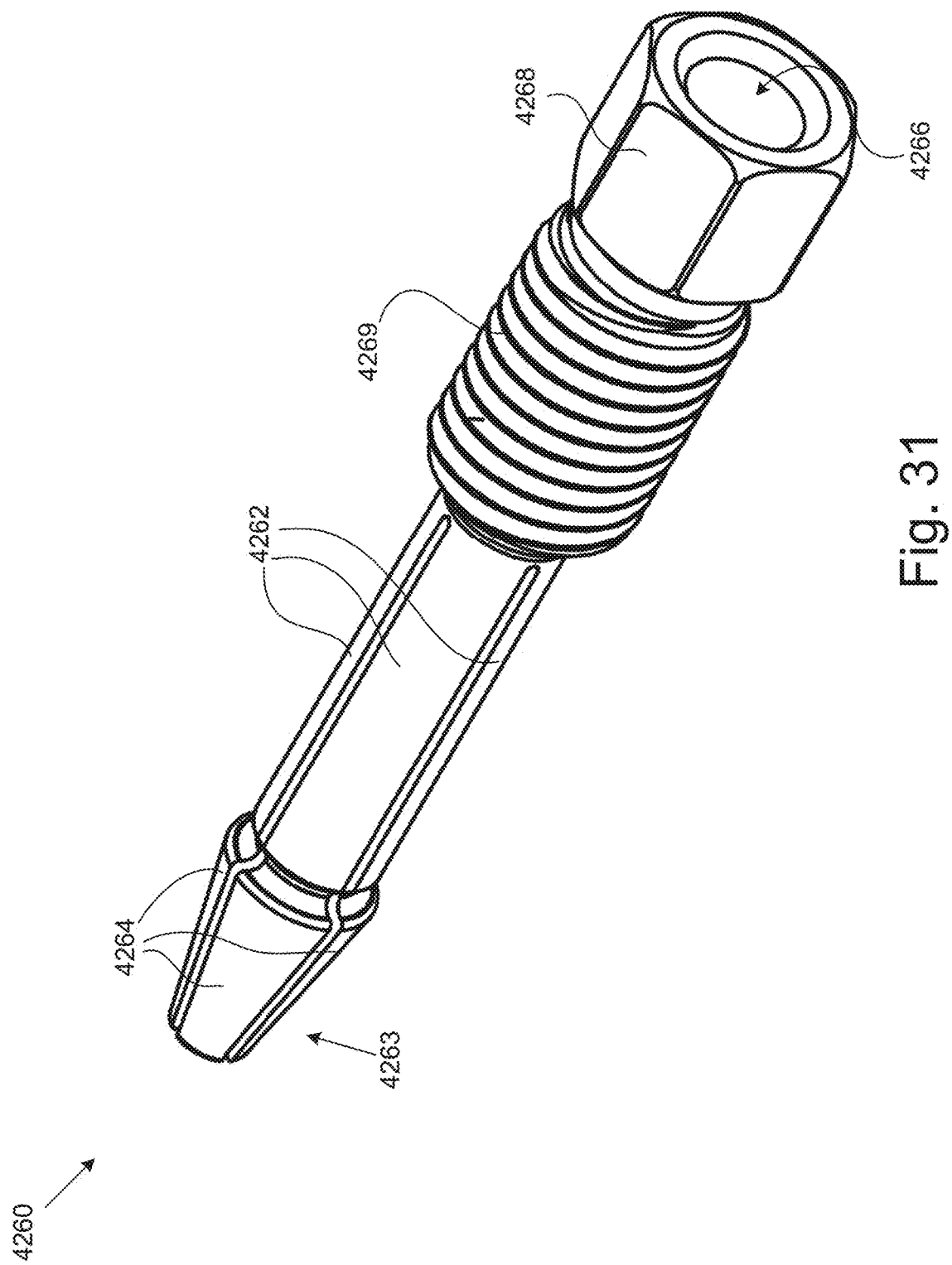
FIG. 31 is a side perspective view of the collet member, according to one embodiment.

FIG. 30 is a side perspective view of another embodiment of the apparatus 4200 with a collet member 4260 partially disposed within the central passage 4140 of the elongate shaft 4120. FIGS. 31-33 show a side perspective view, a side view, and a cross-sectional side view, respectively, of the collet member 4260 and FIGS. 34 and 35 show a side view and a cross-sectional side view, respectively, of the apparatus 4200 depicted in FIG. 30.

The collet member 4260 is a type of locking mechanism that is configured to clamp around the cable 4060 to securely maintain the tension in the cable 4060. The collet member 4260 is translationally movable within the central passage 4140 of the elongate shaft 4120. The collet member 4260 has a central channel 4266 extending through a plurality of prongs 4262 (FIGS. 31-33), with the central channel 4266 being concentric with the central passage 4140. The plurality of prongs 4262 are configured to engage the interior surface 4128 of the central passage 4140 of the elongate shaft 4120 and compress inwardly towards the central channel 4266 to lock the cable 4060 positioned in the central channel 4266. In other words, relative translational movement along the central axis 4126 of the collet member 4260 with respect to the elongate shaft 4120 causes the plurality of prongs 4262 to move into direct contact with the converging interior surface 4128 of the central passage 4140. As the collet member 4260 continues its translational movement, the plurality of prongs 4262 are flex inwards by the converging interior surface 4128. As the plurality of prongs 4262 are flexed inwards towards the central channel 4266, through which the cable 4060 is extending, the plurality of prongs 4262 clamp around the cable 4060 to prevent the cable from slipping or losing tension. With the cable 4060 secured, the manually applied tension may be relieved or the tensioner device may be detached from the apparatus 4200. In another embodiment, the collet member 4260 can be moved backwards, thus allowing the plurality of prongs 4262 to flex back outwards in order for the cable 4060 to be released or re-tensioned.

According to the embodiment depicted in the figures, the collet member has external threads 4269 that are threadably engageable with the conforming internal threads 4124 disposed in the central passage 4140 of the elongate shaft 4120. Relative rotation of the collet member 4260 with respect to the elongate shaft 4120, accomplished via rotational engagement of the conforming threads 4269, 4124, causes the collet member 4260 to translationally move within the central passage 4140 of the elongate shaft 4120 and thereby apply the clamping force around the cable 4060.

The pass-through apertures 4122 extending through one or more walls of the elongate shaft 4120 in a direction substantially perpendicular to the central axis 4126 of the elongate shaft are configured, according to one embodiment, to receive a tool (e.g., transverse shaft) for inducing relative rotation between the elongate shaft 4120 and the collet member 4260. In another embodiment, the pass-through apertures 4122 include secondary locking features that facilitate and improve the security of the clamping force of the collet member 4260 around the cable 4060. For example, one or more set screws may be threaded through the pass-through apertures 4122 to engage the collet member 4260, thus preventing the collet member 4260 from inadvertently sliding away from the converging interior surface 4128 and thereby preventing the plurality of prongs 4262 from losing a secure clamp around the cable 4060.

As shown in the figures and according to one embodiment, the collet member 4260 has a proximal-end portion 4268 that has a non-circular outer periphery. The non-circular outer periphery of the proximal-end portion is mateable with a rotational tool (e.g., a drill or a wrench) for inducing relative rotation between the elongate shaft 4120 and the collet member 4260.

Figure 36:
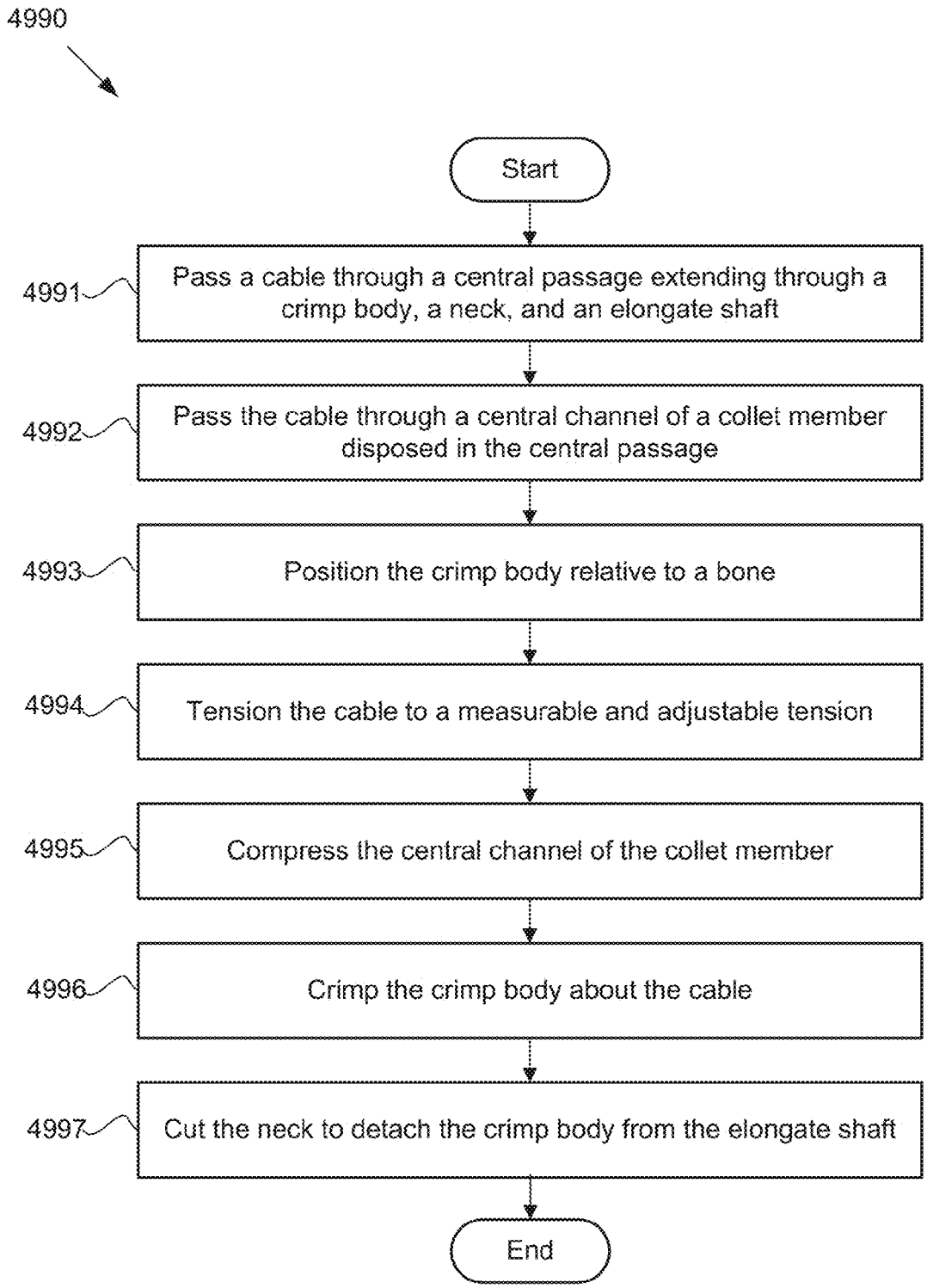
FIG. 36 is a schematic flowchart diagram of a method for attaching the crimp body to the cable, according to one embodiment.

FIG. 36 is a schematic flowchart diagram of one embodiment of a method 4990 for attaching the crimp body 4105 to the cable 4060. The method 4990 includes passing the cable 4060 through the central passage 4140 that continuously extends through the crimp body 4105, the elongate shaft 4120, and the neck 4110 at 4991. Optionally, the method 4990 further includes passing the cable 4060 through the central channel 4266 of the collet member 4260 disposed within and concentric with the central passage 4140 of the elongate shaft 4120 at 4992. Still further, the method 4990 includes positioning the crimp body 4105 in a desired position relative to the pre-formed hole 4053 in the bone 4050 at 4993. Because the crimp body 4105 is non-movably coupled with the elongate shaft 4120, the crimp body 4105 can be positioned in the desired position relative to the pre-formed hole 4053 by moving or positioning the elongate shaft 4120. At such a step in the method 4990, the cable 4060 is extending from the hole 4053 and into the central passage 4140. The method 4990 further includes tensioning the cable 4060 to a measurable and adjustable tension at 4994, to cause a measurable and adjustable compression of the bone by the cable in some implementations, and, optionally, compressing the central channel 4266 of the collet member 4260 to lock the cable 4060 at the measurable and adjustable tension at 4995. Before the central channel 4266 is compressed, the crimp body 4105 is positioned in the desired position.

The method 4990 further includes crimping the crimp body 4105 about the cable 4060 at 4996 and then cutting the neck 4110 to detach the crimp body 4105 from the elongate shaft 4120 at 4997. In some implementations, the hole 4053 extends through two bone segments of a fractured bone such that tensioning the cable 4060 to a measurable and adjustable tension, and crimping the cable 4060, in this manner causes the two bone segments to compress together with a measurable and adjustable compression. Moreover, because the cable 4060 passes through the bone, as opposed to around the bone, the compression of the two bone segments is applied in one direction (e.g., unidirectionally) concentric with the cable 4060, to more uniformly and evenly distribute the compressive load to the bone segments, as opposed to multiple directions when compression is applied by a cable passing around the bone.

As mentioned above, crimping the crimp body 4105 and cutting the neck 4110 can be performed in a single action by actuating a dual-purpose crimping/cutting tool 4270. In one embodiment, cutting the neck 4110 at step 4997 includes concurrently cutting the cable 4060 positioned within the central passage 4140 of the neck 4110. In one embodiment, the method 4990 may optionally include, after the cable is tensioned to a measurable and adjustable tension, releasing the tension in the cable and re-tensioning the cable to the same or different measurable and adjustable tension. Releasing the tension in the cable may include unlocking a lock that is configured to maintain the cable in tension. The ability to release tension in a cable and subsequently re-tension the cable provides various advantages, such as, for example, facilitating re-use of the cable on other targeted areas of the body in one or more subsequent procedures, in some implementations, and adjustment to the tension or position of the cable on the same targeted area of the body in the same or a subsequent procedure, in other implementations.

Exemplary Applications

Figure 44:
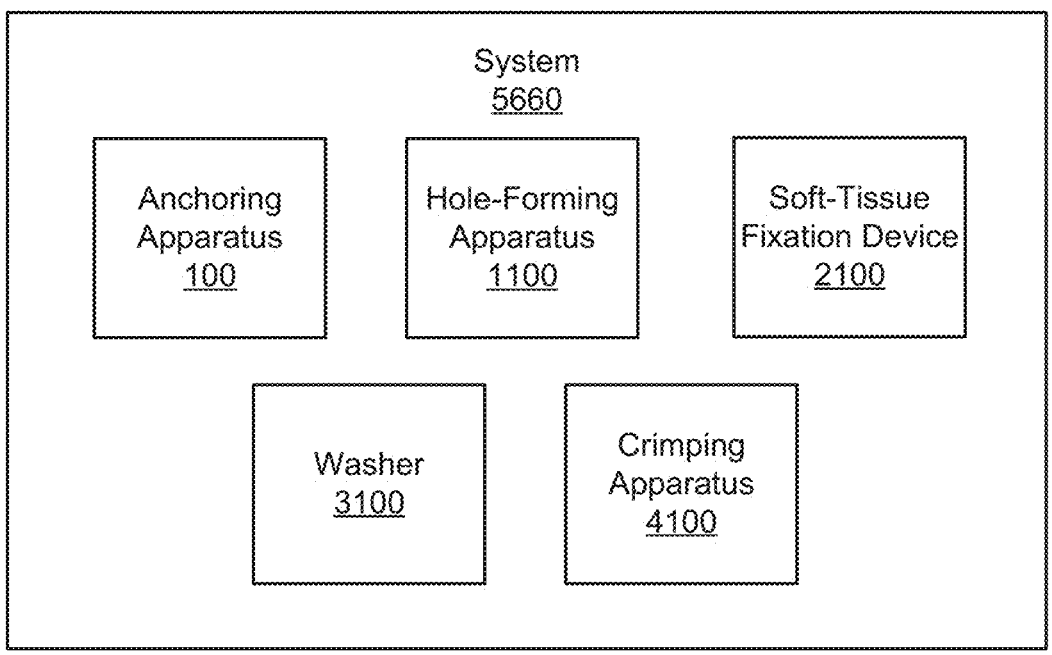
FIG. 44 is a flow chart diagram depicting a system of reducing and stabilizing fractures in bone, subluxations of bones, and dislocations of bones, according to one embodiment.

One or more of the apparatuses, systems, and methods described above may be implemented in any of various ways for reducing and stabilizing fractures in bone, subluxations of bones, and dislocations of bones. For example, any of the apparatuses, systems, and methods described above can be used alone or in combination to achieve a particular result for a particular type of bone-related condition as desired. Generally, in certain implementations, one or more of the apparatuses, systems, and methods described above can be used to tension a cable, relative to bone, to a measurable and adjustable tension for the purpose of compressing bone to a measurable and adjustable compression. In one embodiment, as shown in FIG. 44, a system 5660, or medical procedure kit, for reducing and stabilizing fractures in bone, subluxations of bones, and dislocations of bones includes at least one, and in some implementations all, of the anchoring apparatus 100 for anchoring cable to bone, the hole-forming apparatus 1100 for passing cable through a hole in bone, the soft-tissue fixation device 2100, the washer 3100 for supporting a cable, and the apparatus 4100 for attaching a crimp body to a cable.

Figure 37:
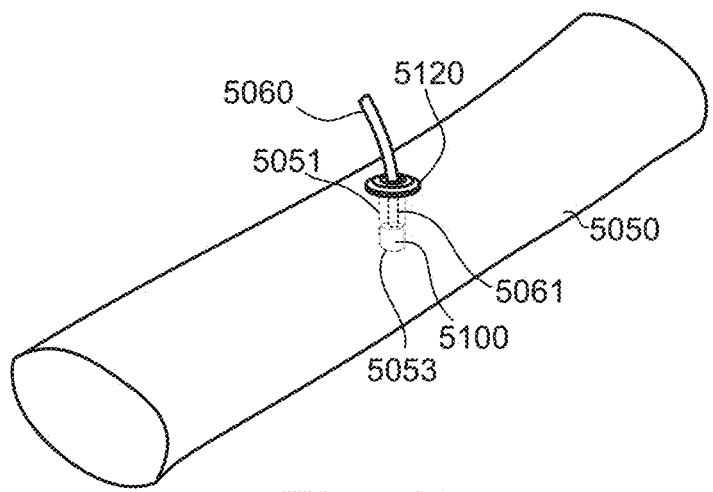
FIG. 37 is a perspective view of a tensioned cable anchored within and extending from a uni-cortical hole formed in a bone, according to one embodiment.

Referring to FIG. 37, according to one embodiment, the system 5660 can be used to tension a cable within a uni-cortical hole in a bone to a measurable and adjustable tension, and thus cause a measurable and adjustable compression of the bone, for the treatment of a bone-related condition. For example, a uni-cortical hole 5051 can be formed in the bone 5050 using any of various hole-forming devices, such as those shown and described herein. The uni-cortical hole 5051 initiates at one outer surface or cortex of the bone 5050 and terminates at a location within the bone. In other words, the uni-cortical hole 5051 has an open end at one outer surface of the bone 5050 and a closed end 5053 at a location within an interior of the bone. Because the uni-cortical hole 5051 does not extend from one outer surface of a bone to an opposing outer surface of the bone, the uni-cortical hole is not considered a bi-cortical or pass-through hole.

Like some of the systems and methods described above, a cable 5060 is positioned within the uni-cortical hole 5051 and subsequently tensioned to a measurable and adjustable tension. However, instead of passing entirely through the bone 5050 from one surface of the bone to another opposing surface of the bone, an end 5061 of the cable 5060 terminates within the bone. As shown, the end 5061 of the cable 5060 is fixedly secured within the uni-cortical hole 5051 formed in the bone 5050 at a location within the bone by an internal fixation device 5100. The internal fixation device 5100 can be any of various fixation devices capable of fixating a cable from a location within a bone. For example, in some implementations, after or while forming the uni-cortical hole 5051 in the bone 5050, the internal fixation device 5100 can be deployed into the uni-cortical hole, such as proximate the closed end 5053 of the hole. Deployment of the internal fixation device 5100 into the uni-cortical hole 5051, and/or subsequent actuation of the internal fixation device, non-movably couples the internal fixation device to an interior portion of the bone, which fixates the internal fixation device relative to the bone. Prior to or after deploying the internal fixation device 5100 into the uni-cortical hole 5051, the end 5061 of the cable 5060 is non-movably fixed to the internal fixation device. The end 5061 of the cable 5060 can be fixed to the internal fixation device 5100 using any of various fixation methods, such as fastening, swaging, crimping, adhering, bonding, and the like. After the end 5061 of the cable 5060 is fixed to the internal fixation device 5100 and the internal fixation device is fixed to the bone 5050 within the uni-cortical hole 5041, the cable 5060 can be tensioned to a measurable and adjustable tension to fixate the cable 5060 relative to the bone 5050.

Prior to being tensioned, the cable 5060 extending from the uni-cortical hole 5051 may be wrapped at least partially around the bone and/or may extend through another hole in the bone in some implementations. Whether wrapped around the bone, extended through another hole in the bone, or not, the free end of the cable 5060 is coupled to an external device, instrument, or component. In this manner, after tensioning the cable 5060 with a tensioning device, the tensioned cable acts to fixate the external device, instrument, or component relative to the bone 5050, which maintains the cable 5060 in tension and maintains compression of the bone. In one implementation, the external component is a washer 5120 and a crimp body 5105, such as shown in FIG.

38. The washer may be positioned over the opening of the uni-cortical hole 5051 and, with the cable 5060 in tension, the crimp body 5105 may be crimped about the cable 5060 and against the washer to sustainably retain the tension in the cable. According to another implementation, the external component is an external fixation device, such as one of the external fixation devices described herein.

Figure 38:
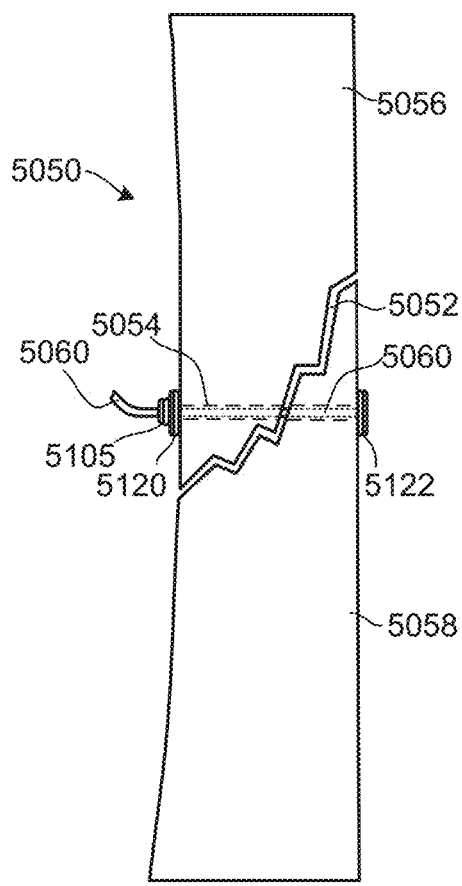
FIG. 38 is a side view of a tensioned cable extending through a bi-cortical hole formed in a fractured bone, according to one embodiment.

Referring to FIG. 38, according to one embodiment, the system 5660 can be used to tension a cable, within a bi-cortical hole extending between two fractured portions of the same bone, to a measurable and adjustable tension for compressing the two fractured portions together with a measurable and adjustable compression, thereby stabilizing the fracture in the bone. As shown, a bi-cortical hole 5054 is formed in a bone 5050 having a fracture 5052 that at least partially separates the bone into two portions 5056, 5058. The bi-cortical hole 5054 extends continuously through both portions 5056, 5058 of the bone 5050 separated by the fracture 5052. The portions 5056, 5058 of the bone 5050 are fixated relative to each other by passing a cable 5060 through the bi-cortical hole 5054 and, while the cable 5060 is positioned within the bi-cortical hole, anchoring one end of the cable relative to the bone 5050, tensioning the cable to a measurable and adjustable tension, and then anchoring an opposing end of the cable relative to the bone.

In the illustrated embodiment, a first end of the cable 5060 is anchored relative to the bone 5050 by fixedly coupling the first end of the cable to a washer 5122, which acts as a stop to prevent further passage of the cable through the bi-cortical hole 5054. With the washer 5122 preventing further passage of the cable 5060 through an open end of the bi-cortical hole 5054, the opposing end of the cable, which extends from an opposing open end of the bi-cortical hole, is tensioned to a measurable and adjustable tension with a tensioning device. Tensioning the cable 5060 to a measurable and adjustable tension in this manner draws the portions 5056, 5058 of the bone 5050 together, into firm contact with each other along the fracture 5052, to compress the portions 5056, 5058 of the bone together with a measurable and adjustable compression. While the cable 5060 is tensioned by the tensioning device, a crimp body 5105 is crimped about the opposing end of the cable. In one implementation, the crimp body 5105 is large enough to act as a stop to prevent the crimp body from passing through the bi-cortical hole 5054, thus retaining the tension in the cable. Alternatively, as shown, a washer 5120 may be positioned over the opposing open end of the bi-cortical hole 5054 and, with the cable 5060 in tension, the crimp body 5105 may be crimped about the cable 5060 and against the washer 5120, which, being larger than the opposing open end of the bi-cortical hole, acts as a stop, to sustainably retain the tension in the cable.

As mentioned above, because the hole 5054 extends through two bone portions or segments of a fractured bone, tensioning the cable 5060 to a measurable and adjustable tension, and crimping the cable 5060, causes the two bone segments 5056, 5058 to compress together with a measurable and adjustable compression. Moreover, because the cable 5060 passes through the bone, as opposed to around the bone, the compression of the two bone segments 5056, 5058 is applied in one direction (e.g., unidirectionally) concentric with the cable 5060, to more uniformly and evenly distribute the compressive load to the bone segments, as opposed to multiple directions when compression is applied by a cable passing around the bone.

Figure 39:
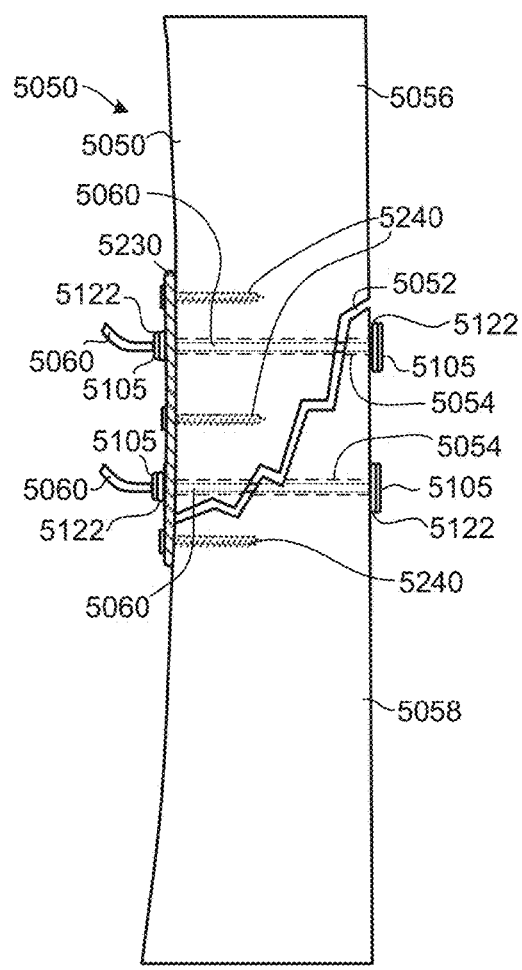
FIG. 39 is a side view of tensioned cables extending through bi-cortical holes formed in a fractured bone and anchored to a plate disposed on an outer surface of the bone to fixate the plate relative to the bone, according to one embodiment.

Referring to FIG. 39, according to one embodiment, the system 5660 can be used to tension a cable, within a bi-cortical hole extending between two fractured portions of the same bone, to a measurable and adjustable tension for fixating a simple internal fixation device, such as a plate, relative to and stabilizing a fracture in the bone. As shown, two bi-cortical holes 5054 are formed in a bone 5050 having a fracture 5052 that at least partially separates the bone into two portions 5056, 5058. The bi-cortical holes 5054 are spaced apart and extend continuously through both portions 5056, 5058 of the bone 5050 separated by the fracture 5052. The portions 5056, 5058 of the bone 5050 are fixated relative to each other by passing a separate cable 5060 through each of the bi-cortical holes 5054 and, while the cables 5060 are positioned within the respective bi-cortical holes, anchoring one end of the cables relative to the bone 5050, tensioning the cables to a measurable and adjustable tension, and then anchoring opposing ends of the cables relative to the bone.

In the illustrated embodiment, first ends of the cables 5060 are anchored relative to the bone 5050 by fixedly coupling the first ends of the cable to respective washers 5122, which act as stops to prevent further passage of the cables through the bi-cortical holes 5054. With the washers 5122 preventing further passage of the cables 5060 through open ends of the bi-cortical holes 5054, the opposing ends of the cables, which extend from respective opposing open ends of the bi-cortical holes, are tensioned to a measurable and adjustable tension with a tensioning device. Tensioning the cable 5060 to a measurable and adjustable tension in this manner draws the portions 5056, 5058 of the bone 5050 together, into firm contact with each other along the fracture 5052, to compress the portions 5056, 5058 of the bone together with a measurable and adjustable compression. Prior to or after tensioning the cables 5060, a plate 5230 is positioned on the bone 5050 adjacent the opposing open ends of the bi-cortical holes 5054. The plate 5230 is made from a rigid material so as to distribute loads across the plate, and thus a larger area of the bone 5050. Additionally, the plate 5230 includes apertures that are alignable with the opposing open ends of the bi-cortical holes 5054 such that the opposing end of each cable 5060 may extend through a respective opposing open end of a bi-cortical hole and aperture in the plate 5230 that are aligned with each other. Optionally, fasteners 5240 may be driven through the plate 5230 and into the bone 5050 to at least partially fixate the plate 5230 relative to the bone.

After the cables 5060 extend through the opposing open ends of the bi-cortical holes 5054 and the apertures in the plate 5230, and while the cables 5060 are tensioned by the tensioning device, crimp bodies 5105 are crimped about respective opposing ends of the cable and against the plate 5230 to sustainably retain the tension in the cables. Alternatively, as shown, washers 5122 may be positioned over the apertures in the plate 5230, and with the cables 5060 in tension, the crimp bodies 5105 may be crimped about the cables 5060 and against the washers 5122, which, being larger than the apertures in the plate, act as stops, to sustainably retain the tension in the cables.

As mentioned above, because the holes 5054 extend through two bone portions or segments 5056, 5058 of a fractured bone, tensioning the cables 5060 to a measurable and adjustable tension, and crimping the cables 5060, causes the two bone segments 5056, 5058 to compress together with a measurable and adjustable compression. Moreover, because the cables 5060 pass through the bone, as opposed to around the bone, the compression of the two bone segments 5056, 5058 from each cable 5060 is applied in one direction (e.g., unidirectionally) concentric with the respective cables, to more uniformly and evenly distribute the compressive loads from the cables 5060 to the bone segments, as opposed to multiple directions when compression is applied by cables passing around the bone.

Figure 40:
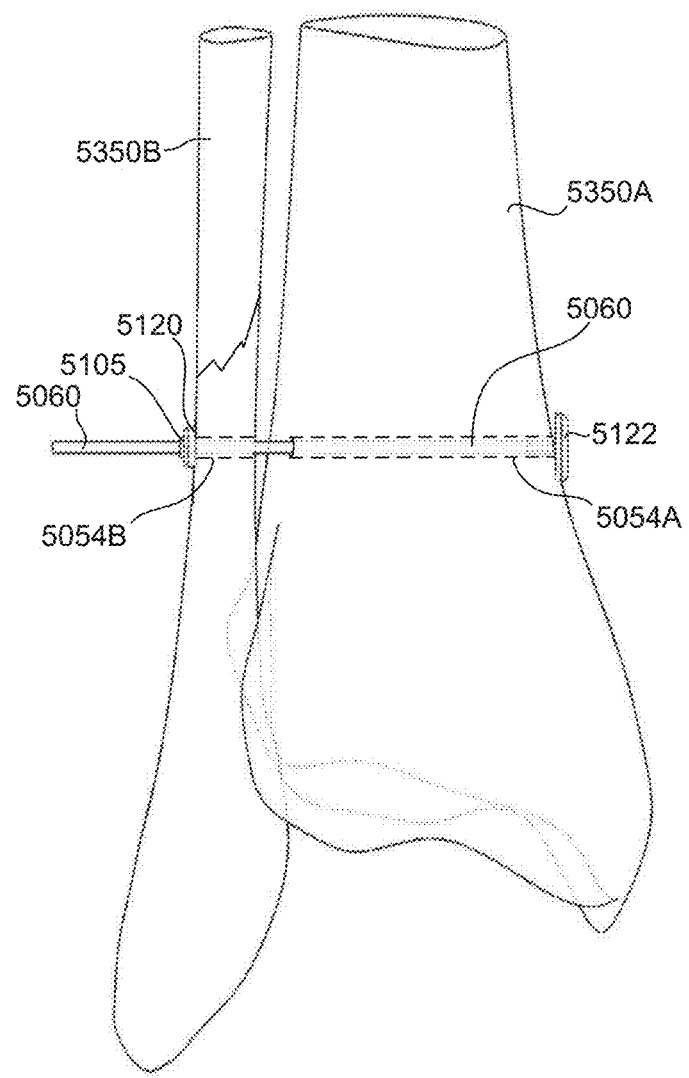
FIG. 40 is a side view of a tensioned cable extending through bi-cortical holes in separate bones, according to one embodiment.

Referring to FIG. 40, according to one embodiment, the system 5660 can be used to tension a cable, within bi-cortical holes extending between two separate bones (with at least one bone having a fracture, such as shown), to a measurable and adjustable tension, and thus cause a measurable and adjustable compression of the bones, for stabilizing the bones relative to each other. As shown, bi-cortical holes 5054A, 5054B are formed in respective bones 5350A, 5350B. Although separate and non-continuous relative to each other, the bi-cortical holes 5054A, 5054B are substantially coaxially aligned. The bi-cortical holes 5054A, 5054B can be formed together during a single action using the same drill forming device. Alternatively, the bi-cortical holes 5054A, 5054B may be formed separately during two separate actions, but ensuring the bi-cortical holes 5054A, 5054B remain substantially coaxially aligned. The bones 5350A, 5350B are fixated relative to each other by passing a cable 5060 through the bi-cortical holes 5054A, 5054B and, while the cable 5060 is positioned within the bi-cortical holes, anchoring one end of the cable relative to the bone 5350A, tensioning the cable to a measurable and adjustable tension, and then anchoring an opposing end of the cable relative to the bone 5350B.

In the illustrated embodiment, a first end of the cable 5060 is anchored relative to the bone 5350A by fixedly coupling the first end of the cable to a washer 5122, which acts as a stop to prevent further passage of the cable through the bi-cortical hole 5054A. With the washer 5122 preventing further passage of the cable 5060 through an open end of the bi-cortical hole 5054A, the opposing end of the cable, which extends from an opposing open end of the bi-cortical hole 5054B, is tensioned to a measurable and adjustable tension with a tensioning device. Tensioning the cable 5060 to a measurable and adjustable tension in this manner draws the bones 5350A, 5350B together and compresses the bones together with a measurable and adjustable compression. While the cable 5060 is tensioned by the tensioning device, a crimp body 5105 is crimped about the opposing end of the cable. In one implementation, the crimp body 5105 is large enough to act as a stop to prevent the crimp body from passing through the bi-cortical hole 5054B, thus retaining the tension in the cable. Alternatively, as shown, a washer 5120 may be positioned over the opposing open end of the bi-cortical hole 5054B and, with the cable 5060 in tension, the crimp body 5105 may be crimped about the cable 5060 and against the washer 5120, which, being larger than the opposing open end of the bi-cortical hole, acts as a stop, to sustainably retain the tension in the cable.

Because the holes 5054A, 5054B extend concentrically through two bones 5350A, 5350B, tensioning the cable 5060 to a measurable and adjustable tension, and crimping the cable 5060, causes the two bones to compress together with a measurable and adjustable compression. Moreover, because the cable 5060 passes through the bones 5350A, 5350B, as opposed to around the bones, the compression of the two bones is applied in one direction (e.g., unidirectionally) concentric with the cable 5060, to more uniformly and evenly distribute the compressive load to the bones, as opposed to multiple directions when compression is applied by a cable passing around the bones.

Figure 41:
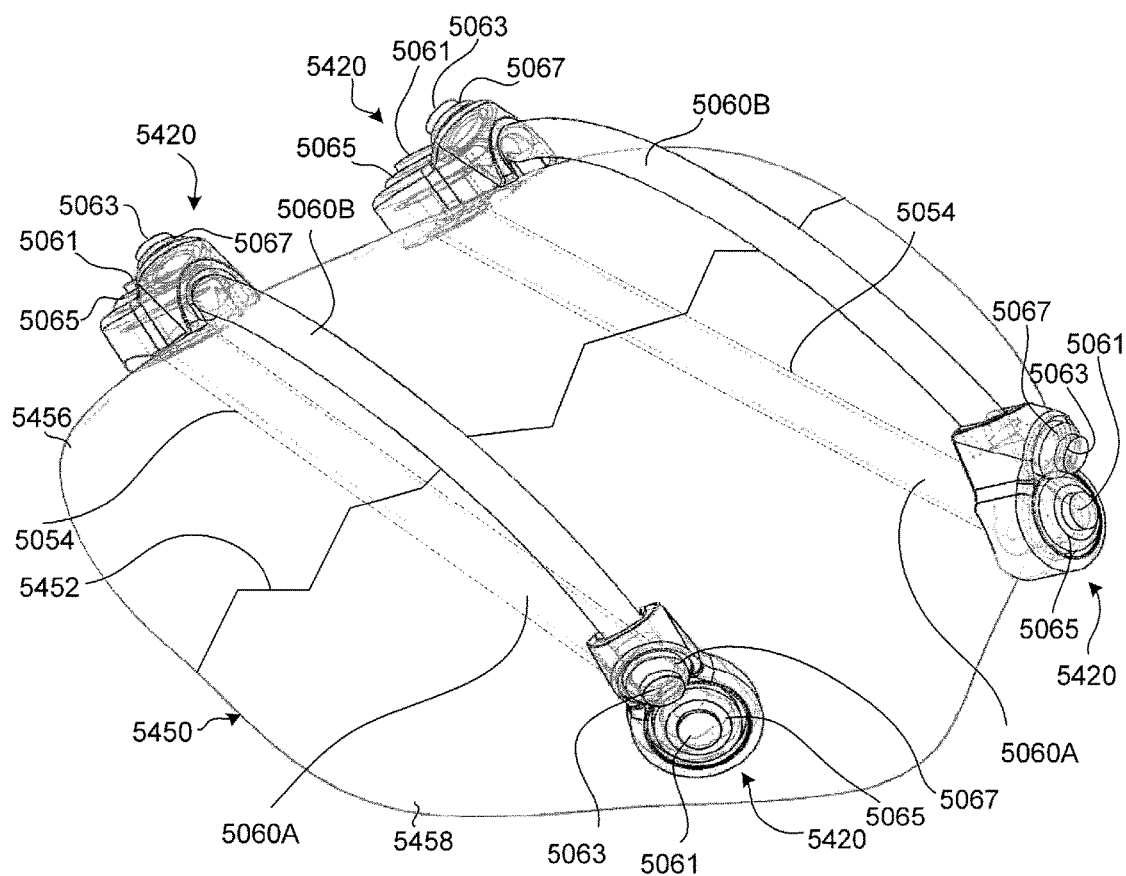
FIG. 41 is a perspective view of tensioned cables extending through bi-cortical holes formed in a fractured bone and tensioned cables extending around the fractured portions of the bone, according to one embodiment.

Referring to FIG. 41, according to one embodiment, the system 5660 can be used to tension a first cable, within a bi-cortical hole extending through two fractured portions of a bone and a second cable extending around (e.g., forming a cerclage about) the fractured portions of the bone, to measurable and adjustable tensions for compressing the two fractured portions together with a measurable and adjustable compression, thereby stabilizing the fracture in the bone. As shown, one or more bi-cortical holes 5054 are formed in a bone 5450 having a fracture 5452 that at least partially separates the bone into two portions 5456, 5458. The bi-cortical holes 5054 each extends continuously through both portions 5456, 5458 of the bone 5450 separated by the fracture 5452. The portions 5456, 5458 of the bone 5450 are fixated relative to each other by passing respective cables 5060A through the bi-cortical holes 5054 in the portions of the bones and passing respective cables 5060B around the external surfaces of the portions of the bone, and, while the cables 5060A, 5060B are thus positioned, anchoring one end of the cables 5060A, 5060B relative to the bone 5450, tensioning the cables to a measurable and adjustable tension, and then anchoring an opposing end of the cables relative to the bone. Because the holes 5054 extend through two bone portions or segments of a fractured bone, tensioning the cables 5060A, 5060B to a measurable and adjustable tension, and crimping the cables 5060A, 5060B, causes the two bone segments 5456, 5458 to compress together with a measurable and adjustable compression. Moreover, because the cables 5060A, 5060B pass through the bone, as opposed to around the bone, the compression of the two bone segments 5456, 5458 from each cable 5060A, 5060B is applied in one direction (e.g., unidirectionally) concentric with each cable 5060A, 5060B, to more uniformly and evenly distribute the compressive loads from the cables 5060A, 5060B to the bone segments, as opposed to multiple directions when compression is applied by cables passing around the bone In the illustrated embodiment, ends 5061 of the cables 5060A extending through the bi-cortical holes 5054 in the bone 5450 are anchored relative to the bone 5450 by coupling the ends 5061 to a respective one of a plurality of retention features. The retention feature can be a re-directional washer, such as washer 5420, and/or a stop, such as crimp body 5065. In the illustrated embodiment, the retention feature is both the washer 5420 and the crimp body 5065. More specifically, while the cables 5060A are positioned within the bi-cortical holes 5054, the ends 5061 of the cables 5060A extending from the washers 5420 may be crimped with the crimp body, which prevents further passage of the cables 5060A through the washers 5420 and the bi-cortical holes 5054. After one end 5061 of the cables 5060A is crimped in this manner, the opposing end 5061 of the cables 5060A is tensioned to a measurable and adjustable tension with a tensioning device. Tensioning the cables 5060A in this manner draws the portions 5456, 5458 of the bone 5450 together and into firm contact with each other along the fracture 5452. While the cables 5060A are tensioned by the tensioning device, the crimp body 5105 is crimped about the opposing ends 5061 of the cables 5060A to prevent the crimp bodies from passing through the washers 5420 and bi-cortical holes 5054, thus retaining the tension in the cables 5060A. Alternatively, other retention features can be used, such as conventional washers, crimp bodies without washers, balls, and the like.

Additionally, in the illustrated embodiment, ends 5063 of the cables 5060B extending around the bone 5450, which are separate from the cables 5060A, are anchored relative to the bone 5450 by coupling the ends 5063 to a respective one of a plurality of retention features. As shown, the retention features can be the same retentions features to which the ends 5061 of the cables 5060A are coupled, or they can be different retention features. Accordingly, the retention feature that retains the ends 5063 of the cables 5060B can be a re-directional washer, such as the washer 5420, and/or a stop, such as the crimp body 5065. In the illustrated embodiment, like the ends 5061 of the cables 5060A, the retention feature that retains the ends 5063 of the cables 5060B is both the washer 5420 and the crimp body 5065.

Figure 42:
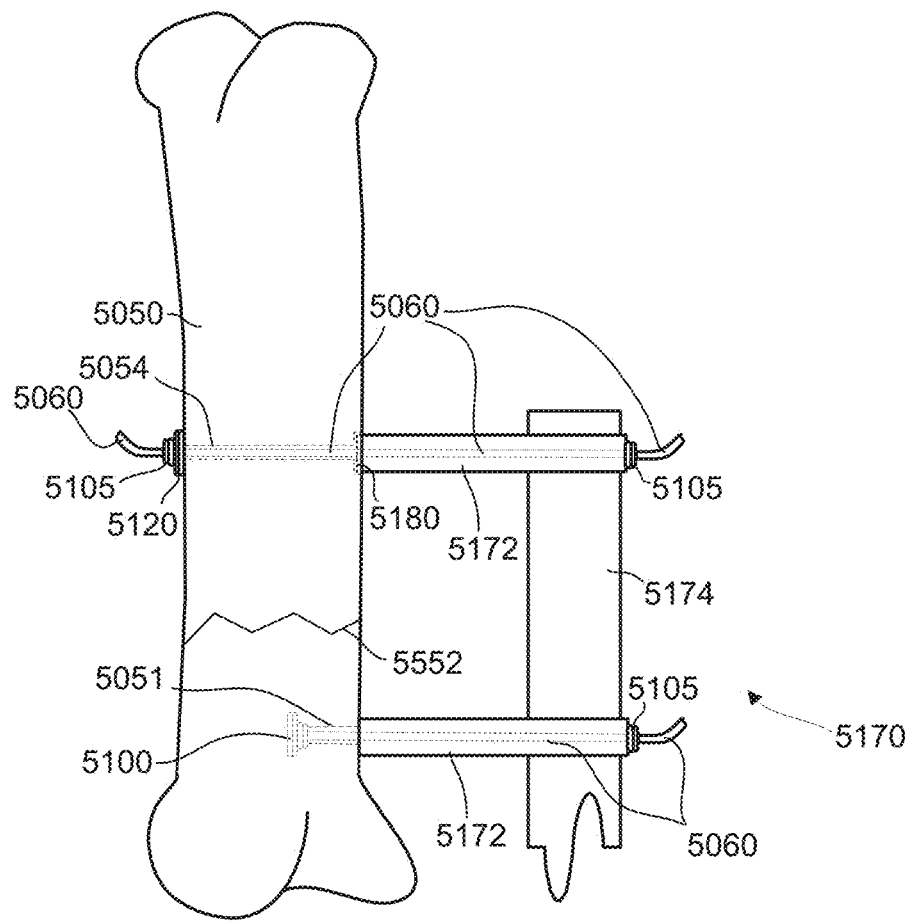
FIG. 42 is a side view of a tensioned cable extending through a bi-cortical hole formed in a bone and anchored to an external fixation device to fix the external fixation device relative to a segment of bone above the fracture, and another tensioned cable extending through a uni-cortical hole formed in the bone and anchored to an external fixation device to fix the external fixation device relative to a segment of bone below the fracture, according to one embodiment.

Referring to FIG. 42, according to one embodiment, the system 5660 can be used to tension a cable, disposed within a hole in a bone, to a measurable and adjustable tension for fixating complex external fixation devices relative to the bone. The hole may be a bi-cortical hole, such as bi-cortical hole 5054, or the hole may be a uni-cortical hole, such as uni-cortical hole 5051. Accordingly, an external fixation device, such as external fixation device 5170, can be used to fixate a bone with a fracture by securing the external fixation device to the bone via one or more tensioned cables positioned within, and anchored relative to, bi-cortical holes formed in the bone, uni-cortical holes formed in the bone, or both.

In one embodiment, the bi-cortical hole 5054 is formed in a bone 5050 having a fracture 5552 to be stabilized. The bi-cortical hole 5054 extends continuously through the bone 5050 from one side of the bone to an opposing side of the bone. A cable 5060 is passed through the bi-cortical hole 5054 and a rod 5172 of an external fixation device 5170. While the cable 5060 is positioned within the bi-cortical hole 5054 and the rod 5172, the cable is tensioned to a measurable and adjustable tension to fixate the external fixation device 5170 relative to the bone 5050.

In the illustrated embodiment, opposing ends of the cable 5060 are anchored relative to the bone 5050 by fixedly coupling the ends of the cable to a respective retention feature, such as a crimp body 5105 and/or a washer 5120. The retention feature acts as a stop to prevent further passage of the cable through the bi-cortical hole 5054. Generally, before or after passing the cable 5060 through the bi-cortical hole 5054 and rod 5172, a retention feature is fixedly coupled to one end of the cable 5060, which can be the end of the cable protruding from the bone 5050 or the end of the cable protruding from the rod 5172. With the retention feature fixedly coupled to one end of the cable, to prevent further passage of the cable 5060 through the bi-cortical hole 5054 and rod 5172 in one direction, the other end of the cable is received by a tensioning device to tension the cable to a measurable and adjustable tension. Tensioning the cable 5060 in this manner fixates the rod 5172 to the bone 5050. While the cable 5060 is tensioned by the tensioning device, the retention feature is fixedly coupled to the other end of the cable to sustainably retain the tension in the cable after the tensioning device is removed.

In some implementations, a recess 5180 or countersink can be formed in the bone 5050 to receive a portion of the rod 5172 prior to tensioning the cable 5060 and fixating the rod relative to the bone. The recess 5180 can formed around the bi-cortical hole 5054 and be coaxial with the bi-cortical hole. Moreover, the recess 5180 may be shaped to matingly receive an end of the rod 5172 in seated engagement.

As shown schematically, the external fixation device 5170 may also include a secondary component, such as a rail 5174, to which the rod 5172 is coupled. Accordingly, fixating the rod 5172 relative to the bone 5050 via a tensioned cable 5060 as described above correspondingly fixates the rail 5174 relative to the bone. The rod 5172 can be adjustably coupled to the rail 5174 such that a position or orientation of the rod relative to the rail may be adjusted.

The external fixation device 5170 may include additional rods 5172 each fixated relative to the bone 5050 via the same, or a separate, tensioned cable passing through a bi-cortical hole formed in the bone in the same manner as described above. Alternatively, one or all of the rods 5172 of the external fixation device 5170 may be fixated relative to the bone 5050 via a tensioned cable positioned within and anchored relative to a uni-cortical hole formed in the bone. For example, as shown, a cable 5060 is positioned within the uni-cortical hole 5051 formed in the bone 5050 and anchored within the uni-cortical hole via an internal fixation device 5100 or internal anchor positioned within the uni-cortical hole. The cable 5060 is then passed through the rod 5172, tensioned, and anchored to the rod via a crimp body 5105 in a manner similar to that described above. Based on the foregoing, the rail 5174 may facilitate the coupling of multiple rods 5172 of a single external fixation device to a bone using tensioned cables and bi-cortical holes, uni-cortical holes, or both.

Figure 43:
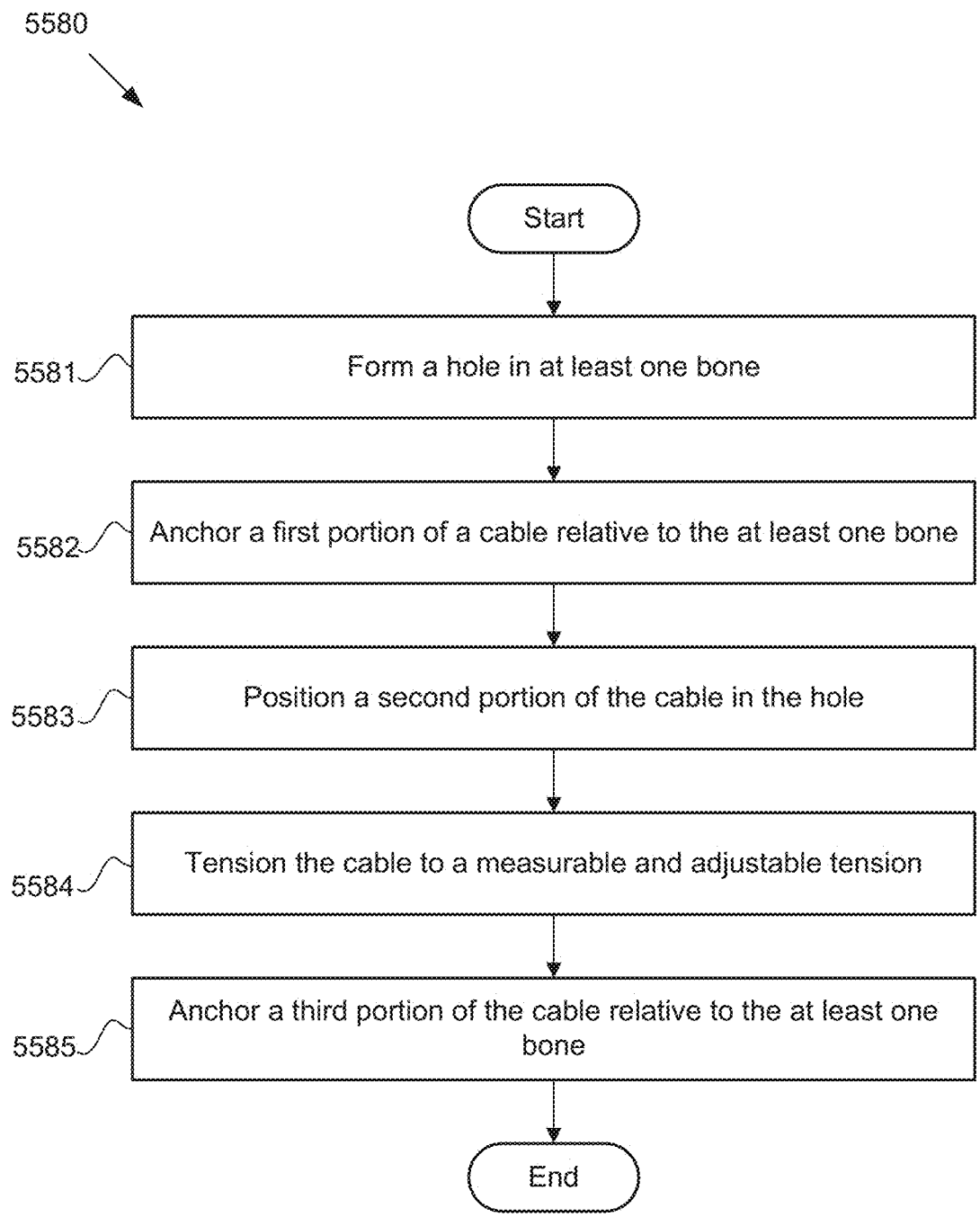
FIG. 43 is a schematic block diagram depicting a method for reducing and stabilizing fractures in bone, subluxations of bones, and dislocations of bones, according to one embodiment.

Referring to FIG. 43, and according to one embodiment, a method 5580 for reducing and stabilizing at least one of a fracture in, a dislocation of, and a subluxation of at least one bone includes forming a hole in the at least one bone at 5581. In one implementation, the hole is formed using any of various hole-forming tools, such as the apparatus 1100 for passing cable through bone described above. The method 5580 also includes anchoring a first portion of a cable relative to the at least one bone at 5582. According to some implementations, the first portion of the cable is anchored relative to bone using any of various anchoring tools, such as the apparatus 100 for anchoring cable to bone, the washer 3100 for supporting a cable, the stop 3146 fixed to an end of the cable, and the apparatus 4100 for attaching a crimp body to a cable described above. Additionally, the method 5580 includes positioning a second portion of the cable in the formed hole at 5583. In certain implementations, the second portion of the cable can be positioned in the hole by threading the cable into the hole or using the apparatus 1110 for passing cable through bone described above. The method 5580 further includes tensioning the cable to a measurable and adjustable tension at 5584. The cable can be tensioned to a measurable and adjustable tension, to cause a measurable and adjustable compression of the bone by the cable in some implementations, using any of various tensioning devices known in the art, particularly those tensioners with tension gauges integrated therein. According to certain implementations, tensioning the cable to a measurable and adjustable tension causes a unidirectional compression of the bone. In one implementation, the cable is tensioned using, at least in part, the apparatus 4100 described above. The method 5580 also includes anchoring a third portion of the cable relative to the at least one bone at 5585 while the cable is tensioned. According to some implementations, the third portion of the cable is anchored relative to the at least one bone using any of various anchoring tools, such as the washer 3100 for supporting a cable and the apparatus 4100 for attaching a crimp body to a cable described above.

Definitions

In the above description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C; or some other suitable combination. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The subject matter of the present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A method for reducing and stabilizing at least one of a fracture in, a dislocation of, and a subluxation of at least one bone, the method comprising: forming a hole in the at least one bone; anchoring a first portion of a cable relative to the at least one bone; positioning a second portion of the cable in the hole in the at least one bone; with the second portion of the cable positioned in the hole in the at least one bone: tensioning the cable to a measurable and adjustable tension, to cause a measurable and adjustable compression of the bone by the cable; and with the cable tensioned to the measurable tension, anchoring a third portion of the cable relative to the at least one bone, wherein the hole is a pass-through hole that extends from a first side of the at least one bone to a second side of the at least one bone, wherein forming the pass-through hole in the at least one bone comprises driving a hole forming tool through the at least one bone, wherein positioning the second portion of the cable in the pass-through hole in the at least one bone comprises passing a third portion through the pass-through hole in the at least one bone, wherein passing the third portion of the cable through the pass-through hole in the at least one bone comprises coupling the third portion of the cable to the hole-forming tool and collectively pulling the hole-forming tool and the third portion of the cable through the pass-through hole, wherein forming the pass-through hole in the at least one bone comprises driving a hole-forming tool through the at least one bone in a first direction from the first side of the at least one bone to form the pass-through hole until at least a first connection feature of the hole-forming tool protrudes from the pass through hole on the second side of the at least one bone, wherein passing the third portion of the cable through the pass-through hole in the at least one bone comprises: with the first connection feature of the hole-forming tool protruding from the pass-through hole on the second side of the at least one bone, coupling a second connection feature of the third portion of the cable to the first connection feature of the hole-forming tool; and after coupling the first and second connection features, withdrawing the hole forming tool from the pass-through hole in a second direction opposite the first direction to pull the third portion of the cable through the pass-through hole such that at least the third portion of the cable protrudes from the pass-through hole on the first side of the at least one bone.

2. The method of claim 1, further comprising re-tensioning the cable to a second measurable and adjustable tension.

3. The method of claim 1, further comprising coupling the cable to an internal bone fixation device, an external bone fixation device, or both an internal and external bone fixation device.

4. The method of claim 1, wherein forming the pass-through hole in the at least one bone comprises driving a hole-forming tool through the at least one bone in a first direction from the first side of the at least one bone to form the pass-through hole, and leaving at least a shank connection feature of the hole-forming tool protruding from the pass-through hole on the first side of the at least one bone.

5. The method of claim 4, wherein passing the third portion of the cable through the pass-through hole in the at least one bone comprises:
   with the shank connection feature of the hole-forming tool protruding from the pass-through hole on the first side of the at least one bone, coupling a second connection feature of the third portion of the cable to the shank connection feature of the hole-forming tool; and after coupling the shank and second connection features, withdrawing the hole-forming tool from the pass-through hole in the first direction to pull the cable through the pass-through hole such that the third portion of the cable protrudes from the pass-through hole on the second side of the at least one bone.

6. The method of claim 4, further comprising:
passing the third portion of the cable from the pass-through hole in the at least one bone through a central passage continuously extending through a crimp body and an elongate shaft, wherein the crimp body is coupled to an end of the elongate shaft;
using the elongate shaft to position the crimp body in a desired position relative to the pass-through hole in the at least one bone, the third portion of the cable extending from the pass-through hole into the central passage of the crimp body;
with the crimp body in the desired position and the cabled tensioned to the measurable and adjustable tension, crimping the crimp body about the third portion of the cable; and
after crimping the crimp body about the third portion of the cable, detaching the crimp body from the elongate shaft.

7. The method of claim 4, further comprising supporting a redirection of the third portion of the cable relative to the pass-through hole in the at least one bone after passing through the pass-through hole in the at least one bone with a washer positioned over the pass-through hole in the at least one bone.

8. The method of claim 4, further comprising:
positioning a washer over the pass-through hole in the at least one bone such that a bone-engaging surface of the washer engages a surface of the at least one bone adjacent the pass-through hole;
passing the third portion of the cable through a pass-through aperture in the washer, the pass-through aperture extending in a first direction from the bone engaging surface to a cable-engaging surface; and
positioning the third portion of the cable in a channel of the washer, wherein the channel extends in a second direction that is at least one of non-parallel to and offset from the first direction.

9. The method of claim 1, wherein anchoring the first portion of the cable relative to the at least one bone comprises driving an anchor into the at least one bone, wherein the first portion of the cable is fixed to the anchor.

10. The method of claim 1, wherein anchoring the first portion of the cable relative to the at least one bone comprises:
releasably attaching a distal portion of a cable housing to an anchor, wherein:
the first portion of the cable is fixed to the anchor;
the cable housing comprises a passage; and
the second portion of the cable is non-fixedly positioned in the passage;
after attaching the distal portion of the cable housing to the anchor, co-rotating the cable housing and the anchor to drive the anchor into a at least one bone; and
after driving the anchor into the at least one bone, withdrawing the cable housing away from the at least one bone to collectively detach the anchor from the cable housing and remove the second portion of the cable from the passage of the cable housing.

11. The method of claim 1, further comprising connecting the cable to a soft-tissue fixation device.

12. The method of claim 1, wherein:
the hole is a uni-cortical hole; and
anchoring the first portion of the cable comprises fixating the first portion of the cable within the uni-cortical hole via an internal fixation device positioned within the uni-cortical hole.

13. The method of claim 1, further comprising coupling the third portion of the cable to an external fixation device, wherein tensioning the cable to the measurable and adjustable tension fixates the external fixation device relative to the at least one bone.

14. The method of claim 1, wherein the measurable and adjustable compression is unidirectional.

15. A method for reducing and stabilizing at least one of a fracture in, a dislocation of, and a subluxation of at least one bone, the method comprising: driving a hole-forming tool through the at least one bone to form a pass-through hole in the at least one bone, wherein the pass-through hole extends from a first side of the at least one bone to a second side of the at least one bone; anchoring a first portion of a cable relative to the at least one bone; coupling a second portion of the cable to the hole-forming tool and collectively pulling the hole-forming tool and the second portion of the cable through the pass through hole; supporting a redirection of the second portion of the cable relative to the pass through hole in the at least one bone after passing through the pass-through hole in the at least one bone with a washer positioned over the pass-through hole in the at least one bone; passing the second portion of the cable from the pass-through hole in the at least one bone through a central passage continuously extending through a crimp body and an elongate shaft, wherein the crimp body is coupled to an end of the elongate shaft; using the elongate shaft to position the crimp body in a desired position relative to the pass-through hole in the at least one bone, the second portion of the cable extending from the pass-through hole into the central passage of the crimp body; tensioning the cable to a measurable and adjustable tension with a third portion of the cable positioned in the pass-through hole, to cause a measurable and adjustable compression of the at least one bone by the cable; with the crimp body in the desired position and after tensioning the cable to the measurable and adjustable tension, crimping the crimp body about the second portion of the cable; and after crimping the crimp body about the second portion of the cable, detaching the crimp body from the elongate shaft, and further comprising connecting the cable to a soft-tissue fixation device.

16. The method of claim 15, further comprising coupling the cable to an internal bone fixation device, an external bone fixation device, or both an internal and external bone fixation device.

17. The method of claim 15, wherein anchoring the first portion of the cable relative to the at least one bone comprises driving an anchor into the at least one bone, wherein the first portion of the cable is fixed to the anchor.

* * * * *